US011542497B2

(12) United States Patent
Mano et al.

(10) Patent No.: US 11,542,497 B2
(45) Date of Patent: Jan. 3, 2023

(54) METHOD FOR EVALUATING MULTIPLE DIFFERENT GENES OF INTEREST

(71) Applicant: THE UNIVERSITY OF TOKYO, Tokyo (JP)

(72) Inventors: Hiroyuki Mano, Tokyo (JP); Shinji Kohsaka, Tokyo (JP); Masachika Ikegami, Tokyo (JP)

(73) Assignee: The University of Tokyo, Tokyo (JP)

( * ) Notice: Subject to any disclaimer, the term of this patent is extended or adjusted under 35 U.S.C. 154(b) by 635 days.

(21) Appl. No.: 16/498,618

(22) PCT Filed: Mar. 30, 2018

(86) PCT No.: PCT/JP2018/013539
§ 371 (c)(1),
(2) Date: Sep. 27, 2019

(87) PCT Pub. No.: WO2018/181863
PCT Pub. Date: Oct. 4, 2018

(65) Prior Publication Data
US 2021/0189383 A1 Jun. 24, 2021

(30) Foreign Application Priority Data

Mar. 30, 2017 (JP) .............................. JP2017-069085

(51) Int. Cl.
*C12N 15/10* (2006.01)
*C12Q 1/6886* (2018.01)
*G01N 33/50* (2006.01)
*G01N 33/574* (2006.01)

(52) U.S. Cl.
CPC ....... *C12N 15/1082* (2013.01); *C12Q 1/6886* (2013.01); *G01N 33/5011* (2013.01); *G01N 33/5748* (2013.01); *G01N 33/57484* (2013.01)

(58) Field of Classification Search
CPC .................................................. C12N 15/1082
USPC ............................................................ 506/4
See application file for complete search history.

(56) References Cited

PUBLICATIONS

Balabas et al (Familial Cancer, 2010, 9: 267-274).*
Editorial, Nature Medicine, "The future of cancer genomics," Feb. 2015, 21(2):99.
Ackerman et al., "EGFR delE709_T710insD: A Rare but Potentially EGFR Inhibitor Responsive Mutation in Non-Small-Cell Lung Cancer," Journal of Thoracic Oncology, Oct. 2012, 7(10):e19-e20.
Cross et al., "AZD9291, an Irreversible EGFR TKI, Overcomes T790M-Mediated Resistance to EGFR Inhibitors in Lung Cancer," Cancer Discovery, Sep. 2014 (online Jun. 3, 2014), 4(9):1046-1061.
Han et al., "Predictive and Prognostic Impact of Epidermal Growth Factor Receptor Mutation in Non-Small-Cell Lung Cancer Patients Treated with Gefitinib," Journal of Clinical Oncology, Apr. 10, 2005, 23(11):2493-2501.
He et al., "EGFR Exon 19 Insertions: A New Family of Sensitizing EGFR Mutations in Lung Adenocarcinoma," Clinical Cancer Research, Mar. 15, 2012 (online Dec. 21, 2011), 18(6):1790-1797.
Kancha et al., "Functional Analysis of Epidermal Growth Factor Receptor (EGFR) Mutations and Potential Implications for EGFR Targeted Therapy," Clin. Cancer Res., Jan. 15, 2009, 15(2):460-467.
Kohsaka et al., "A method of high-throughput functional evaluation of EGFR gene variants of unknown significance in cancer," Sci. Transl. Med., Nov. 15, 2017, 9:eaan6566, 12 pages.
Mano et al., "A method of high-throughput functional evaluation of EGFR gene variants of unknown significance in cancer," Nov. 16, 2017, http://www.amed.go.jp/news/release_20171116.html, 7 pages, search date Jun. 21, 2018, with partial English translation, 2 pages.
Thress et al,. "Acquired EGFR C797S mutation mediates resistance to AZD9291 in non-small cell lung cancer harboring EGFR T790M," Nature Medicine, Jun. 2015, 21(6):560-562, and two supplemental pages.
Watanabe et al., "Effectiveness of Gefitinib against Non-Small-Cell Lung Cancer with the Uncommon EGFR Mutations G719X and L861Q," Journal of Thoracic Oncology, Feb. 2014, 9(2):189-194.
Yasuda et al., "Structural, Biochemical, and Clinical Characterization of Epidermal Growth Factor Receptor (EGFR) Exon 20 Insertion Mutations in Lung Cancer," Sci. Transl. Med., 2013, 5(216):216ra177, 10 pages.
Kim et al., "Systematic Functional Interrogation of Rare Cancer Variants Identifies Oncogenic Alleles," Cancer Discovery, Jul. 1, 2016, 6(7):714-726.
Supplementary European Search Report dated Jan. 12, 2021 in EP 18775247.2.

* cited by examiner

*Primary Examiner* — Sean E Aeder
(74) *Attorney, Agent, or Firm* — Foley & Lardner LLP

(57) ABSTRACT

It is an object of the present invention to provide, for instance, a method for evaluating a function, such as transforming potential, of multiple different genes of interest, and a method capable of evaluating drug sensitivity of a subject having each gene of interest. The present invention relates to, for instance, a method for evaluating multiple different genes of interest, comprising the steps of: integrating, into host cell genomic DNA, polynucleotides each comprising a tag sequence and a gene of interest or a fragment thereof linked to the tag sequence; mixing a plurality of different host cells having the different polynucleotides integrated therein; culturing the mixed host cells; extracting the genomic DNA from the cultured host cells; quantifying each of the polynucleotides in the extracted genomic DNA based on the tag sequence; and determining a relative cell count of each of the host cells having the respective polynucleotides after the culturing, based on the quantified values for the polynucleotides.

16 Claims, 12 Drawing Sheets
Specification includes a Sequence Listing.

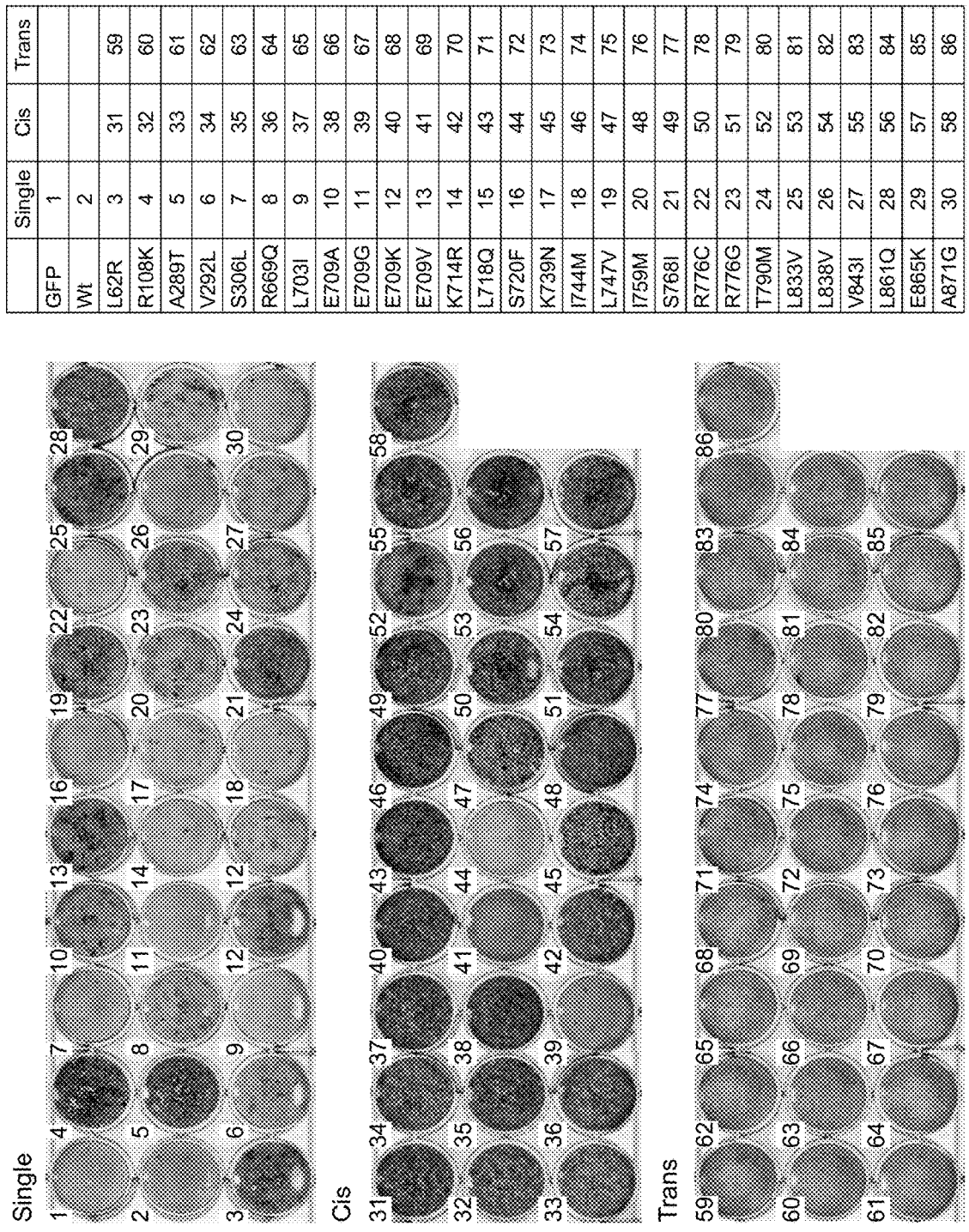

SEQUENCE LISTING

<160> NUMBER OF SEQ ID NOS: 14

<210> SEQ ID NO 1
<211> LENGTH: 1210
<212> TYPE: PRT
<213> ORGANISM: Homo sapiens

<400> SEQUENCE: 1

| | | | | | | | | | | | | | | |
|---|---|---|---|---|---|---|---|---|---|---|---|---|---|---|
| Met | Arg | Pro | Ser | Gly | Thr | Ala | Gly | Ala | Ala | Leu | Leu | Ala | Leu | Leu | Ala |
| 1 | | | | 5 | | | | | 10 | | | | | 15 | |
| Ala | Leu | Cys | Pro | Ala | Ser | Arg | Ala | Leu | Glu | Glu | Lys | Lys | Val | Cys | Gln |
| | | | 20 | | | | | 25 | | | | | 30 | | |
| Gly | Thr | Ser | Asn | Lys | Leu | Thr | Gln | Leu | Gly | Thr | Phe | Glu | Asp | His | Phe |
| | | 35 | | | | | 40 | | | | | 45 | | | |
| Leu | Ser | Leu | Gln | Arg | Met | Phe | Asn | Asn | Cys | Glu | Val | Val | Leu | Gly | Asn |
| | 50 | | | | | 55 | | | | | 60 | | | | |
| Leu | Glu | Ile | Thr | Tyr | Val | Gln | Arg | Asn | Tyr | Asp | Leu | Ser | Phe | Leu | Lys |
| 65 | | | | 70 | | | | | 75 | | | | | 80 | |
| Thr | Ile | Gln | Glu | Val | Ala | Gly | Tyr | Val | Leu | Ile | Ala | Leu | Asn | Thr | Val |
| | | | | 85 | | | | | 90 | | | | | 95 | |
| Glu | Arg | Ile | Pro | Leu | Glu | Asn | Leu | Gln | Ile | Ile | Arg | Gly | Asn | Met | Tyr |
| | | | 100 | | | | | 105 | | | | | 110 | | |
| Tyr | Glu | Asn | Ser | Tyr | Ala | Leu | Ala | Val | Leu | Ser | Asn | Tyr | Asp | Ala | Asn |
| | | | 115 | | | | | 120 | | | | | 125 | | |
| Lys | Thr | Gly | Leu | Lys | Glu | Leu | Pro | Met | Arg | Asn | Leu | Gln | Glu | Ile | Leu |
| | | 130 | | | | | 135 | | | | | 140 | | | |
| His | Gly | Ala | Val | Arg | Phe | Ser | Asn | Asn | Pro | Ala | Leu | Cys | Asn | Val | Glu |
| 145 | | | | | 150 | | | | | 155 | | | | | 160 |
| Ser | Ile | Gln | Trp | Arg | Asp | Ile | Val | Ser | Ser | Asp | Phe | Leu | Ser | Asn | Met |
| | | | | 165 | | | | | 170 | | | | | 175 | |
| Ser | Met | Asp | Phe | Gln | Asn | His | Leu | Gly | Ser | Cys | Gln | Lys | Cys | Asp | Pro |
| | | | 180 | | | | | 185 | | | | | 190 | | |
| Ser | Cys | Pro | Asn | Gly | Ser | Cys | Trp | Gly | Ala | Gly | Glu | Glu | Asn | Cys | Gln |
| | | | 195 | | | | | 200 | | | | | 205 | | |
| Lys | Leu | Thr | Lys | Ile | Ile | Cys | Ala | Gln | Gln | Cys | Ser | Gly | Arg | Cys | Arg |
| | | 210 | | | | | 215 | | | | | 220 | | | |
| Gly | Lys | Ser | Pro | Ser | Asp | Cys | Cys | His | Asn | Gln | Cys | Ala | Ala | Gly | Cys |
| 225 | | | | | 230 | | | | | 235 | | | | | 240 |
| Thr | Gly | Pro | Arg | Glu | Ser | Asp | Cys | Leu | Val | Cys | Arg | Lys | Phe | Arg | Asp |
| | | | | 245 | | | | | 250 | | | | | 255 | |
| Glu | Ala | Thr | Cys | Lys | Asp | Thr | Cys | Pro | Pro | Leu | Met | Leu | Tyr | Asn | Pro |
| | | | 260 | | | | | 265 | | | | | 270 | | |
| Thr | Thr | Tyr | Gln | Met | Asp | Val | Asn | Pro | Glu | Gly | Lys | Tyr | Ser | Phe | Gly |
| | | 275 | | | | | 280 | | | | | 285 | | | |
| Ala | Thr | Cys | Val | Lys | Lys | Cys | Pro | Arg | Asn | Tyr | Val | Val | Thr | Asp | His |
| | | 290 | | | | | 295 | | | | | 300 | | | |
| Gly | Ser | Cys | Val | Arg | Ala | Cys | Gly | Ala | Asp | Ser | Tyr | Glu | Met | Glu | Glu |
| 305 | | | | | 310 | | | | | 315 | | | | | 320 |
| Asp | Gly | Val | Arg | Lys | Cys | Lys | Lys | Cys | Glu | Gly | Pro | Cys | Arg | Lys | Val |
| | | | | 325 | | | | | 330 | | | | | 335 | |
| Cys | Asn | Gly | Ile | Gly | Ile | Gly | Glu | Phe | Lys | Asp | Ser | Leu | Ser | Ile | Asn |
| | | | 340 | | | | | 345 | | | | | 350 | | |
| Ala | Thr | Asn | Ile | Lys | His | Phe | Lys | Asn | Cys | Thr | Ser | Ile | Ser | Gly | Asp |
| | | 355 | | | | | 360 | | | | | 365 | | | |

-continued

```
Leu His Ile Leu Pro Val Ala Phe Arg Gly Asp Ser Phe Thr His Thr
370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                405                 410                 415
Leu His Ala Phe Glu Asn Leu Glu Ile Ile Arg Gly Arg Thr Lys Gln
                420                 425                 430
His Gly Gln Phe Ser Leu Ala Val Val Ser Leu Asn Ile Thr Ser Leu
            435                 440                 445
Gly Leu Arg Ser Leu Lys Glu Ile Ser Asp Gly Asp Val Ile Ile Ser
450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
                500                 505                 510
Glu Gly Cys Trp Gly Pro Glu Pro Arg Asp Cys Val Ser Cys Arg Asn
            515                 520                 525
Val Ser Arg Gly Arg Glu Cys Val Asp Lys Cys Asn Leu Leu Glu Gly
530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
                580                 585                 590
Lys Thr Cys Pro Ala Gly Val Met Gly Glu Asn Asn Thr Leu Val Trp
            595                 600                 605
Lys Tyr Ala Asp Ala Gly His Val Cys His Leu Cys His Pro Asn Cys
610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg Arg His
                660                 665                 670
Ile Val Arg Lys Arg Thr Leu Arg Arg Leu Leu Gln Glu Arg Glu Leu
            675                 680                 685
Val Glu Pro Leu Thr Pro Ser Gly Glu Ala Pro Asn Gln Ala Leu Leu
690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
                725                 730                 735
Lys Val Lys Ile Pro Val Ala Ile Lys Glu Leu Arg Glu Ala Thr Ser
                740                 745                 750
Pro Lys Ala Asn Lys Glu Ile Leu Asp Glu Ala Tyr Val Met Ala Ser
            755                 760                 765
Val Asp Asn Pro His Val Cys Arg Leu Leu Gly Ile Cys Leu Thr Ser
770                 775                 780
Thr Val Gln Leu Ile Thr Gln Leu Met Pro Phe Gly Cys Leu Leu Asp
```

```
                785                 790                 795                 800
Tyr Val Arg Glu His Lys Asp Asn Ile Gly Ser Gln Tyr Leu Leu Asn
                    805                 810                 815

Trp Cys Val Gln Ile Ala Lys Gly Met Asn Tyr Leu Glu Asp Arg Arg
                820                 825                 830

Leu Val His Arg Asp Leu Ala Ala Arg Asn Val Leu Val Lys Thr Pro
                835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
                900                 905                 910

Lys Pro Tyr Asp Gly Ile Pro Ala Ser Glu Ile Ser Ser Ile Leu Glu
                915                 920                 925

Lys Gly Glu Arg Leu Pro Gln Pro Pro Ile Cys Thr Ile Asp Val Tyr
            930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
            995                  1000                 1005

Asp Val  Val Asp Ala Asp Glu  Tyr Leu Ile Pro Gln  Gln Gly Phe
    1010                 1015                 1020

Phe Ser  Ser Pro Ser Thr Ser  Arg Thr Pro Leu Leu  Ser Ser Leu
    1025                 1030                 1035

Ser Ala  Thr Ser Asn Asn Ser  Thr Val Ala Cys Ile  Asp Arg Asn
    1040                 1045                 1050

Gly Leu  Gln Ser Cys Pro Ile  Lys Glu Asp Ser Phe  Leu Gln Arg
    1055                 1060                 1065

Tyr Ser  Ser Asp Pro Thr Gly  Ala Leu Thr Glu Asp  Ser Ile Asp
    1070                 1075                 1080

Asp Thr  Phe Leu Pro Val Pro  Glu Tyr Ile Asn Gln  Ser Val Pro
    1085                 1090                 1095

Lys Arg  Pro Ala Gly Ser Val  Gln Asn Pro Val Tyr  His Asn Gln
    1100                 1105                 1110

Pro Leu  Asn Pro Ala Pro Ser  Arg Asp Pro His Tyr  Gln Asp Pro
    1115                 1120                 1125

His Ser  Thr Ala Val Gly Asn  Pro Glu Tyr Leu Asn  Thr Val Gln
    1130                 1135                 1140

Pro Thr  Cys Val Asn Ser Thr  Phe Asp Ser Pro Ala  His Trp Ala
    1145                 1150                 1155

Gln Lys  Gly Ser His Gln Ile  Ser Leu Asp Asn Pro  Asp Tyr Gln
    1160                 1165                 1170

Gln Asp  Phe Phe Pro Lys Glu  Ala Lys Pro Asn Gly  Ile Phe Lys
    1175                 1180                 1185

Gly Ser  Thr Ala Glu Asn Ala  Glu Tyr Leu Arg Val  Ala Pro Gln
    1190                 1195                 1200
```

Ser Ser Glu Phe Ile Gly Ala
    1205              1210

<210> SEQ ID NO 2
<211> LENGTH: 3633
<212> TYPE: DNA
<213> ORGANISM: Homo sapiens

<400> SEQUENCE: 2

| | | | | | |
|---|---|---|---|---|---|
| atgcgaccct | ccgggacggc | cggggcagcg | ctcctggcgc | tgctggctgc | gctctgcccg | 60 |
| gcgagtcggg | ctctggagga | aaagaaagtt | tgccaaggca | cgagtaacaa | gctcacgcag | 120 |
| ttgggcactt | ttgaagatca | tttctcagc | ctccagagga | tgttcaataa | ctgtgaggtg | 180 |
| gtccttggga | atttggaaat | tacctatgtg | cagaggaatt | atgatctttc | cttcttaaag | 240 |
| accatccagg | aggtggctgg | ttatgtcctc | attgccctca | acacagtgga | gcgaattcct | 300 |
| ttggaaaacc | tgcagatcat | cagaggaaat | atgtactacg | aaaattccta | tgccttagca | 360 |
| gtcttatcta | actatgatgc | aaataaaacc | ggactgaagg | agctgccat | gagaaattta | 420 |
| caggaaatcc | tgcatggcgc | cgtgcggttc | agcaacaacc | ctgccctgtg | caacgtggag | 480 |
| agcatccagt | ggcgggacat | agtcagcagt | gactttctca | gcaacatgtc | gatggacttc | 540 |
| cagaaccacc | tgggcagctg | ccaaaagtgt | gatccaagct | gtcccaatgg | agctgctgg | 600 |
| ggtgcaggag | aggagaactg | ccagaaactg | accaaaatca | tctgtgccca | gcagtgctcc | 660 |
| gggcgctgcc | gtggcaagtc | ccccagtgac | tgctgccaca | accagtgtgc | tgcaggctgc | 720 |
| acaggccccc | gggagagcga | ctgcctggtc | tgccgcaaat | tccgagacga | agccacgtgc | 780 |
| aaggacacct | gccccccact | catgctctac | aaccccacca | cgtaccagat | ggatgtgaac | 840 |
| cccgagggca | aatacagctt | tggtgccacc | tgcgtgaaga | agtgtccccg | taattatgtg | 900 |
| gtgacagatc | acggctcgtg | cgtccgagcc | tgtgggccg | acagctatga | gatggaggaa | 960 |
| gacggcgtcc | gcaagtgtaa | gaagtgcgaa | gggccttgcc | gcaaagtgtg | taacggaata | 1020 |
| ggtattggtg | aatttaaaga | ctcactctcc | ataaatgcta | cgaatattaa | acacttcaaa | 1080 |
| aactgcacct | ccatcagtgg | cgatctccac | atcctgccgg | tggcatttag | gggtgactcc | 1140 |
| ttcacacata | ctcctcctct | ggatccacag | gaactggata | ttctgaaaac | cgtaaaggaa | 1200 |
| atcacagggt | ttttgctgat | tcaggcttgg | cctgaaaaca | ggacggacct | ccatgccttt | 1260 |
| gagaacctag | aaatcatacg | cggcaggacc | aagcaacatg | gtcagttttc | tcttgcagtc | 1320 |
| gtcagcctga | acataacatc | cttgggatta | cgctccctca | aggagataag | tgatggagat | 1380 |
| gtgataattt | caggaaacaa | aaatttgtgc | tatgcaaata | caataaactg | gaaaaaactg | 1440 |
| tttgggacct | ccggtcagaa | aaccaaaatt | ataagcaaca | gaggtgaaaa | cagctgcaag | 1500 |
| gccacaggcc | aggtctgcca | tgccttgtgc | tcccccgagg | gctgctgggg | cccggagccc | 1560 |
| agggactgcg | tctcttgccg | gaatgtcagc | cgaggcaggg | aatgcgtgga | caagtgcaac | 1620 |
| cttctggagg | gtgagccaag | ggagtttgtg | gagaactctg | agtgcataca | gtgccaccca | 1680 |
| gagtgcctgc | ctcaggccat | gaacatcacc | tgcacaggac | ggggaccaga | caactgtatc | 1740 |
| cagtgtgccc | actacattga | cggccccac | tgcgtcaaga | cctgcccggc | aggagtcatg | 1800 |
| ggagaaaaca | caccctggt | ctggaagtac | gcagacgccg | ccatgtgtg | ccacctgtgc | 1860 |
| catccaaact | gcacctacgg | atgcactggg | ccaggtcttg | aaggctgtcc | aacgaatggg | 1920 |
| cctaagatcc | cgtccatcgc | cactgggatg | gtggggccc | tcctcttgct | gctggtggtg | 1980 |
| gccctgggga | tcggcctctt | catgcgaagg | cgccacatcg | ttcggaagcg | cacgctgcgg | 2040 |

```
aggctgctgc aggagaggga gcttgtggag cctcttacac ccagtggaga agctcccaac    2100
caagctctct tgaggatctt gaaggaaact gaattcaaaa agatcaaagt gctgggctcc    2160
ggtgcgttcg gcacggtgta taagggactc tggatcccag aaggtgagaa agttaaaatt    2220
cccgtcgcta tcaaggaatt aagagaagca acatctccga aagccaacaa ggaaatcctc    2280
gatgaagcct acgtgatggc cagcgtggac aaccccacg tgtgccgcct gctgggcatc    2340
tgcctcacct ccaccgtgca gctcatcacg cagctcatgc ccttcggctg cctcctggac    2400
tatgtccggg aacacaaaga caatattggc tcccagtacc tgctcaactg gtgtgtgcag    2460
atcgcaaagg gcatgaacta cttggaggac cgtcgcttgg tgcaccgcga cctggcagcc    2520
aggaacgtac tggtgaaaac accgcagcat gtcaagatca cagattttgg gctggccaaa    2580
ctgctgggtg cggaagagaa agaataccat gcagaaggag gcaaagtgcc tatcaagtgg    2640
atggcattgg aatcaatttt acacagaatc tatacccacc agagtgatgt ctggagctac    2700
ggggtgactg tttgggagtt gatgaccttt ggatccaagc catatgacgg aatccctgcc    2760
agcgagatct cctccatcct ggagaaagga gaacgcctcc ctcagccacc catatgtacc    2820
atcgatgtct acatgatcat ggtcaagtgc tggatgatag acgcagatag tcgcccaaag    2880
ttccgtgagt tgatcatcga attctccaaa atggcccgag acccccagcg ctaccttgtc    2940
attcaggggg atgaaagaat gcatttgcca agtcctacag actccaactt ctaccgtgcc    3000
ctgatggatg aagaagacat ggacgacgtg gtggatgccg acgagtacct catcccacag    3060
cagggcttct tcagcagccc ctccacgtca cggactcccc tcctgagctc tctgagtgca    3120
accagcaaca attccaccgt ggcttgcatt gatagaaatg ggctgcaaag ctgtcccatc    3180
aaggaagaca gcttcttgca gcgatacagc tcagacccca caggcgcctt gactgaggac    3240
agcatagacg acaccttcct cccagtgcct gaatacataa accagtccgt tcccaaaagg    3300
cccgctggct ctgtgcagaa tcctgtctat cacaatcagc ctctgaaccc cgcgcccagc    3360
agagacccac actaccagga ccccacagc actgcagtgg gcaaccccga gtatctcaac    3420
actgtccagc ccacctgtgt caacagcaca ttcgacagcc ctgccactg ggcccagaaa    3480 ggcagccacc aaattagcct ggacaaccct gactaccagc aggacttctt tcccaaggaa    3540
gccaagccaa atggcatctt taagggctcc acagctgaaa atgcagaata cctaagggtc    3600
gcgccacaaa gcagtgaatt tattggagca tga                                 3633
```

<210> SEQ ID NO 3
<211> LENGTH: 1366
<212> TYPE: PRT
<213> ORGANISM: Homo sapiens

<400> SEQUENCE: 3

Met Leu Ser Phe Val Asp Thr Arg Thr Leu Leu Leu Ala Val Thr
1               5                   10                  15

Leu Cys Leu Ala Thr Cys Gln Ser Leu Gln Glu Glu Thr Val Arg Lys
            20                  25                  30

Gly Pro Ala Gly Asp Arg Gly Pro Arg Gly Glu Arg Gly Pro Pro Gly
        35                  40                  45

Pro Pro Gly Arg Asp Gly Glu Asp Gly Pro Thr Gly Pro Pro Gly Pro
    50                  55                  60

Pro Gly Pro Pro Gly Pro Pro Gly Leu Gly Gly Asn Phe Ala Ala Gln
65                  70                  75                  80

Tyr Asp Gly Lys Gly Val Gly Leu Gly Pro Gly Pro Met Gly Leu Met

```
                85                  90                  95
Gly Pro Arg Gly Pro Gly Ala Ala Gly Ala Pro Gly Pro Gln Gly
            100                 105                 110
Phe Gln Gly Pro Ala Gly Glu Pro Gly Glu Pro Gly Gln Thr Gly Pro
            115                 120                 125
Ala Gly Ala Arg Gly Pro Ala Gly Pro Pro Gly Lys Ala Gly Glu Asp
            130                 135                 140
Gly His Pro Gly Lys Pro Gly Arg Pro Gly Glu Arg Gly Val Val Gly
145                 150                 155                 160
Pro Gln Gly Ala Arg Gly Phe Pro Gly Thr Pro Gly Leu Pro Gly Phe
                165                 170                 175
Lys Gly Ile Arg Gly His Asn Gly Leu Asp Gly Leu Lys Gly Gln Pro
                180                 185                 190
Gly Ala Pro Gly Val Lys Gly Glu Pro Gly Ala Pro Gly Glu Asn Gly
                195                 200                 205
Thr Pro Gly Gln Thr Gly Ala Arg Gly Leu Pro Gly Glu Arg Gly Arg
            210                 215                 220
Val Gly Ala Pro Gly Pro Ala Gly Ala Arg Gly Ser Asp Gly Ser Val
225                 230                 235                 240
Gly Pro Val Gly Pro Ala Gly Pro Ile Gly Ser Ala Gly Pro Pro Gly
                245                 250                 255
Phe Pro Gly Ala Pro Gly Pro Lys Gly Glu Ile Gly Ala Val Gly Asn
                260                 265                 270
Ala Gly Pro Ala Gly Pro Ala Gly Pro Arg Gly Glu Val Gly Leu Pro
                275                 280                 285
Gly Leu Ser Gly Pro Val Gly Pro Pro Gly Asn Pro Gly Ala Asn Gly
                290                 295                 300
Leu Thr Gly Ala Lys Gly Ala Ala Gly Leu Pro Gly Val Ala Gly Ala
305                 310                 315                 320
Pro Gly Leu Pro Gly Pro Arg Gly Ile Pro Gly Pro Val Gly Ala Ala
                325                 330                 335
Gly Ala Thr Gly Ala Arg Gly Leu Val Gly Glu Pro Gly Pro Ala Gly
                340                 345                 350
Ser Lys Gly Glu Ser Gly Asn Lys Gly Glu Pro Gly Ser Ala Gly Pro
                355                 360                 365
Gln Gly Pro Pro Gly Pro Ser Gly Glu Glu Gly Lys Arg Gly Pro Asn
            370                 375                 380
Gly Glu Ala Gly Ser Ala Gly Pro Pro Gly Pro Pro Gly Leu Arg Gly
385                 390                 395                 400
Ser Pro Gly Ser Arg Gly Leu Pro Gly Ala Asp Gly Arg Ala Gly Val
                405                 410                 415
Met Gly Pro Pro Gly Ser Arg Gly Ala Ser Gly Pro Ala Gly Val Arg
            420                 425                 430
Gly Pro Asn Gly Asp Ala Gly Arg Pro Gly Glu Pro Gly Leu Met Gly
            435                 440                 445
Pro Arg Gly Leu Pro Gly Ser Pro Gly Asn Ile Gly Pro Ala Gly Lys
            450                 455                 460
Glu Gly Pro Val Gly Leu Pro Gly Ile Asp Gly Arg Pro Gly Pro Ile
465                 470                 475                 480
Gly Pro Ala Gly Ala Arg Gly Glu Pro Gly Asn Ile Gly Phe Pro Gly
                485                 490                 495
Pro Lys Gly Pro Thr Gly Asp Pro Gly Lys Asn Gly Asp Lys Gly His
            500                 505                 510
```

```
Ala Gly Leu Ala Gly Ala Arg Gly Ala Pro Gly Pro Asp Gly Asn Asn
            515                 520                 525

Gly Ala Gln Gly Pro Pro Gly Pro Gln Gly Val Gln Gly Gly Lys Gly
    530                 535                 540

Glu Gln Gly Pro Pro Gly Pro Pro Gly Phe Gln Gly Leu Pro Gly Pro
545                 550                 555                 560

Ser Gly Pro Ala Gly Glu Val Gly Lys Pro Gly Glu Arg Gly Leu His
                565                 570                 575

Gly Glu Phe Gly Leu Pro Gly Pro Ala Gly Pro Arg Gly Glu Arg Gly
            580                 585                 590

Pro Pro Gly Glu Ser Gly Ala Ala Gly Pro Thr Gly Pro Ile Gly Ser
        595                 600                 605

Arg Gly Pro Ser Gly Pro Pro Gly Pro Asp Gly Asn Lys Gly Glu Pro
    610                 615                 620

Gly Val Val Gly Ala Val Gly Thr Ala Gly Pro Ser Gly Pro Ser Gly
625                 630                 635                 640

Leu Pro Gly Glu Arg Gly Ala Ala Gly Ile Pro Gly Gly Lys Gly Glu
                645                 650                 655

Lys Gly Glu Pro Gly Leu Arg Gly Glu Ile Gly Asn Pro Gly Arg Asp
            660                 665                 670

Gly Ala Arg Gly Ala Pro Gly Ala Val Gly Ala Pro Gly Pro Ala Gly
        675                 680                 685

Ala Thr Gly Asp Arg Gly Glu Ala Gly Ala Ala Gly Pro Ala Gly Pro
    690                 695                 700

Ala Gly Pro Arg Gly Ser Pro Gly Glu Arg Gly Glu Val Gly Pro Ala
705                 710                 715                 720

Gly Pro Asn Gly Phe Ala Gly Pro Ala Gly Ala Ala Gly Gln Pro Gly
                725                 730                 735

Ala Lys Gly Glu Arg Gly Ala Lys Gly Pro Lys Gly Glu Asn Gly Val
            740                 745                 750

Val Gly Pro Thr Gly Pro Val Gly Ala Ala Gly Pro Ala Gly Pro Asn
        755                 760                 765

Gly Pro Pro Gly Pro Ala Gly Ser Arg Gly Asp Gly Gly Pro Pro Gly
    770                 775                 780

Met Thr Gly Phe Pro Gly Ala Ala Gly Arg Thr Gly Pro Pro Gly Pro
785                 790                 795                 800

Ser Gly Ile Ser Gly Pro Pro Gly Pro Pro Gly Pro Ala Gly Lys Glu
                805                 810                 815

Gly Leu Arg Gly Pro Arg Gly Asp Gln Gly Pro Val Gly Arg Thr Gly
            820                 825                 830

Glu Val Gly Ala Val Gly Pro Pro Gly Phe Ala Gly Glu Lys Gly Pro
        835                 840                 845

Ser Gly Glu Ala Gly Thr Ala Gly Pro Pro Gly Thr Pro Gly Pro Gln
    850                 855                 860

Gly Leu Leu Gly Ala Pro Gly Ile Leu Gly Leu Pro Gly Ser Arg Gly
865                 870                 875                 880

Glu Arg Gly Leu Pro Gly Val Ala Gly Ala Val Gly Glu Pro Gly Pro
                885                 890                 895

Leu Gly Ile Ala Gly Pro Pro Gly Ala Arg Gly Pro Pro Gly Ala Val
            900                 905                 910

Gly Ser Pro Gly Val Asn Gly Ala Pro Gly Glu Ala Gly Arg Asp Gly
        915                 920                 925
```

```
Asn Pro Gly Asn Asp Gly Pro Pro Gly Arg Asp Gly Gln Pro Gly His
    930                 935                 940

Lys Gly Glu Arg Gly Tyr Pro Gly Asn Ile Gly Pro Val Gly Ala Ala
945                 950                 955                 960

Gly Ala Pro Gly Pro His Gly Pro Val Gly Pro Ala Gly Lys His Gly
                965                 970                 975

Asn Arg Gly Glu Thr Gly Pro Ser Gly Pro Val Gly Pro Ala Gly Ala
            980                 985                 990

Val Gly Pro Arg Gly Pro Ser Gly  Pro Gln Gly Ile Arg  Gly Asp Lys
        995                 1000                1005

Gly Glu  Pro Gly Glu Lys Gly  Pro Arg Gly Leu Pro  Gly Leu Lys
    1010                1015                1020

Gly His  Asn Gly Leu Gln Gly  Leu Pro Gly Ile Ala  Gly His His
    1025                1030                1035

Gly Asp  Gln Gly Ala Pro Gly  Ser Val Gly Pro Ala  Gly Pro Arg
    1040                1045                1050

Gly Pro  Ala Gly Pro Ser Gly  Pro Ala Gly Lys Asp  Gly Arg Thr
    1055                1060                1065

Gly His  Pro Gly Thr Val Gly  Pro Ala Gly Ile Arg  Gly Pro Gln
    1070                1075                1080

Gly His  Gln Gly Pro Ala Gly  Pro Pro Gly Pro Pro  Gly Pro Pro
    1085                1090                1095

Gly Pro  Pro Gly Val Ser Gly  Gly Gly Tyr Asp Phe  Gly Tyr Asp
    1100                1105                1110

Gly Asp  Phe Tyr Arg Ala Asp  Gln Pro Arg Ser Ala  Pro Ser Leu
    1115                1120                1125

Arg Pro  Lys Asp Tyr Glu Val  Asp Ala Thr Leu Lys  Ser Leu Asn
    1130                1135                1140

Asn Gln  Ile Glu Thr Leu Leu  Thr Pro Glu Gly Ser  Arg Lys Asn
    1145                1150                1155

Pro Ala  Arg Thr Cys Arg Asp  Leu Arg Leu Ser His  Pro Glu Trp
    1160                1165                1170

Ser Ser  Gly Tyr Tyr Trp Ile  Asp Pro Asn Gln Gly  Cys Thr Met
    1175                1180                1185

Asp Ala  Ile Lys Val Tyr Cys  Asp Phe Ser Thr Gly  Glu Thr Cys
    1190                1195                1200

Ile Arg  Ala Gln Pro Glu Asn  Ile Pro Ala Lys Asn  Trp Tyr Arg
    1205                1210                1215

Ser Ser  Lys Asp Lys Lys His  Val Trp Leu Gly Glu  Thr Ile Asn
    1220                1225                1230

Ala Gly  Ser Gln Phe Glu Tyr  Asn Val Glu Gly Val  Thr Ser Lys
    1235                1240                1245

Glu Met  Ala Thr Gln Leu Ala  Phe Met Arg Leu Leu  Ala Asn Tyr
    1250                1255                1260

Ala Ser  Gln Asn Ile Thr Tyr  His Cys Lys Asn Ser  Ile Ala Tyr
    1265                1270                1275

Met Asp  Glu Glu Thr Gly Asn  Leu Lys Lys Ala Val  Ile Leu Gln
    1280                1285                1290

Gly Ser  Asn Asp Val Glu Leu  Val Ala Glu Gly Asn  Ser Arg Phe
    1295                1300                1305

Thr Tyr  Thr Val Leu Val Asp  Gly Cys Ser Lys Lys  Thr Asn Glu
    1310                1315                1320

Trp Gly  Lys Thr Ile Ile Glu  Tyr Lys Thr Asn Lys  Pro Ser Arg
```

```
                1325                1330                1335
Leu Pro Phe Leu Asp Ile Ala Pro Leu Asp Ile Gly Gly Ala Asp
    1340                1345                1350

Gln Glu Phe Phe Val Asp Ile Gly Pro Val Cys Phe Lys
    1355                1360                1365

<210> SEQ ID NO 4
<211> LENGTH: 4101
<212> TYPE: DNA
<213> ORGANISM: Homo sapiens

<400> SEQUENCE: 4
```

| | | | | | |
|---|---|---|---|---|---|
| atgctcagct | tgtggatac | gcggactttg | ttgctgcttg | cagtaacctt | atgcctagca | 60 |
| acatgccaat | ctttacaaga | ggaaactgta | agaaagggcc | cagccggaga | tagaggacca | 120 |
| cgtggagaaa | ggggtccacc | aggcccccca | ggcagagatg | gtgaagatgg | tcccacaggc | 180 |
| cctcctggtc | cacctggtcc | tcctggcccc | ctggtctcg | gtgggaactt | tgctgctcag | 240 |
| tatgatggaa | aaggagttgg | acttggccct | ggaccaatgg | gcttaatggg | acctagaggc | 300 |
| ccacctggtg | cagctggagc | cccaggccct | caaggtttcc | aaggacctgc | tggtgagcct | 360 |
| ggtgaacctg | gtcaaactgg | tcctgcaggt | gctcgtggtc | cagctggccc | tcctggcaag | 420 |
| gctggtgaag | atggtcaccc | tggaaaaccc | ggacgacctg | gtgagagagg | agttgttgga | 480 |
| ccacagggtg | ctcgtggttt | ccctggaact | cctggacttc | ctggcttcaa | aggcattagg | 540 |
| ggacacaatg | gtctggatgg | attgaaggga | cagcccggtg | ctcctggtgt | gaagggtgaa | 600 |
| cctggtgccc | ctggtgaaaa | tggaactcca | ggtcaaacag | gagcccgtgg | gcttcctggt | 660 |
| gagagaggac | gtgttggtgc | cctggcccca | gctggtgccc | gtggcagtga | tggaagtgtg | 720 |
| ggtcccgtgg | gtcctgctgg | tcccattggg | tctgctggcc | ctccaggctt | cccaggtgcc | 780 |
| cctggcccca | agggtgaaat | tggagctgtt | ggtaacgctg | gtcctgctgg | tcccgccggt | 840 |
| ccccgtggtg | aagtgggtct | tccaggcctc | tccggccccg | ttggacctcc | tggtaatcct | 900 |
| ggagcaaacg | gccttactgg | tgccaagggt | gctgctggcc | ttcccggcgt | gctgggggct | 960 |
| cccggcctcc | ctggacccg | cggtattcct | ggccctgttg | gtgctgccgg | tgctactggt | 1020 |
| gccagaggac | ttgttggtga | gcctggtcca | gctggctcca | aggagagag | cggtaacaag | 1080 |
| ggtgagcccg | gtctctggg | gccccaaggt | cctcctggtc | ccagtggtga | agaaggaaag | 1140 |
| agaggcccta | atggggaagc | tggatctgcc | ggccctccag | gacctcctgg | gctgagaggt | 1200 |
| agtcctggtt | tcgtggtct | tcctggagct | gatggcagag | ctggcgtcat | gggccctcct | 1260 |
| ggtagtcgtg | gtgcaagtgg | ccctgctgga | gtccgaggac | ctaatggaga | tgctggtcgc | 1320 |
| cctggggagc | ctggtctcat | gggacccaga | ggtcttcctg | gttcccctgg | aaatatcggc | 1380 |
| cccgctggaa | agaaggtcc | tgtcggcctc | cctggcatcg | acggcaggcc | tggcccaatt | 1440 |
| ggcccagctg | gagcaagagg | agagcctggc | aacattggat | ccctggacc | caaaggcccc | 1500 |
| actggtgatc | ctggcaaaaa | cggtgataaa | ggtcatgctg | gtcttgctgg | tgctcggggt | 1560 |
| gctccaggtc | ctgatggaaa | caatggtgct | cagggacctc | ctggaccaca | gggtgttcaa | 1620 |
| ggtgaaaag | gtgaacaggg | tcccctggt | cctccaggct | ccagggtct | gcctggcccc | 1680 |
| tcaggtcccg | ctggtgaagt | tggcaaacca | ggagaaaggg | gtctccatgg | tgagtttggt | 1740 |
| ctccctggtc | ctgctggtcc | aagagggaa | cgcggtcccc | caggtgagag | tggtgctgcc | 1800 |
| ggtcctactg | gtcctattgg | aagccgaggt | ccttctggac | cccagggcc | tgatggaaac | 1860 |
| aagggtgaac | ctggtgtggt | tggtgctgtg | ggcactgctg | gtccatctgg | tcctagtgga | 1920 |

```
ctcccaggag agaggggtgc tgctggcata cctggaggca agggagaaaa gggtgaacct    1980
ggtctcagag gtgaaattgg taaccctggc agagatggtg ctcgtggtgc tcctggtgct    2040
gtaggtgccc ctggtcctgc tggagccaca ggtgaccggg gcgaagctgg ggctgctggt    2100
cctgctggtc ctgctggtcc tcggggaagc cctggtgaac gtggtgaggt cggtcctgct    2160
ggccccaatg gatttgctgg tcctgctggt gctgctggtc aacctggtgc taaaggagaa    2220
agaggagcca aagggcctaa gggtgaaaac ggtgttgttg gtcccacagg ccccgttgga    2280
gctgctggcc cagctggtcc aaatggtccc cccggtcctg ctggaagtcg tggtgatgga    2340
ggccccctg gtatgactgg tttccctggt gctgctggac ggactggtcc cccaggaccc    2400
tctggtattt ctggccctcc tggtcccccct ggtcctgctg ggaagaagg gcttcgtggt    2460
cctcgtggtg accaaggtcc agttggccga actggagaag taggtgcagt tggtccccct    2520
ggcttcgctg gtgagaaggg tccctctgga gaggctggta ctgctggacc tcctggcact    2580
ccaggtcctc agggtcttct tggtgctcct ggtattctgg gtctccctgg ctcgagaggt    2640
gaacgtggtc taccaggtgt tgctggtgct gtgggtgaac ctggtcctct ggcattgcc    2700
ggccctcctg gggcccgtgg tcctcctggt gctgtgggta gtcctggagt caacggtgct    2760
cctggtgaag ctggtcgtga tggcaaccct gggaacgatg gtccccccagg tcgcgatggt    2820
caacccggac acaagggaga gcgcggttac cctggcaata ttggtcccgt tggtgctgca    2880
ggtgcacctg gtcctcatgg ccccgtgggt cctgctggca acatggaaa ccgtggtgaa    2940
actggtcctt ctggtcctgt tggtcctgct ggtgctgttg gcccaagagg tcctagtggc    3000
ccacaaggca ttcgtggcga taagggagag cccggtgaaa agggcccag aggtcttcct    3060
ggcttaaagg gacacaatgg gattgcaaggt ctgcctggta tcgctggtca ccatggtgat    3120
caaggtgctc ctggctccgt gggtcctgct ggtcctaggg gccctgctgg tccttctggc    3180
cctgctggaa aagatggtcg cactggacat cctggtacag ttggacctgc tggcattcga    3240
ggccctcagg gtcaccaagg ccctgctggc ccccctggtc cccctggccc tcctggacct    3300
ccaggtgtaa gcggtggtgg ttatgactt ggttacgatg gagacttcta cagggctgac    3360
cagcctcgct cagcaccttc tctcagaccc aaggactatg aagttgatgc tactctgaag    3420
tctctcaaca accagattga dacccttctt actcctgaag ctctagaaaa gaacccagct    3480
cgcacatgcc gtgacttgag actcagccac ccagagtgga gcagtggtta ctactggatt    3540
gaccctaacc aaggatgcac tatggatgct atcaaagtat actgtgatt ctctactggc    3600
gaaacctgta tccgggccca acctgaaaac atcccagcca agaactggta taggagctcc    3660
aaggacaaga aacacgtctg gctaggagaa actatcaatg ctggcagcca gtttgaatat    3720
aatgtagaag gagtgacttc caaggaaatg gctacccaac ttgccttcat cgcctgctg    3780
gccaactatg cctctcagaa catcacctac cactgcaaga acagcattgc atacatggat    3840
gaggagactg caacctgaa aaaggctgtc attctacagg gctctaatga tgttgaactt    3900
gttgctgagg gcaacagcag gttcacttac actgttcttg tagatggctg ctctaaaaag    3960
acaaatgaat ggggaaagac aatcattgaa tacaaaacaa ataagccatc acgcctgccc    4020
ttccttgata ttgcaccttt ggacatcggg ggtgctgacc aggaattctt tgtggacatt    4080
ggcccagtct gtttcaaata a                                             4101
```

<210> SEQ ID NO 5
<211> LENGTH: 951
<212> TYPE: PRT

<213> ORGANISM: Homo sapiens

<400> SEQUENCE: 5

```
Met Ser Arg Gly Gly Ser Tyr Pro His Leu Leu Trp Asp Val Arg Lys
1               5                   10                  15

Arg Ser Leu Gly Leu Glu Asp Pro Ser Arg Leu Arg Ser Arg Tyr Leu
            20                  25                  30

Gly Arg Arg Glu Phe Ile Gln Arg Leu Lys Leu Glu Ala Thr Leu Asn
        35                  40                  45

Val His Asp Gly Cys Val Asn Thr Ile Cys Trp Asn Asp Thr Gly Glu
    50                  55                  60

Tyr Ile Leu Ser Gly Ser Asp Asp Thr Lys Leu Val Ile Ser Asn Pro
65                  70                  75                  80

Tyr Ser Arg Lys Val Leu Thr Thr Ile Arg Ser Gly His Arg Ala Asn
                85                  90                  95

Ile Phe Ser Ala Lys Phe Leu Pro Cys Thr Asn Asp Lys Gln Ile Val
            100                 105                 110

Ser Cys Ser Gly Asp Gly Val Ile Phe Tyr Thr Asn Val Glu Gln Asp
        115                 120                 125

Ala Glu Thr Asn Arg Gln Cys Gln Phe Thr Cys His Tyr Gly Thr Thr
    130                 135                 140

Tyr Glu Ile Met Thr Val Pro Asn Asp Pro Tyr Thr Phe Leu Ser Cys
145                 150                 155                 160

Gly Glu Asp Gly Thr Val Arg Trp Phe Asp Thr Arg Ile Lys Thr Ser
                165                 170                 175

Cys Thr Lys Glu Asp Cys Lys Asp Ile Leu Ile Asn Cys Arg Arg
            180                 185                 190

Ala Ala Thr Ser Val Ala Ile Cys Pro Pro Ile Pro Tyr Tyr Leu Ala
        195                 200                 205

Val Gly Cys Ser Asp Ser Ser Val Arg Ile Tyr Asp Arg Arg Met Leu
    210                 215                 220

Gly Thr Arg Ala Thr Gly Asn Tyr Ala Gly Arg Gly Thr Thr Gly Met
225                 230                 235                 240

Val Ala Arg Phe Ile Pro Ser His Leu Asn Asn Lys Ser Cys Arg Val
                245                 250                 255

Thr Ser Leu Cys Tyr Ser Glu Asp Gly Gln Glu Ile Leu Val Ser Tyr
            260                 265                 270

Ser Ser Asp Tyr Ile Tyr Leu Phe Asp Pro Lys Asp Asp Thr Ala Arg
        275                 280                 285

Glu Leu Lys Thr Pro Ser Ala Glu Glu Arg Arg Glu Glu Leu Arg Gln
    290                 295                 300

Pro Pro Val Lys Arg Leu Arg Leu Arg Gly Asp Trp Ser Asp Thr Gly
305                 310                 315                 320

Pro Arg Ala Arg Pro Glu Ser Glu Arg Glu Arg Asp Gly Glu Gln Ser
                325                 330                 335

Pro Asn Val Ser Leu Met Gln Arg Met Ser Asp Met Leu Ser Arg Trp
            340                 345                 350

Phe Glu Glu Ala Ser Glu Val Ala Gln Ser Asn Arg Gly Arg Gly Arg
        355                 360                 365

Ser Arg Pro Arg Gly Gly Thr Ser Gln Ser Asp Ile Ser Thr Leu Pro
    370                 375                 380

Thr Val Pro Ser Ser Pro Asp Leu Glu Val Ser Glu Thr Ala Met Glu
385                 390                 395                 400
```

Val Asp Thr Pro Ala Glu Gln Phe Leu Gln Pro Ser Thr Ser Ser Thr
            405                 410                 415

Met Ser Ala Gln Ala His Ser Thr Ser Ser Pro Thr Glu Ser Pro His
            420                 425                 430

Ser Thr Pro Leu Leu Ser Ser Pro Asp Ser Glu Gln Arg Gln Ser Val
            435                 440                 445

Glu Ala Ser Gly His His Thr His His Gln Ser Glu Phe Leu Arg Gly
450                 455                 460

Pro Glu Ile Ala Leu Leu Arg Lys Arg Leu Gln Gln Leu Arg Leu Lys
465                 470                 475                 480

Lys Ala Glu Gln Gln Arg Gln Gln Leu Ala Ala His Thr Gln Gln
                485                 490                 495

Gln Pro Ser Thr Ser Asp Gln Ser Ser His Glu Gly Ser Ser Gln Asp
            500                 505                 510

Pro His Ala Ser Asp Ser Pro Ser Ser Val Val Asn Lys Gln Leu Gly
            515                 520                 525

Ser Met Ser Leu Asp Glu Gln Gln Asp Asn Asn Asn Glu Lys Leu Ser
            530                 535                 540

Pro Lys Pro Gly Thr Gly Glu Pro Val Leu Ser Leu His Tyr Ser Thr
545                 550                 555                 560

Glu Gly Thr Thr Thr Ser Thr Ile Lys Leu Asn Phe Thr Asp Glu Trp
                565                 570                 575

Ser Ser Ile Ala Ser Ser Ser Arg Gly Ile Gly Ser His Cys Lys Ser
            580                 585                 590

Glu Gly Gln Glu Glu Ser Phe Val Pro Gln Ser Ser Val Gln Pro Pro
            595                 600                 605

Glu Gly Asp Ser Glu Thr Lys Ala Pro Glu Glu Ser Ser Glu Asp Val
            610                 615                 620

Thr Lys Tyr Gln Glu Gly Val Ser Ala Glu Asn Pro Val Glu Asn His
625                 630                 635                 640

Ile Asn Ile Thr Gln Ser Asp Lys Phe Thr Ala Lys Pro Leu Asp Ser
                645                 650                 655

Asn Ser Gly Glu Arg Asn Asp Leu Asn Leu Asp Arg Ser Cys Gly Val
            660                 665                 670

Pro Glu Glu Ser Ala Ser Ser Glu Lys Ala Lys Glu Pro Glu Thr Ser
            675                 680                 685

Asp Gln Thr Ser Thr Glu Ser Ala Thr Asn Glu Asn Asn Thr Asn Pro
            690                 695                 700

Glu Pro Gln Phe Gln Thr Glu Ala Thr Gly Pro Ser Ala His Glu Glu
705                 710                 715                 720

Thr Ser Thr Arg Asp Ser Ala Leu Gln Asp Thr Asp Asp Ser Asp Asp
                725                 730                 735

Asp Pro Val Leu Ile Pro Gly Ala Arg Tyr Arg Ala Gly Pro Gly Asp
            740                 745                 750

Arg Phe Asn Ile Arg Gly Thr Thr Ile Gly Asp Arg Ile Met Arg Arg
            755                 760                 765

Ser Ala Val Ala Arg Ile Gln Glu Phe Phe Arg Arg Lys Glu Arg
            770                 775                 780

Lys Glu Met Glu Glu Leu Asp Thr Leu Asn Ile Arg Arg Pro Leu Val
785                 790                 795                 800

Lys Met Val Tyr Lys Gly His Arg Asn Ser Arg Thr Met Ile Lys Glu
                805                 810                 815

Ala Asn Phe Trp Gly Ala Asn Phe Val Met Ser Gly Ser Asp Cys Gly

```
                    820             825             830
His Ile Phe Ile Trp Asp Arg His Thr Ala Glu His Leu Met Leu Leu
                835             840             845

Glu Ala Asp Asn His Val Val Asn Cys Leu Gln Pro His Pro Phe Asp
850             855             860

Pro Ile Leu Ala Ser Ser Gly Ile Asp Tyr Asp Ile Lys Ile Trp Ser
865             870             875             880

Pro Leu Glu Glu Ser Arg Ile Phe Asn Arg Lys Leu Ala Asp Glu Val
                885             890             895

Ile Thr Arg Asn Glu Leu Met Leu Glu Glu Thr Arg Asn Thr Ile Thr
                900             905             910

Val Pro Ala Ser Phe Met Leu Arg Met Leu Ala Ser Leu Asn His Ile
            915             920             925

Arg Ala Asp Arg Leu Glu Gly Asp Arg Ser Glu Gly Ser Gly Gln Glu
            930             935             940

Asn Glu Asn Glu Asp Glu Glu
945                 950

<210> SEQ ID NO 6
<211> LENGTH: 2856
<212> TYPE: DNA
<213> ORGANISM: Homo sapiens

<400> SEQUENCE: 6
```

| | | | | | |
|---|---|---|---|---|---|
| atgtctcggg | gtggctccta | cccacacctg | ttgtgggacg | tgaggaaaag | gtccctcggg | 60 |
| ctggaggacc | cgtcccggct | gcggagtcgc | tacctgggaa | gagagaatt | tatccaaaga | 120 |
| ttaaaacttg | aagcaaccct | taatgtgcat | gatggttgtg | ttaatacaat | ctgttggaat | 180 |
| gacactggag | aatatatttt | atctggctca | gatgacacca | aattagtaat | tagtaatcct | 240 |
| tacagcagaa | aggttttgac | aacaattcgt | tcagggcacc | gagcaaacat | atttagtgca | 300 |
| aagttcttac | cttgtacaaa | tgataaacag | attgtatcct | gctctggaga | tggagtaata | 360 |
| tttatacca | acgttgagca | agatgcagaa | accaacagac | aatgccaatt | tacgtgtcat | 420 |
| tatggaacta | cttatgagat | tatgactgta | cccaatgacc | cttacacttt | tctctcttgt | 480 |
| ggtgaagatg | gaactgttag | gtggtttgat | acacgcatca | aaactagctg | cacaaaagaa | 540 |
| gattgtaaag | atgatatttt | aattaactgt | cgacgtgctg | ccacgtctgt | tgctatttgc | 600 |
| ccaccaatac | catattacct | tgctgttggt | tgttctgaca | gctcagtacg | aatatatgat | 660 |
| cggcgaatgc | tgggcacaag | agctacaggg | aattatgcag | gtcgagggac | tactggaatg | 720 |
| gttgcccgtt | ttattccttc | ccatcttaat | aataagtcct | gcagagtgac | atctctgtgt | 780 |
| tacagtgaag | atggtcaaga | gattctcgtt | agttactctt | cagattacat | atatcttttt | 840 |
| gacccgaaag | atgatacagc | acgagaactt | aaaactcctt | ctgcggaaga | gagaagagaa | 900 |
| gagttgcgac | aaccaccagt | taagcgtttg | agacttcgtg | gtgattggtc | agatactgga | 960 |
| cccagagcaa | ggccggagag | tgaacgagaa | cgagatggag | agcagagtcc | caatgtgtca | 1020 |
| ttgatgcaga | gaatgtctga | tatgttatca | agatggtttg | aagaagcaag | tgaggttgca | 1080 |
| caaagcaata | gaggacgagg | aagatctcga | cccagaggtg | gaacaagtca | atcagatatt | 1140 |
| tcaactcttc | ctacggtccc | atcaagtcct | gatttggaag | tgagtgaaac | tgcaatggaa | 1200 |
| gtagatactc | cagctgaaca | atttcttcag | ccttctacat | cctctacaat | gtcagctcag | 1260 |
| gctcattcga | catcatctcc | cacagaaagc | cctcattcta | ctcctttgct | atcttctcca | 1320 |
| gacagtgaac | aaaggcagtc | tgttgaggca | tctggacacc | acacacatca | tcagtctgaa | 1380 |

```
tttttaaggg gccctgagat agctttgctt cgtaagcgcc tgcaacaact gaggcttaag   1440
aaggctgagc agcagaggca gcaagagcta gctgcacata cccagcaaca gccttccact   1500
tctgatcagt cttctcatga gggctcttca caggaccctc atgcttcaga ttctccttct   1560
tctgtggtta acaaacagct cggatccatg tcacttgacg agcaacagga taacaataat   1620
gaaaagctga gccccaaacc agggacaggt gaaccagttt taagtttgca ctacagcaca   1680
gaaggaacaa ctacaagcac aataaaactg aactttacag atgaatggag cagtatagca   1740
tcaagttcta gaggaattgg gagccattgc aaatctgagg gtcaggagga atctttcgtc   1800
ccacagagct cagtgcaacc accagaagga gacagtgaaa caaaagctcc tgaagaatca   1860
tcagaggatg tgacaaaata tcaggaagga gtatctgcag aaaacccagt tgagaaccat   1920
atcaatataa cacaatcaga taagttcaca gccaagccat ggattccaa ctcaggagaa   1980 agaaatgacc tcaatcttga tcgctcttgt ggggttccag aagaatctgc ttcatctgaa   2040
aaagccaagg aaccagaaac ttcagatcag actagcactg agagtgctac caatgaaaat   2100
aacaccaatc ctgagcctca gttccaaaca gaagccactg ggccttcagc tcatgaagaa   2160
acatccacca gggactctgc tcttcaggac acagatgaca gtgatgatga cccagtcctg   2220
atcccaggtg caaggtatcg agcaggacct ggtgatagat taatatcag aggaacaaca   2280 ataggtgata gaataatgag acgctctgct gttgcccgta ttcaggagtt cttcagacgg   2340
agaaaagaaa ggaaagaaat ggaagaattg gatactttga acattagaag gccgctagta   2400
aaaatggttt ataaaggcca tgcaactcc aggacaatga taaaagaagc caatttctgg   2460
ggtgctaact ttgtaatgag tggttctgac tgtggccaca ttttcatctg ggatcggcac   2520
actgctgagc atttgatgct tctggaagct gataatcatg tggtaaactg cctgcagcca   2580
catccgtttg acccaatttt agcctcatct ggcatagatt atgacataaa gatctggtca   2640
ccattagaag agtcaaggat ttttaaccga aaacttgctg atgaagttat aactcgaaac   2700
gaactcatgc tggaagaaac tagaaacacc attacagttc cagcctcttt catgttgagg   2760
atgttggctt cacttaatca tatccgagct gaccggttgg agggtgacag atcagaaggc   2820
tctggtcaag agaatgaaaa tgaggatgag gaataa                             2856
```

<210> SEQ ID NO 7
<211> LENGTH: 1100
<212> TYPE: PRT
<213> ORGANISM: Homo sapiens

<400> SEQUENCE: 7

```
Met Leu Ser Phe Val Asp Thr Arg Thr Leu Leu Leu Ala Val Thr
1               5                   10                  15

Leu Cys Leu Ala Thr Cys Gln Ser Leu Gln Glu Glu Thr Val Arg Lys
                20                  25                  30

Gly Pro Ala Gly Asp Arg Gly Pro Arg Gly Glu Arg Gly Pro Pro Gly
            35                  40                  45

Pro Pro Gly Arg Asp Gly Glu Asp Gly Pro Thr Gly Pro Pro Gly Pro
        50                  55                  60

Pro Gly Pro Pro Gly Pro Gly Leu Gly Gly Asn Phe Ala Ala Gln
65                  70                  75                  80

Tyr Asp Gly Lys Gly Val Gly Leu Gly Pro Gly Pro Met Gly Leu Met
                85                  90                  95

Gly Pro Arg Gly Pro Pro Gly Ala Ala Gly Ala Pro Gly Pro Gln Gly
            100                 105                 110
```

```
Phe Gln Gly Pro Ala Gly Glu Pro Gly Gln Thr Gly Pro
        115                 120                 125

Ala Gly Ala Arg Gly Pro Ala Gly Pro Pro Gly Lys Ala Gly Glu Asp
    130                 135                 140

Gly His Pro Gly Lys Pro Gly Arg Pro Gly Glu Arg Gly Val Val Gly
145                 150                 155                 160

Pro Gln Gly Ala Arg Gly Phe Pro Gly Thr Pro Gly Leu Pro Gly Phe
                165                 170                 175

Lys Gly Ile Arg Gly His Asn Gly Leu Asp Gly Leu Lys Gly Gln Pro
            180                 185                 190

Gly Ala Pro Gly Val Lys Gly Glu Pro Gly Ala Pro Gly Glu Asn Gly
        195                 200                 205

Thr Pro Gly Gln Thr Gly Ala Arg Gly Leu Pro Gly Glu Arg Gly Arg
    210                 215                 220

Val Gly Ala Pro Gly Pro Ala Gly Ala Arg Gly Ser Asp Gly Ser Val
225                 230                 235                 240

Gly Pro Val Gly Pro Ala Gly Pro Ile Gly Ser Ala Gly Pro Pro Gly
                245                 250                 255

Phe Pro Gly Ala Pro Gly Pro Lys Gly Glu Ile Gly Ala Val Gly Asn
                260                 265                 270

Ala Gly Pro Ala Gly Pro Ala Gly Pro Arg Gly Glu Val Gly Leu Pro
            275                 280                 285

Gly Leu Ser Gly Pro Val Gly Pro Pro Gly Asn Pro Gly Ala Asn Gly
        290                 295                 300

Leu Thr Gly Ala Lys Gly Ala Ala Gly Leu Pro Gly Val Ala Gly Ala
305                 310                 315                 320

Pro Gly Leu Pro Gly Pro Arg Gly Ile Pro Gly Pro Val Gly Ala Ala
                325                 330                 335

Gly Ala Thr Gly Ala Arg Gly Leu Val Gly Glu Pro Gly Pro Ala Gly
                340                 345                 350

Ser Lys Gly Glu Ser Gly Asn Lys Gly Glu Pro Gly Ser Ala Gly Pro
        355                 360                 365

Gln Gly Pro Pro Gly Pro Ser Gly Glu Glu Gly Lys Arg Gly Pro Asn
    370                 375                 380

Gly Glu Ala Gly Ser Ala Gly Pro Pro Gly Pro Pro Gly Leu Arg Gly
385                 390                 395                 400

Ser Pro Gly Ser Arg Gly Leu Pro Gly Ala Asp Gly Arg Ala Gly Val
                405                 410                 415

Met Gly Pro Pro Gly Ser Arg Gly Ala Ser Gly Pro Ala Gly Val Arg
                420                 425                 430

Gly Pro Asn Gly Asp Ala Gly Arg Pro Gly Glu Pro Gly Leu Met Gly
            435                 440                 445

Pro Arg Leu Arg Gln Pro Pro Val Lys Arg Leu Arg Leu Arg Gly Asp
        450                 455                 460

Trp Ser Asp Thr Gly Pro Arg Ala Arg Pro Glu Ser Glu Arg Glu Arg
465                 470                 475                 480

Asp Gly Glu Gln Ser Pro Asn Val Ser Leu Met Gln Arg Met Ser Asp
                485                 490                 495

Met Leu Ser Arg Trp Phe Glu Glu Ala Ser Glu Val Ala Gln Ser Asn
            500                 505                 510

Arg Gly Arg Gly Arg Ser Arg Pro Arg Gly Gly Thr Ser Gln Ser Asp
        515                 520                 525
```

```
Ile Ser Thr Leu Pro Thr Val Pro Ser Ser Pro Asp Leu Glu Val Ser
    530                 535                 540

Glu Thr Ala Met Glu Val Asp Thr Pro Ala Glu Gln Phe Leu Gln Pro
545                 550                 555                 560

Ser Thr Ser Ser Thr Met Ser Ala Gln Ala His Ser Thr Ser Ser Pro
            565                 570                 575

Thr Glu Ser Pro His Ser Thr Pro Leu Leu Ser Ser Pro Asp Ser Glu
        580                 585                 590

Gln Arg Gln Ser Val Glu Ala Ser Gly His His Thr His His Gln Ser
    595                 600                 605

Glu Phe Leu Arg Gly Pro Glu Ile Ala Leu Leu Arg Lys Arg Leu Gln
    610                 615                 620

Gln Leu Arg Leu Lys Lys Ala Glu Gln Gln Arg Gln Gln Glu Leu Ala
625                 630                 635                 640

Ala His Thr Gln Gln Gln Pro Ser Thr Ser Asp Gln Ser Ser His Glu
                645                 650                 655

Gly Ser Ser Gln Asp Pro His Ala Ser Asp Ser Pro Ser Ser Val Val
            660                 665                 670

Asn Lys Gln Leu Gly Ser Met Ser Leu Asp Glu Gln Gln Asp Asn Asn
        675                 680                 685

Asn Glu Lys Leu Ser Pro Lys Pro Gly Thr Gly Glu Pro Val Leu Ser
    690                 695                 700

Leu His Tyr Ser Thr Glu Gly Thr Thr Thr Ser Thr Ile Lys Leu Asn
705                 710                 715                 720

Phe Thr Asp Glu Trp Ser Ser Ile Ala Ser Ser Ser Arg Gly Ile Gly
                725                 730                 735

Ser His Cys Lys Ser Glu Gly Gln Glu Glu Ser Phe Val Pro Gln Ser
            740                 745                 750

Ser Val Gln Pro Pro Glu Gly Asp Ser Glu Thr Lys Ala Pro Glu Glu
        755                 760                 765

Ser Ser Glu Asp Val Thr Lys Tyr Gln Glu Gly Val Ser Ala Glu Asn
    770                 775                 780

Pro Val Glu Asn His Ile Asn Ile Thr Gln Ser Asp Lys Phe Thr Ala
785                 790                 795                 800

Lys Pro Leu Asp Ser Asn Ser Gly Glu Arg Asn Asp Leu Asn Leu Asp
                805                 810                 815

Arg Ser Cys Gly Val Pro Glu Glu Ser Ala Ser Ser Glu Lys Ala Lys
            820                 825                 830

Glu Pro Glu Thr Ser Asp Gln Thr Ser Thr Glu Ser Ala Thr Asn Glu
        835                 840                 845

Asn Asn Thr Asn Pro Glu Pro Gln Phe Gln Thr Glu Ala Thr Gly Pro
    850                 855                 860

Ser Ala His Glu Glu Thr Ser Thr Arg Asp Ser Ala Leu Gln Asp Thr
865                 870                 875                 880

Asp Asp Ser Asp Asp Pro Val Leu Ile Pro Gly Ala Arg Tyr Arg
                885                 890                 895

Ala Gly Pro Gly Asp Arg Phe Asn Ile Arg Gly Thr Thr Ile Gly Asp
                900                 905                 910

Arg Ile Met Arg Arg Ser Ala Val Ala Arg Ile Gln Glu Phe Phe Arg
        915                 920                 925

Arg Arg Lys Glu Arg Lys Glu Met Glu Glu Leu Asp Thr Leu Asn Ile
    930                 935                 940

Arg Arg Pro Leu Val Lys Met Val Tyr Lys Gly His Arg Asn Ser Arg
```

```
                945              950              955              960
       Thr Met Ile Lys Glu Ala Asn Phe Trp Gly Ala Asn Phe Val Met Ser
                        965              970              975
       Gly Ser Asp Cys Gly His Ile Phe Ile Trp Asp Arg His Thr Ala Glu
                        980              985              990
       His Leu Met Leu Leu Glu Ala Asp  Asn His Val Val Asn Cys Leu Gln
                        995             1000             1005
       Pro His  Pro Phe Asp Pro Ile  Leu Ala Ser Ser Gly  Ile Asp Tyr
           1010             1015                 1020
       Asp Ile  Lys Ile Trp Ser Pro  Leu Glu Glu Ser Arg  Ile Phe Asn
           1025             1030                 1035
       Arg Lys  Leu Ala Asp Glu Val  Ile Thr Arg Asn Glu  Leu Met Leu
           1040             1045                 1050
       Glu Glu  Thr Arg Asn Thr Ile  Thr Val Pro Ala Ser  Phe Met Leu
           1055             1060                 1065
       Arg Met  Leu Ala Ser Leu Asn  His Ile Arg Ala Asp  Arg Leu Glu
           1070             1075                 1080
       Gly Asp  Arg Ser Glu Gly Ser  Gly Gln Glu Asn Glu  Asn Glu Asp
           1085             1090                 1095
       Glu Glu
           1100

<210> SEQ ID NO 8
<211> LENGTH: 3303
<212> TYPE: DNA
<213> ORGANISM: Homo sapiens

<400> SEQUENCE: 8
atgctcagct tgtgggatac gcggactttg ttgctgcttg cagtaacctt atgcctagca      60
acatgccaat ctttacaaga ggaaactgta agaaagggcc cagccggaga tagaggacca     120
cgtggagaaa gggtccacc aggcccccca ggcagagatg gtgaagatgg tcccacaggc     180
cctcctggtc cacctggtcc tcctggcccc ctggtctcg gtgggaactt tgctgctcag     240
tatgatggaa aaggagttgg acttggccct ggaccaatgg gcttaatggg acctagaggc     300
ccacctggtg cagctggagc cccaggccct caaggtttcc aaggacctgc tggtgagcct     360
ggtgaacctg gtcaaactgg tcctgcaggt gctcgtggtc cagctggccc tcctggcaag     420
gctggtgaag atggtcaccc tggaaaaccc ggacgacctg gtgagagagg agttgttgga     480
ccacagggtc tcgtggtttt ccctggaact cctggacttc ctggcttcaa aggcattagg     540
ggacacaatg gtctggatgg attgaaggga cagcccggtg ctcctggtgt gaagggtgaa     600
cctggtgccc ctggtgaaaa tggaactcca ggtcaaacag gagcccgtgg gcttcctggt     660
gagagaggac gtgttggtgc ccctggccca gctggtgccc gtggcagtga tggaagtgtg     720
ggtcccgtgg gtcctgctgg tcccattggg tctgctggcc ctccaggctt cccaggtgcc     780
cctggccccca agggtgaaat tggagctgtt ggtaacgctg gtcctgctgg tcccgccggt     840
ccccgtggtg aagtgggtct tccaggcctc tccggccccg ttggacctcc tggtaatcct     900
ggagcaaacg gccttactgg tgccaagggg ctgctggcc ttccggcgt tgctgggct      960
cccggcctcc ctggacccccg cggtattcct ggccctgttg gtgctgccgg tgctactggt    1020
gccagaggac ttgttggtga gcctggtcca gctggctcca aggagagag cggtaacaag    1080
ggtgagcccg gtctgctggg gccccaaggt cctcctggtc ccagtggtga agaaggaaag    1140
agaggcccta atgggaagc tggatctgcc ggccctccag gacctcctgg gctgagaggt    1200
```

```
agtcctggtt ctcgtggtct tcctggagct gatggcagag ctggcgtcat gggccctcct    1260
ggtagtcgtg gtgcaagtgg ccctgctgga gtccgaggac ctaatggaga tgctggtcgc    1320
cctggggagc ctggtctcat gggacccaga ttgcgacaac caccagttaa gcgtttgaga    1380
cttcgtggtg attggtcaga tactggaccc agagcaaggc cggagagtga acgagaacga    1440
gatggagagc agagtcccaa tgtgtcattg atgcagagaa tgtctgatat gttatcaaga    1500
tggtttgaag aagcaagtga ggttgcacaa agcaatagag gacgaggaag atctcgaccc    1560
agaggtggaa caagtcaatc agatatttca actcttccta cggtcccatc aagtcctgat    1620
ttggaagtga gtgaaactgc aatggaagta gatactccag ctgaacaatt tcttcagcct    1680
tctacatcct ctacaatgtc agctcaggct cattcgacat catctcccac agaaagccct    1740
cattctactc ctttgctatc ttctccagac agtgaacaaa ggcagtctgt tgaggcatct    1800
ggacaccaca cacatcatca gtctgaattt ttaaggggcc ctgagatagc tttgcttcgt    1860
aagcgcctgc aacaactgag gcttaagaag gctgagcagc agaggcagca agagctagct    1920
gcacataccc agcaacagcc ttccacttct gatcagtctt ctcatgaggg ctcttcacag    1980
gaccctcatg cttcagattc tccttcttct gtggttaaca acagctcgg atccatgtca    2040 cttgacgagc aacaggataa caataatgaa aagctgagcc ccaaaccagg gacaggtgaa    2100
ccagttttaa gtttgcacta cagcacagaa ggaacaacta caagcacaat aaaactgaac    2160
tttacagatg aatggagcag tatagcatca agttctagag gaattgggag ccattgcaaa    2220
tctgagggtc aggaggaatc tttcgtccca cagagctcag tgcaaccacc agaaggagac    2280
agtgaaacaa aagctcctga agaatcatca gaggatgtga caaaatatca ggaaggagta    2340
tctgcagaaa acccagttga gaaccatatc aatataacac aatcagataa gttcacagcc    2400
aagccattgg attccaactc aggagaaaga atgacctca atcttgatcg ctcttgtggg    2460
gttccagaag aatctgcttc atctgaaaaa gccaaggaac cagaaacttc agatcagact    2520
agcactgaga gtgctaccaa tgaaaataac accaatcctg agcctcagtt ccaaacagaa    2580
gccactgggc cttcagctca tgaagaaaca tccaccaggg actctgctct tcaggacaca    2640
gatgacagtg atgatgaccc agtcctgatc ccaggtgcaa ggtatcgagc aggacctggt    2700
gatagattta atatcagagg aacaacaata ggtgatagaa taatgagacg ctctgctgtt    2760
gcccgtattc aggagttctt cagacggaga aagaaagga agaaatgga agaattggat    2820 actttgaaca ttagaaggcc gctagtaaaa atggtttata aaggccatcg caactccagg    2880
acaatgataa aagaagccaa tttctggggt gctaactttg taatgagtgg ttctgactgt    2940
ggccacattt tcatctggga tcggcacact gctgagcatt tgatgcttct ggaagctgat    3000
aatcatgtgg taaactgcct gcagccacat ccgtttgacc caattttagc ctcatctggc    3060
atagattatg acataaagat ctggtcacca ttagaagagt caaggatttt taaccgaaaa    3120
cttgctgatg aagttataac tcgaaacgaa ctcatgctgg aagaaactag aaacaccatt    3180
acagttccag cctctttcat gttgaggatg ttggcttcac ttaatcatat ccgagctgac    3240
cggttggagg gtgacagatc agaaggctct ggtcaagaga atgaaaatga ggatgaggaa    3300
taa                                                                  3303

<210> SEQ ID NO 9
<211> LENGTH: 60
<212> TYPE: DNA
<213> ORGANISM: Artificial
<220> FEATURE:
```

-continued

<223> OTHER INFORMATION: Synthetic

<400> SEQUENCE: 9
gatcactctc attgctatag gcagcgacta gtctacccct caacgagtcg gttcggttcg    60

<210> SEQ ID NO 10
<211> LENGTH: 24
<212> TYPE: DNA
<213> ORGANISM: Artificial
<220> FEATURE:
<223> OTHER INFORMATION: Primer

<400> SEQUENCE: 10
tggaaaggac cttacacagt cctg    24

<210> SEQ ID NO 11
<211> LENGTH: 24
<212> TYPE: DNA
<213> ORGANISM: Artificial
<220> FEATURE:
<223> OTHER INFORMATION: Primer

<400> SEQUENCE: 11
gactcgttga agggtagact agtc    24

<210> SEQ ID NO 12
<211> LENGTH: 26
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (11)..(16)
<223> OTHER INFORMATION: n is a, c, g, or t

<400> SEQUENCE: 12
ctagactgcc nnnnnnggat cactct    26

<210> SEQ ID NO 13
<211> LENGTH: 3418
<212> TYPE: PRT
<213> ORGANISM: Homo sapiens

<400> SEQUENCE: 13

Met Pro Ile Gly Ser Lys Glu Arg Pro Thr Phe Phe Glu Ile Phe Lys
1               5                   10                  15

Thr Arg Cys Asn Lys Ala Asp Leu Gly Pro Ile Ser Leu Asn Trp Phe
            20                  25                  30

Glu Glu Leu Ser Ser Glu Ala Pro Pro Tyr Asn Ser Glu Pro Ala Glu
        35                  40                  45

Glu Ser Glu His Lys Asn Asn Asn Tyr Glu Pro Asn Leu Phe Lys Thr
    50                  55                  60

Pro Gln Arg Lys Pro Ser Tyr Asn Gln Leu Ala Ser Thr Pro Ile Ile
65                  70                  75                  80

Phe Lys Glu Gln Gly Leu Thr Leu Pro Leu Tyr Gln Ser Pro Val Lys
                85                  90                  95

Glu Leu Asp Lys Phe Lys Leu Asp Leu Gly Arg Asn Val Pro Asn Ser
            100                 105                 110

Arg His Lys Ser Leu Arg Thr Val Lys Thr Lys Met Asp Gln Ala Asp
        115                 120                 125

Asp Val Ser Cys Pro Leu Leu Asn Ser Cys Leu Ser Glu Ser Pro Val

```
            130                 135                 140
Val Leu Gln Cys Thr His Val Thr Pro Gln Arg Asp Lys Ser Val Val
145                 150                 155                 160

Cys Gly Ser Leu Phe His Thr Pro Lys Phe Val Lys Gly Arg Gln Thr
                165                 170                 175

Pro Lys His Ile Ser Glu Ser Leu Gly Ala Glu Val Asp Pro Asp Met
                180                 185                 190

Ser Trp Ser Ser Ser Leu Ala Thr Pro Pro Thr Leu Ser Ser Thr Val
                195                 200                 205

Leu Ile Val Arg Asn Glu Glu Ala Ser Glu Thr Val Phe Pro His Asp
                210                 215                 220

Thr Thr Ala Asn Val Lys Ser Tyr Phe Ser Asn His Asp Glu Ser Leu
225                 230                 235                 240

Lys Lys Asn Asp Arg Phe Ile Ala Ser Val Thr Asp Ser Glu Asn Thr
                245                 250                 255

Asn Gln Arg Glu Ala Ala Ser His Gly Phe Gly Lys Thr Ser Gly Asn
                260                 265                 270

Ser Phe Lys Val Asn Ser Cys Lys Asp His Ile Gly Lys Ser Met Pro
                275                 280                 285

Asn Val Leu Glu Asp Glu Val Tyr Glu Thr Val Val Asp Thr Ser Glu
                290                 295                 300

Glu Asp Ser Phe Ser Leu Cys Phe Ser Lys Cys Arg Thr Lys Asn Leu
305                 310                 315                 320

Gln Lys Val Arg Thr Ser Lys Thr Arg Lys Lys Ile Phe His Glu Ala
                325                 330                 335

Asn Ala Asp Glu Cys Glu Lys Ser Lys Asn Gln Val Lys Glu Lys Tyr
                340                 345                 350

Ser Phe Val Ser Glu Val Glu Pro Asn Asp Thr Asp Pro Leu Asp Ser
                355                 360                 365

Asn Val Ala Asn Gln Lys Pro Phe Glu Ser Gly Ser Asp Lys Ile Ser
                370                 375                 380

Lys Glu Val Val Pro Ser Leu Ala Cys Glu Trp Ser Gln Leu Thr Leu
385                 390                 395                 400

Ser Gly Leu Asn Gly Ala Gln Met Glu Lys Ile Pro Leu Leu His Ile
                405                 410                 415

Ser Ser Cys Asp Gln Asn Ile Ser Glu Lys Asp Leu Leu Asp Thr Glu
                420                 425                 430

Asn Lys Arg Lys Lys Asp Phe Leu Thr Ser Glu Asn Ser Leu Pro Arg
                435                 440                 445

Ile Ser Ser Leu Pro Lys Ser Glu Lys Pro Leu Asn Glu Glu Thr Val
                450                 455                 460

Val Asn Lys Arg Asp Glu Glu Gln His Leu Glu Ser His Thr Asp Cys
465                 470                 475                 480

Ile Leu Ala Val Lys Gln Ala Ile Ser Gly Thr Ser Pro Val Ala Ser
                485                 490                 495

Ser Phe Gln Gly Ile Lys Lys Ser Ile Phe Arg Ile Arg Glu Ser Pro
                500                 505                 510

Lys Glu Thr Phe Asn Ala Ser Phe Ser Gly His Met Thr Asp Pro Asn
                515                 520                 525

Phe Lys Lys Glu Thr Glu Ala Ser Glu Ser Gly Leu Glu Ile His Thr
                530                 535                 540

Val Cys Ser Gln Lys Glu Asp Ser Leu Cys Pro Asn Leu Ile Asp Asn
545                 550                 555                 560
```

-continued

```
Gly Ser Trp Pro Ala Thr Thr Thr Gln Asn Ser Val Ala Leu Lys Asn
                565                 570                 575

Ala Gly Leu Ile Ser Thr Leu Lys Lys Lys Thr Asn Lys Phe Ile Tyr
            580                 585                 590

Ala Ile His Asp Glu Thr Ser Tyr Lys Gly Lys Lys Ile Pro Lys Asp
        595                 600                 605

Gln Lys Ser Glu Leu Ile Asn Cys Ser Ala Gln Phe Glu Ala Asn Ala
    610                 615                 620

Phe Glu Ala Pro Leu Thr Phe Ala Asn Ala Asp Ser Gly Leu Leu His
625                 630                 635                 640

Ser Ser Val Lys Arg Ser Cys Ser Gln Asn Asp Ser Glu Glu Pro Thr
                645                 650                 655

Leu Ser Leu Thr Ser Ser Phe Gly Thr Ile Leu Arg Lys Cys Ser Arg
            660                 665                 670

Asn Glu Thr Cys Ser Asn Asn Thr Val Ile Ser Gln Asp Leu Asp Tyr
        675                 680                 685

Lys Glu Ala Lys Cys Asn Lys Glu Lys Leu Gln Leu Phe Ile Thr Pro
    690                 695                 700

Glu Ala Asp Ser Leu Ser Cys Leu Gln Glu Gly Gln Cys Glu Asn Asp
705                 710                 715                 720

Pro Lys Ser Lys Val Ser Asp Ile Lys Glu Val Leu Ala Ala
                725                 730                 735

Ala Cys His Pro Val Gln His Ser Lys Val Glu Tyr Ser Asp Thr Asp
            740                 745                 750

Phe Gln Ser Gln Lys Ser Leu Leu Tyr Asp His Glu Asn Ala Ser Thr
        755                 760                 765

Leu Ile Leu Thr Pro Thr Ser Lys Asp Val Leu Ser Asn Leu Val Met
    770                 775                 780

Ile Ser Arg Gly Lys Glu Ser Tyr Lys Met Ser Asp Lys Leu Lys Gly
785                 790                 795                 800

Asn Asn Tyr Glu Ser Asp Val Glu Leu Thr Lys Asn Ile Pro Met Glu
                805                 810                 815

Lys Asn Gln Asp Val Cys Ala Leu Asn Glu Asn Tyr Lys Asn Val Glu
            820                 825                 830

Leu Leu Pro Pro Glu Lys Tyr Met Arg Val Ala Ser Pro Ser Arg Lys
        835                 840                 845

Val Gln Phe Asn Gln Asn Thr Asn Leu Arg Val Ile Gln Lys Asn Gln
    850                 855                 860

Glu Glu Thr Thr Ser Ile Ser Lys Ile Thr Val Asn Pro Asp Ser Glu
865                 870                 875                 880

Glu Leu Phe Ser Asp Asn Glu Asn Asn Phe Val Phe Gln Val Ala Asn
                885                 890                 895

Glu Arg Asn Asn Leu Ala Leu Gly Asn Thr Lys Glu Leu His Glu Thr
            900                 905                 910

Asp Leu Thr Cys Val Asn Glu Pro Ile Phe Lys Asn Ser Thr Met Val
        915                 920                 925

Leu Tyr Gly Asp Thr Gly Asp Lys Gln Ala Thr Gln Val Ser Ile Lys
    930                 935                 940

Lys Asp Leu Val Tyr Val Leu Ala Glu Glu Asn Lys Asn Ser Val Lys
945                 950                 955                 960

Gln His Ile Lys Met Thr Leu Gly Gln Asp Leu Lys Ser Asp Ile Ser
                965                 970                 975
```

```
Leu Asn Ile Asp Lys Ile Pro Glu Lys Asn Asn Asp Tyr Met Asn Lys
            980                 985                 990

Trp Ala Gly Leu Leu Gly Pro Ile Ser Asn His Ser Phe Gly Gly Ser
        995                 1000                1005

Phe Arg Thr Ala Ser Asn Lys Glu Ile Lys Leu Ser Glu His Asn
    1010                1015                1020

Ile Lys Lys Ser Lys Met Phe Phe Lys Asp Ile Glu Glu Gln Tyr
    1025                1030                1035

Pro Thr Ser Leu Ala Cys Val Glu Ile Val Asn Thr Leu Ala Leu
    1040                1045                1050

Asp Asn Gln Lys Lys Leu Ser Lys Pro Gln Ser Ile Asn Thr Val
    1055                1060                1065

Ser Ala His Leu Gln Ser Ser Val Val Val Ser Asp Cys Lys Asn
    1070                1075                1080

Ser His Ile Thr Pro Gln Met Leu Phe Ser Lys Gln Asp Phe Asn
    1085                1090                1095

Ser Asn His Asn Leu Thr Pro Ser Gln Lys Ala Glu Ile Thr Glu
    1100                1105                1110

Leu Ser Thr Ile Leu Glu Glu Ser Gly Ser Gln Phe Glu Phe Thr
    1115                1120                1125

Gln Phe Arg Lys Pro Ser Tyr Ile Leu Gln Lys Ser Thr Phe Glu
    1130                1135                1140

Val Pro Glu Asn Gln Met Thr Ile Leu Lys Thr Thr Ser Glu Glu
    1145                1150                1155

Cys Arg Asp Ala Asp Leu His Val Ile Met Asn Ala Pro Ser Ile
    1160                1165                1170

Gly Gln Val Asp Ser Ser Lys Gln Phe Glu Gly Thr Val Glu Ile
    1175                1180                1185

Lys Arg Lys Phe Ala Gly Leu Leu Lys Asn Asp Cys Asn Lys Ser
    1190                1195                1200

Ala Ser Gly Tyr Leu Thr Asp Glu Asn Glu Val Gly Phe Arg Gly
    1205                1210                1215

Phe Tyr Ser Ala His Gly Thr Lys Leu Asn Val Ser Thr Glu Ala
    1220                1225                1230

Leu Gln Lys Ala Val Lys Leu Phe Ser Asp Ile Glu Asn Ile Ser
    1235                1240                1245

Glu Glu Thr Ser Ala Glu Val His Pro Ile Ser Leu Ser Ser Ser
    1250                1255                1260

Lys Cys His Asp Ser Val Val Ser Met Phe Lys Ile Glu Asn His
    1265                1270                1275

Asn Asp Lys Thr Val Ser Glu Lys Asn Asn Lys Cys Gln Leu Ile
    1280                1285                1290

Leu Gln Asn Asn Ile Glu Met Thr Thr Gly Thr Phe Val Glu Glu
    1295                1300                1305

Ile Thr Glu Asn Tyr Lys Arg Asn Thr Glu Asn Glu Asp Asn Lys
    1310                1315                1320

Tyr Thr Ala Ala Ser Arg Asn Ser His Asn Leu Glu Phe Asp Gly
    1325                1330                1335

Ser Asp Ser Ser Lys Asn Asp Thr Val Cys Ile His Lys Asp Glu
    1340                1345                1350

Thr Asp Leu Leu Phe Thr Asp Gln His Asn Ile Cys Leu Lys Leu
    1355                1360                1365

Ser Gly Gln Phe Met Lys Glu Gly Asn Thr Gln Ile Lys Glu Asp
```

-continued

```
              1370                1375                1380
Leu Ser  Asp Leu Thr Phe Leu  Glu Val Ala Lys Ala  Gln Glu Ala
    1385                1390                1395

Cys His  Gly Asn Thr Ser Asn  Lys Glu Gln Leu Thr  Ala Thr Lys
    1400                1405                1410

Thr Glu  Gln Asn Ile Lys Asp  Phe Glu Thr Ser Asp  Thr Phe Phe
    1415                1420                1425

Gln Thr  Ala Ser Gly Lys Asn  Ile Ser Val Ala Lys  Glu Ser Phe
    1430                1435                1440

Asn Lys  Ile Val Asn Phe Phe  Asp Gln Lys Pro Glu  Glu Leu His
    1445                1450                1455

Asn Phe  Ser Leu Asn Ser Glu  Leu His Ser Asp Ile  Arg Lys Asn
    1460                1465                1470

Lys Met  Asp Ile Leu Ser Tyr  Glu Glu Thr Asp Ile  Val Lys His
    1475                1480                1485

Lys Ile  Leu Lys Glu Ser Val  Pro Val Gly Thr Gly  Asn Gln Leu
    1490                1495                1500

Val Thr  Phe Gln Gly Gln Pro  Glu Arg Asp Glu Lys  Ile Lys Glu
    1505                1510                1515

Pro Thr  Leu Leu Gly Phe His  Thr Ala Ser Gly Lys  Lys Val Lys
    1520                1525                1530

Ile Ala  Lys Glu Ser Leu Asp  Lys Val Lys Asn Leu  Phe Asp Glu
    1535                1540                1545

Lys Glu  Gln Gly Thr Ser Glu  Ile Thr Ser Phe Ser  His Gln Trp
    1550                1555                1560

Ala Lys  Thr Leu Lys Tyr Arg  Glu Ala Cys Lys Asp  Leu Glu Leu
    1565                1570                1575

Ala Cys  Glu Thr Ile Glu Ile  Thr Ala Ala Pro Lys  Cys Lys Glu
    1580                1585                1590

Met Gln  Asn Ser Leu Asn Asn  Asp Lys Asn Leu Val  Ser Ile Glu
    1595                1600                1605

Thr Val  Val Pro Pro Lys Leu  Leu Ser Asp Asn Leu  Cys Arg Gln
    1610                1615                1620

Thr Glu  Asn Leu Lys Thr Ser  Lys Ser Ile Phe Leu  Lys Val Lys
    1625                1630                1635

Val His  Glu Asn Val Glu Lys  Glu Thr Ala Lys Ser  Pro Ala Thr
    1640                1645                1650

Cys Tyr  Thr Asn Gln Ser Pro  Tyr Ser Val Ile Glu  Asn Ser Ala
    1655                1660                1665

Leu Ala  Phe Tyr Thr Ser Cys  Ser Arg Lys Thr Ser  Val Ser Gln
    1670                1675                1680

Thr Ser  Leu Leu Glu Ala Lys  Lys Trp Leu Arg Glu  Gly Ile Phe
    1685                1690                1695

Asp Gly  Gln Pro Glu Arg Ile  Asn Thr Ala Asp Tyr  Val Gly Asn
    1700                1705                1710

Tyr Leu  Tyr Glu Asn Asn Ser  Asn Ser Thr Ile Ala  Glu Asn Asp
    1715                1720                1725

Lys Asn  His Leu Ser Glu Lys  Gln Asp Thr Tyr Leu  Ser Asn Ser
    1730                1735                1740

Ser Met  Ser Asn Ser Tyr Ser  Tyr His Ser Asp Glu  Val Tyr Asn
    1745                1750                1755

Asp Ser  Gly Tyr Leu Ser Lys  Asn Lys Leu Asp Ser  Gly Ile Glu
    1760                1765                1770
```

-continued

Pro Val Leu Lys Asn Val Glu Asp Gln Lys Asn Thr Ser Phe Ser
1775              1780              1785

Lys Val Ile Ser Asn Val Lys Asp Ala Asn Ala Tyr Pro Gln Thr
1790              1795              1800

Val Asn Glu Asp Ile Cys Val Glu Glu Leu Val Thr Ser Ser Ser
1805              1810              1815

Pro Cys Lys Asn Lys Asn Ala Ala Ile Lys Leu Ser Ile Ser Asn
1820              1825              1830

Ser Asn Asn Phe Glu Val Gly Pro Pro Ala Phe Arg Ile Ala Ser
1835              1840              1845

Gly Lys Ile Val Cys Val Ser His Glu Thr Ile Lys Lys Val Lys
1850              1855              1860

Asp Ile Phe Thr Asp Ser Phe Ser Lys Val Ile Lys Glu Asn Asn
1865              1870              1875

Glu Asn Lys Ser Lys Ile Cys Gln Thr Lys Ile Met Ala Gly Cys
1880              1885              1890

Tyr Glu Ala Leu Asp Asp Ser Glu Asp Ile Leu His Asn Ser Leu
1895              1900              1905

Asp Asn Asp Glu Cys Ser Thr His Ser His Lys Val Phe Ala Asp
1910              1915              1920

Ile Gln Ser Glu Glu Ile Leu Gln His Asn Gln Asn Met Ser Gly
1925              1930              1935

Leu Glu Lys Val Ser Lys Ile Ser Pro Cys Asp Val Ser Leu Glu
1940              1945              1950

Thr Ser Asp Ile Cys Lys Cys Ser Ile Gly Lys Leu His Lys Ser
1955              1960              1965

Val Ser Ser Ala Asn Thr Cys Gly Ile Phe Ser Thr Ala Ser Gly
1970              1975              1980

Lys Ser Val Gln Val Ser Asp Ala Ser Leu Gln Asn Ala Arg Gln
1985              1990              1995

Val Phe Ser Glu Ile Glu Asp Ser Thr Lys Gln Val Phe Ser Lys
2000              2005              2010

Val Leu Phe Lys Ser Asn Glu His Ser Asp Gln Leu Thr Arg Glu
2015              2020              2025

Glu Asn Thr Ala Ile Arg Thr Pro Glu His Leu Ile Ser Gln Lys
2030              2035              2040

Gly Phe Ser Tyr Asn Val Val Asn Ser Ser Ala Phe Ser Gly Phe
2045              2050              2055

Ser Thr Ala Ser Gly Lys Gln Val Ser Ile Leu Glu Ser Ser Leu
2060              2065              2070

His Lys Val Lys Gly Val Leu Glu Glu Phe Asp Leu Ile Arg Thr
2075              2080              2085

Glu His Ser Leu His Tyr Ser Pro Thr Ser Arg Gln Asn Val Ser
2090              2095              2100

Lys Ile Leu Pro Arg Val Asp Lys Arg Asn Pro Glu His Cys Val
2105              2110              2115

Asn Ser Glu Met Glu Lys Thr Cys Ser Lys Glu Phe Lys Leu Ser
2120              2125              2130

Asn Asn Leu Asn Val Glu Gly Gly Ser Ser Glu Asn Asn His Ser
2135              2140              2145

Ile Lys Val Ser Pro Tyr Leu Ser Gln Phe Gln Gln Asp Lys Gln
2150              2155              2160

```
Gln Leu Val Leu Gly Thr Lys Val Ser Leu Val Glu Asn Ile His
    2165                2170                2175
Val Leu Gly Lys Glu Gln Ala Ser Pro Lys Asn Val Lys Met Glu
    2180                2185                2190
Ile Gly Lys Thr Glu Thr Phe Ser Asp Val Pro Val Lys Thr Asn
    2195                2200                2205
Ile Glu Val Cys Ser Thr Tyr Ser Lys Asp Ser Glu Asn Tyr Phe
    2210                2215                2220
Glu Thr Glu Ala Val Glu Ile Ala Lys Ala Phe Met Glu Asp Asp
    2225                2230                2235
Glu Leu Thr Asp Ser Lys Leu Pro Ser His Ala Thr His Ser Leu
    2240                2245                2250
Phe Thr Cys Pro Glu Asn Glu Glu Met Val Leu Ser Asn Ser Arg
    2255                2260                2265
Ile Gly Lys Arg Arg Gly Glu Pro Leu Ile Leu Val Gly Glu Pro
    2270                2275                2280
Ser Ile Lys Arg Asn Leu Leu Asn Glu Phe Asp Arg Ile Ile Glu
    2285                2290                2295
Asn Gln Glu Lys Ser Leu Lys Ala Ser Lys Ser Thr Pro Asp Gly
    2300                2305                2310
Thr Ile Lys Asp Arg Arg Leu Phe Met His His Val Ser Leu Glu
    2315                2320                2325
Pro Ile Thr Cys Val Pro Phe Arg Thr Thr Lys Glu Arg Gln Glu
    2330                2335                2340
Ile Gln Asn Pro Asn Phe Thr Ala Pro Gly Gln Glu Phe Leu Ser
    2345                2350                2355
Lys Ser His Leu Tyr Glu His Leu Thr Leu Glu Lys Ser Ser Ser
    2360                2365                2370
Asn Leu Ala Val Ser Gly His Pro Phe Tyr Gln Val Ser Ala Thr
    2375                2380                2385
Arg Asn Glu Lys Met Arg His Leu Ile Thr Thr Gly Arg Pro Thr
    2390                2395                2400
Lys Val Phe Val Pro Pro Phe Lys Thr Lys Ser His Phe His Arg
    2405                2410                2415
Val Glu Gln Cys Val Arg Asn Ile Asn Leu Glu Glu Asn Arg Gln
    2420                2425                2430
Lys Gln Asn Ile Asp Gly His Gly Ser Asp Asp Ser Lys Asn Lys
    2435                2440                2445
Ile Asn Asp Asn Glu Ile His Gln Phe Asn Lys Asn Asn Ser Asn
    2450                2455                2460
Gln Ala Ala Ala Val Thr Phe Thr Lys Cys Glu Glu Pro Leu
    2465                2470                2475
Asp Leu Ile Thr Ser Leu Gln Asn Ala Arg Asp Ile Gln Asp Met
    2480                2485                2490
Arg Ile Lys Lys Lys Gln Arg Gln Arg Val Phe Pro Gln Pro Gly
    2495                2500                2505
Ser Leu Tyr Leu Ala Lys Thr Ser Thr Leu Pro Arg Ile Ser Leu
    2510                2515                2520
Lys Ala Ala Val Gly Gly Gln Val Pro Ser Ala Cys Ser His Lys
    2525                2530                2535
Gln Leu Tyr Thr Tyr Gly Val Ser Lys His Cys Ile Lys Ile Asn
    2540                2545                2550
Ser Lys Asn Ala Glu Ser Phe Gln Phe His Thr Glu Asp Tyr Phe
```

|  |  | 2555 |  |  |  | 2560 |  |  |  | 2565 |  |
|---|---|---|---|---|---|---|---|---|---|---|---|

Gly Lys Glu Ser Leu Trp Thr Gly Lys Gly Ile Gln Leu Ala Asp
     2570                2575                2580

Gly Gly Trp Leu Ile Pro Ser Asn Asp Gly Lys Ala Gly Lys Glu
     2585                2590                2595

Glu Phe Tyr Arg Ala Leu Cys Asp Thr Pro Gly Val Asp Pro Lys
     2600                2605                2610

Leu Ile Ser Arg Ile Trp Val Tyr Asn His Tyr Arg Trp Ile Ile
     2615                2620                2625

Trp Lys Leu Ala Ala Met Glu Cys Ala Phe Pro Lys Glu Phe Ala
     2630                2635                2640

Asn Arg Cys Leu Ser Pro Glu Arg Val Leu Leu Gln Leu Lys Tyr
     2645                2650                2655

Arg Tyr Asp Thr Glu Ile Asp Arg Ser Arg Arg Ser Ala Ile Lys
     2660                2665                2670

Lys Ile Met Glu Arg Asp Asp Thr Ala Ala Lys Thr Leu Val Leu
     2675                2680                2685

Cys Val Ser Asp Ile Ile Ser Leu Ser Ala Asn Ile Ser Glu Thr
     2690                2695                2700

Ser Ser Asn Lys Thr Ser Ser Ala Asp Thr Gln Lys Val Ala Ile
     2705                2710                2715

Ile Glu Leu Thr Asp Gly Trp Tyr Ala Val Lys Ala Gln Leu Asp
     2720                2725                2730

Pro Pro Leu Leu Ala Val Leu Lys Asn Gly Arg Leu Thr Val Gly
     2735                2740                2745

Gln Lys Ile Ile Leu His Gly Ala Glu Leu Val Gly Ser Pro Asp
     2750                2755                2760

Ala Cys Thr Pro Leu Glu Ala Pro Glu Ser Leu Met Leu Lys Ile
     2765                2770                2775

Ser Ala Asn Ser Thr Arg Pro Ala Arg Trp Tyr Thr Lys Leu Gly
     2780                2785                2790

Phe Phe Pro Asp Pro Arg Pro Phe Pro Leu Pro Leu Ser Ser Leu
     2795                2800                2805

Phe Ser Asp Gly Gly Asn Val Gly Cys Val Asp Val Ile Ile Gln
     2810                2815                2820

Arg Ala Tyr Pro Ile Gln Trp Met Glu Lys Thr Ser Ser Gly Leu
     2825                2830                2835

Tyr Ile Phe Arg Asn Glu Arg Glu Glu Lys Glu Ala Ala Lys
     2840                2845                2850

Tyr Val Glu Ala Gln Gln Lys Arg Leu Glu Ala Leu Phe Thr Lys
     2855                2860                2865

Ile Gln Glu Glu Phe Glu Glu His Glu Glu Asn Thr Thr Lys Pro
     2870                2875                2880

Tyr Leu Pro Ser Arg Ala Leu Thr Arg Gln Gln Val Arg Ala Leu
     2885                2890                2895

Gln Asp Gly Ala Glu Leu Tyr Glu Ala Val Lys Asn Ala Ala Asp
     2900                2905                2910

Pro Ala Tyr Leu Glu Gly Tyr Phe Ser Glu Gln Leu Arg Ala
     2915                2920                2925

Leu Asn Asn His Arg Gln Met Leu Asn Asp Lys Lys Gln Ala Gln
     2930                2935                2940

Ile Gln Leu Glu Ile Arg Lys Ala Met Glu Ser Ala Glu Gln Lys
     2945                2950                2955

```
Glu Gln Gly Leu Ser Arg Asp Val Thr Thr Val Trp Lys Leu Arg
2960                2965                2970

Ile Val Ser Tyr Ser Lys Lys Glu Lys Asp Ser Val Ile Leu Ser
2975                2980                2985

Ile Trp Arg Pro Ser Ser Asp Leu Tyr Ser Leu Leu Thr Glu Gly
2990                2995                3000

Lys Arg Tyr Arg Ile Tyr His Leu Ala Thr Ser Lys Ser Lys Ser
3005                3010                3015

Lys Ser Glu Arg Ala Asn Ile Gln Leu Ala Ala Thr Lys Lys Thr
3020                3025                3030

Gln Tyr Gln Gln Leu Pro Val Ser Asp Glu Ile Leu Phe Gln Ile
3035                3040                3045

Tyr Gln Pro Arg Glu Pro Leu His Phe Ser Lys Phe Leu Asp Pro
3050                3055                3060

Asp Phe Gln Pro Ser Cys Ser Glu Val Asp Leu Ile Gly Phe Val
3065                3070                3075

Val Ser Val Val Lys Lys Thr Gly Leu Ala Pro Phe Val Tyr Leu
3080                3085                3090

Ser Asp Glu Cys Tyr Asn Leu Leu Ala Ile Lys Phe Trp Ile Asp
3095                3100                3105

Leu Asn Glu Asp Ile Ile Lys Pro His Met Leu Ile Ala Ala Ser
3110                3115                3120

Asn Leu Gln Trp Arg Pro Glu Ser Lys Ser Gly Leu Leu Thr Leu
3125                3130                3135

Phe Ala Gly Asp Phe Ser Val Phe Ser Ala Ser Pro Lys Glu Gly
3140                3145                3150

His Phe Gln Glu Thr Phe Asn Lys Met Lys Asn Thr Val Glu Asn
3155                3160                3165

Ile Asp Ile Leu Cys Asn Glu Ala Glu Asn Lys Leu Met His Ile
3170                3175                3180

Leu His Ala Asn Asp Pro Lys Trp Ser Thr Pro Thr Lys Asp Cys
3185                3190                3195

Thr Ser Gly Pro Tyr Thr Ala Gln Ile Ile Pro Gly Thr Gly Asn
3200                3205                3210

Lys Leu Leu Met Ser Ser Pro Asn Cys Glu Ile Tyr Tyr Gln Ser
3215                3220                3225

Pro Leu Ser Leu Cys Met Ala Lys Arg Lys Ser Val Ser Thr Pro
3230                3235                3240

Val Ser Ala Gln Met Thr Ser Lys Ser Cys Lys Gly Glu Lys Glu
3245                3250                3255

Ile Asp Asp Gln Lys Asn Cys Lys Lys Arg Arg Ala Leu Asp Phe
3260                3265                3270

Leu Ser Arg Leu Pro Leu Pro Pro Val Ser Pro Ile Cys Thr
3275                3280                3285

Phe Val Ser Pro Ala Ala Gln Lys Ala Phe Gln Pro Pro Arg Ser
3290                3295                3300

Cys Gly Thr Lys Tyr Glu Thr Pro Ile Lys Lys Lys Glu Leu Asn
3305                3310                3315

Ser Pro Gln Met Thr Pro Phe Lys Lys Phe Asn Glu Ile Ser Leu
3320                3325                3330

Leu Glu Ser Asn Ser Ile Ala Asp Glu Glu Leu Ala Leu Ile Asn
3335                3340                3345
```

| Thr | Gln | Ala | Leu | Leu | Ser | Gly | Ser | Thr | Gly | Glu | Lys | Gln | Phe | Ile |
|---|---|---|---|---|---|---|---|---|---|---|---|---|---|---|
| | 3350 | | | | 3355 | | | | | 3360 | | | | |

Ser Val Ser Glu Ser Thr Arg Thr Ala Pro Thr Ser Ser Glu Asp
    3365                3370                3375

Tyr Leu Arg Leu Lys Arg Arg Cys Thr Thr Ser Leu Ile Lys Glu
    3380                3385                3390

Gln Glu Ser Ser Gln Ala Ser Thr Glu Glu Cys Glu Lys Asn Lys
    3395                3400                3405

Gln Asp Thr Ile Thr Thr Lys Lys Tyr Ile
    3410                3415

<210> SEQ ID NO 14
<211> LENGTH: 10257
<212> TYPE: DNA
<213> ORGANISM: Homo sapiens

<400> SEQUENCE: 14

```
atgcctattg gatccaaaga gaggccaaca ttttttgaaa ttttttaagac acgctgcaac      60
aaagcagatt taggaccaat aagtcttaat tggtttgaag aactttcttc agaagctcca     120
ccctataatt ctgaacctgc agaagaatct gaacataaaa acaacaatta cgaaccaaac     180
ctatttaaaa ctccacaaag gaaaccatct tataatcagc tggcttcaac tccaataata     240
ttcaaagagc aagggctgac tctgccgctg taccaatctc ctgtaaaaga attagataaa     300
ttcaaattag acttaggaag gaatgttccc aatagtagac ataaaagtct tcgcacagtg     360
aaaactaaaa tggatcaagc agatgatgtt tcctgtccac ttctaaattc ttgtcttagt     420
gaaagtcctg ttgttctaca atgtacacat gtaacaccac aaagagataa gtcagtggta     480
tgtgggagtt tgtttcatac accaaagttt gtgaagggtc gtcagacacc aaaacatatt     540
tctgaaagtc taggagctga ggtggatcct gatatgtctt ggtcaagttc tttagctaca     600
ccacccaccc ttagttctac tgtgctcata gtcagaaatg aagaagcatc tgaaactgta     660
tttcctcatg atactactgc taatgtgaaa agctattttt ccaatcatga tgaaagtctg     720
aagaaaaatg atagatttat cgcttctgtg acagacagtg aaaacacaaa tcaaagagaa     780
gctgcaagtc atggatttgg aaaaacatca gggaattcat ttaaagtaaa tagctgcaaa     840
gaccacattg aaagtcaatg ccaaatgtc ctagaagatg aagtatatga aacagttgta     900
gatacctctg aagaagatag tttttcatta tgttttttcta aatgtagaac aaaaaatcta     960
caaaaagtaa gaactagcaa gactaggaaa aaattttcc atgaagcaaa cgctgatgaa    1020
tgtgaaaaat ctaaaaacca agtgaaagaa aatactcat ttgtatctga agtggaacca    1080
aatgatactg atccattaga ttcaaatgta gcaaatcaga agcctttga gagtggaagt    1140
gacaaaatct ccaaggaagt tgtaccgtct ttggcctgtg aatggtctca actaaccctt    1200
tcaggtctaa atggagccca gatggagaaa atacccctat gcatatttc ttcatgtgac    1260
caaaatattt cagaaaaaga cctattagac acagagaaca aagaaagaa agattttctt    1320
acttcagaga attctttgcc acgtatttct agcctaccaa aatcagagaa gccattaaat    1380
gaggaaacag tggtaaataa gagagatgaa gagcagcatc ttgaatctca tacagactgc    1440
attcttgcag taaagcaggc aatatctgga acttctccag tggcttcttc atttcagggt    1500
atcaaaaagt ctatattcag aataagagaa tcacctaaag agactttcaa tgcaagtttt    1560
tcaggtcata tgactgatcc aaactttaaa aagaaactg aagcctctga agtggactg    1620
gaaatacata ctgtttgctc acagaaggag gactccttat gtccaaattt aattgataat    1680
```

```
ggaagctggc cagccaccac cacacagaat tctgtagctt tgaagaatgc aggtttaata    1740
tccactttga aaaagaaaac aaataagttt atttatgcta tacatgatga aacatcttat    1800
aaaggaaaaa aaataccgaa agaccaaaaa tcagaactaa ttaactgttc agcccagttt    1860
gaagcaaatg cttttgaagc accacttaca tttgcaaatg ctgattcagg tttattgcat    1920
tcttctgtga aagaagctg ttcacagaat gattctgaag aaccaacttt gtccttaact     1980
agctcttttg ggacaattct gaggaaatgt tctagaaatg aaacatgttc taataataca    2040
gtaatctctc aggatcttga ttataaagaa gcaaaatgta ataaggaaaa actacagtta    2100
tttattaccc cagaagctga ttctctgtca tgcctgcagg aaggacagtg tgaaaatgat    2160
ccaaaaagca aaaaagtttc agatataaaa gaagaggtct tggctgcagc atgtcaccca    2220
gtacaacatt caaaagtgga atacagtgat actgactttc aatcccagaa aagtctttta    2280
tatgatcatg aaaatgccag cactcttatt ttaactccta cttccaagga tgttctgtca    2340
aacctagtca tgatttctag aggcaaagaa tcatacaaaa tgtcagacaa gcttaaaggt    2400
aacaattatg aatctgatgt tgaattaacc aaaaatattc ccatggaaaa gaatcaagat    2460
gtatgtgctt taaatgaaaa ttataaaaac gttgagctgt tgccacctga aaaatacatg    2520
agagtagcat caccttcaag aaaggtacaa ttcaaccaaa acacaaatct aagagtaatc    2580
caaaaaaatc aagaagaaac tacttcaatt tcaaaaataa ctgtcaatcc agactctgaa    2640
gaacttttct cagacaatga gaataatttt gtcttccaag tagctaatga aggaataat    2700 cttgctttag gaaatactaa ggaacttcat gaaacagact tgacttgtgt aaacgaaccc    2760
attttcaaga actctaccat ggttttatat ggagacacag gtgataaaca agcaacccaa    2820
gtgtcaatta aaaagatttt ggtttatgtt cttgcagagg agaacaaaaa tagtgtaaag    2880
cagcatataa aaatgactct aggtcaagat ttaaaatcgg acatctcctt gaatatagat    2940
aaaataccag aaaaaataa tgattacatg aacaaatggg caggactctt aggtccaatt    3000
tcaaatcaca gttttggagg tagcttcaga acagcttcaa ataaggaaat caagctctct    3060
gaacataaca ttaagaagag caaaatgttc ttcaaagata ttgaagaaca atatcctact    3120
agtttagctt gtgttgaaat tgtaaatacc ttggcattag ataatcaaaa gaaactgagc    3180
aagcctcagt caattaatac tgtatctgca catttacaga gtagtgtagt tgtttctgat    3240
tgtaaaaata gtcatataac ccctcagatg ttattttcca agcaggattt taattcaaac    3300
cataatttaa cacctagcca aaaggcagaa attacagaac tttctactat attagaagaa    3360
tcaggaagtc agtttgaatt tactcagttt agaaagccaa gctacatatt gcagaagagt    3420
acatttgaag tgcctgaaaa ccagatgact atcttaaaga ccacttctga ggaatgcaga    3480
gatgctgatc ttcatgtcat aatgaatgcc ccatcgattg gtcaggtaga cagcagcaag    3540
caatttgaag gtacagttga aattaaacgg aagtttgctg gcctgttgaa aaatgactgt    3600
aacaaaagtg cttctggtta tttaacagat gaaaatgaag tggggtttag ggcttttat     3660 tctgctcatg gcacaaaact gaatgtttct actgaagctc tgcaaaaagc tgtgaaactg    3720
tttagtgata ttgagaatat tagtgaggaa acttctgcag aggtacatcc aataagttta    3780
tcttcaagta atgtcatga ttctgttgtt tcaatgttta agatagaaaa tcataatgat     3840
aaaactgtaa gtgaaaaaaa taataaatgc caactgatat tacaaaataa tattgaaatg    3900
actactggca cttttgttga agaaattact gaaaattaca agagaaatac tgaaaatgaa    3960
gataacaaat atactgctgc cagtagaaat tctcataact tagaatttga tggcagtgat    4020
tcaagtaaaa atgatactgt ttgtattcat aaagatgaaa cggacttgct atttactgat    4080
```

```
cagcacaaca tatgtcttaa attatctggc cagtttatga aggagggaaa cactcagatt    4140
aaagaagatt tgtcagattt aacttttttg gaagttgcga aagctcaaga agcatgtcat    4200
ggtaatactt caaataaaga acagttaact gctactaaaa cggagcaaaa tataaaagat    4260
tttgagactt ctgatacatt ttttcagact gcaagtggga aaaatattag tgtcgccaaa    4320
gagtcattta ataaaattgt aaatttcttt gatcagaaac cagaagaatt gcataacttt    4380
tccttaaatt ctgaattaca ttctgacata agaaagaaca aaatggacat tctaagttat    4440
gaggaaacag acatagttaa acacaaaata ctgaaagaaa gtgtcccagt tggtactgga    4500
aatcaactag tgaccttcca gggacaaccc gaacgtgatg aaaagatcaa agaacctact    4560
ctgttgggtt ttcatacagc tagcgggaaa aaagttaaaa ttgcaaagga atctttggac    4620
aaagtgaaaa acctttttga tgaaaaagag caaggtacta gtgaaatcac cagttttagc    4680
catcaatggg caaagaccct aaagtacaga gaggcctgta aagaccttga attagcatgt    4740
gagaccattg agatcacagc tgccccaaag tgtaaagaaa tgcagaattc tctcaataat    4800
gataaaaacc ttgtttctat tgagactgtg gtgccaccta agctcttaag tgataattta    4860
tgtagacaaa ctgaaaatct caaaacatca aaaagtatct ttttgaaagt taaagtacat    4920
gaaaatgtag aaaagaaac agcaaaaagt cctgcaactt gttacacaaa tcagtcccct    4980
tattcagtca ttgaaaattc agccttagct ttttacacaa gttgtagtag aaaaacttct    5040
gtgagtcaga cttcattact tgaagcaaaa aaatggctta gagaaggaat atttgatggt    5100
caaccagaaa gaataaatac tgcagattat gtaggaaatt atttgtatga aataattca    5160 aacagtacta tagctgaaaa tgacaaaaat catctctccg aaaaacaaga tacttattta    5220
agtaacagta gcatgtctaa cagctattcc taccattctg atgaggtata taatgattca    5280
ggatatctct caaaaaataa acttgattct ggtattgagc cagtattgaa gaatgttgaa    5340
gatcaaaaaa acactagttt ttccaaagta atatccaatg taaaagatgc aaatgcatac    5400
ccacaaactg taaatgaaga tatttgcgtt gaggaacttg tgactagctc ttcaccctgc    5460
aaaaataaaa atgcagccat taaattgtcc atatctaata gtaataattt tgaggtaggg    5520
ccacctgcat ttaggatagc cagtggtaaa atcgtttgtg tttcacatga acaattaaa    5580 aaagtgaaag acatatttac agacagtttc agtaaagtaa ttaaggaaaa caacgagaat    5640
aaatcaaaaa tttgccaaac gaaaattatg gcaggttgtt acgaggcatt ggatgattca    5700
gaggatattc ttcataactc tctagataat gatgaatgta gcacgcattc acataaggtt    5760
tttgctgaca ttcagagtga agaaatttta caacataacc aaaatatgtc tggattggag    5820
aaagttccta aatatcacc ttgtgatgtt agtttggaaa cttcagatat atgtaaatgt    5880
agtataggga agcttcataa gtcagtctca tctgcaaata cttgtgggat ttttagcaca    5940
gcaagtggaa aatctgtcca ggtatcagat gcttcattac aaaacgcaag acaagtgttt    6000
tctgaaatag aagatagtac caagcaagtc ttttccaaag tattgtttaa agtaacgaa    6060 cattcagacc agctcacaag agaagaaaat actgctatac gtactccaga acatttaata    6120
tcccaaaaag gcttttcata taatgtggta aattcatctg cttttctctgg atttagtaca    6180 gcaagtggaa agcaagtttc catttagaa agttccttac acaaagttaa gggagtgtta    6240
gaggaatttg atttaatcag aactgagcat agtcttcact attcacctac gtctagacaa    6300
aatgtatcaa aaatacttcc tcgtgttgat aagagaaacc cagagcactg tgtaaactca    6360
gaaatggaaa aaacctgcag taaagaattt aaattatcaa ataacttaaa tgttgaaggt    6420
```

```
ggttcttcag aaaataatca ctctattaaa gtttctccat atctctctca atttcaacaa    6480
gacaaacaac agttggtatt aggaaccaaa gtctcacttg ttgagaacat tcatgttttg    6540
ggaaaagaac aggcttcacc taaaaacgta aaatggaaa ttggtaaaac tgaaacttttc    6600 tctgatgttc ctgtgaaaac aaatatagaa gtttgttcta cttactccaa agattcagaa    6660
aactactttg aaacagaagc agtagaaatt gctaaagctt ttatggaaga tgatgaactg    6720
acagattcta aactgccaag tcatgccaca cattctcttt ttacatgtcc cgaaaatgag    6780
gaaatggttt tgtcaaattc aagaattgga aaaagaagag gagagcccct tatcttagtg    6840
ggagaaccct caatcaaaag aaacttatta atgaatttg acaggataat agaaaatcaa    6900 gaaaatcct taaaggcttc aaaaagcact ccagatggca caataaaaga tcgaagattg    6960
tttatgcatc atgtttcttt agagccgatt acctgtgtac cctttcgcac aactaaggaa    7020
cgtcaagaga tacagaatcc aaattttacc gcacctggtc aagaatttct gtctaaatct    7080
catttgtatg aacatctgac tttggaaaaa tcttcaagca atttagcagt ttcaggacat    7140 ccatttatc aagtttctgc tacaagaaat gaaaaaatga cacttgat tactacaggc    7200 agaccaacca aagtctttgt tccacctttt aaaactaaat cacattttca cagagttgaa    7260
cagtgtgtta ggaatattaa cttggaggaa acagacaaa agcaaacat tgatggacat    7320 ggctctgatg atagtaaaaa taagattaat gacaatgaga ttcatcagtt taacaaaaac    7380
aactccaatc aagcagcagc tgtaactttc acaaagtgtg aagaagaacc tttagattta    7440
attacaagtc ttcagaatgc cagagatata caggatatgc gaattaagaa gaaacaaagg    7500
caacgcgtct ttcacagcc aggcagtctg tatcttgcaa aaacatccac tctgcctcga    7560
atctctctga agcagcagt aggaggccaa gttccctctg cgtgttctca taaacagctg    7620
tatacgtatg gcgtttctaa acattgcata aaattaaca gcaaaaatgc agagtcttt    7680 cagtttcaca ctgaagatta ttttggtaag gaaagtttat ggactggaaa aggaatacag    7740
ttggctgatg gcggatggct catacctcc aatgatggaa aggctggaaa agaagaattt    7800
tatagggctc tgtgtgacac tccaggtgtg gatccaaagc ttatttctag aatttgggtt    7860
tataatcact atagatggat catatggaaa ctggcagcta tggaatgtgc ctttcctaag    7920
gaatttgcta atagatgcct aagcccagaa agggtgcttc ttcaactaaa atacagatat    7980
gatacggaaa ttgatagaag cagaagatcg gctataaaaa agataatgga aagggatgac    8040
acagctgcaa aaacacttgt tctctgtgtt tctgacataa tttcattgag cgcaaatata    8100
tctgaaactt ctagcaataa aactagtagt gcagataccc aaaaagtggc cattattgaa    8160
cttacagatg ggtggtatgc tgttaaggcc cagttagatc ctcccctctt agctgtctta    8220
aagaatggca gactgacagt tggtcagaag attattcttc atggagcaga actggtgggc    8280
tctcctgatg cctgtacacc tcttgaagcc ccagaatctc ttatgttaaa gatttctgct    8340
aacagtactc ggcctgctcg ctggtatacc aaacttgggt tctttcctga ccctagacct    8400
tttcctctgc cctatcatc gcttttcagt gatggaggaa atgttggttg tgttgatgta    8460
attattcaaa gagcataccc tatacagtgg atggagaaga catcatctgg attatacata    8520
tttcgcaatg aaagagagga agaaaggaa gcagcaaaat atgtggaggc ccaacaaaag    8580
agactagaag cctattcac taaaattcag gaggaatttg aagaacatga agaaacaca    8640 acaaaaccat atttaccatc acgtgcacta acaagacagc aagttcgtgc tttgcaagat    8700
ggtgcagagc tttatgaagc agtgaagaat gcagcagacc cagcttacct tgagggttat    8760
ttcagtgaag agcagttaag agccttgaat aatcacaggc aaatgttgaa tgataagaaa    8820
```

-continued

```
caagctcaga tccagttgga aattaggaag gccatggaat ctgctgaaca aaaggaacaa    8880
ggtttatcaa gggatgtcac aaccgtgtgg aagttgcgta ttgtaagcta ttcaaaaaaa    8940
gaaaaagatt cagttatact gagtatttgg cgtccatcat cagatttata ttctctgtta    9000
acagaaggaa agagatacag aatttatcat cttgcaactt caaaatctaa aagtaaatct    9060
gaaagagcta acatacagtt agcagcgaca aaaaaaactc agtatcaaca actaccggtt    9120
tcagatgaaa tttatttca gatttaccag ccacgggagc cccttcactt cagcaaattt    9180
ttagatccag actttcagcc atcttgttct gaggtggacc taataggatt tgtcgtttct    9240
gttgtgaaaa aaacaggact tgcccctttc gtctatttgt cagacgaatg ttacaattta    9300
ctggcaataa agttttggat agaccttaat gaggacatta ttaagcctca tatgttaatt    9360
gctgcaagca acctccagtg gcgaccagaa tccaaatcag gccttcttac tttatttgct    9420
ggagattttt ctgtgttttc tgctagtcca aaagagggcc actttcaaga gacattcaac    9480
aaaatgaaaa atactgttga gaatattgac atactttgca atgaagcaga aaacaagctt    9540
atgcatatac tgcatgcaaa tgatcccaag tggtccaccc caactaaaga ctgtacttca    9600
gggccgtaca ctgctcaaat cattcctggt acaggaaaca agcttctgat gtcttctcct    9660
aattgtgaga tatattatca aagtccttta tcactttgta tggccaaaag gaagtctgtt    9720
tccacacctg tctcagccca gatgacttca aagtcttgta aaggggagaa agagattgat    9780
gaccaaaaga actgcaaaaa gagaagagcc ttggatttct tgagtagact gcctttacct    9840
ccacctgtta gtcccatttg tacatttgtt tctccggctg cacagaaggc atttcagcca    9900
ccaaggagtt gtggcaccaa atacgaaaca cccataaaga aaaagaact gaattctcct    9960
cagatgactc catttaaaaa attcaatgaa atttctcttt tggaaagtaa ttcaatagct   10020
gacgaagaac ttgcattgat aaatacccaa gctcttttgt ctggttcaac aggagaaaaa   10080
caatttatat ctgtcagtga atccactagg actgctccca ccagttcaga agattatctc   10140
agactgaaac gacgttgtac tacatctctg atcaaagaac aggagagttc ccaggccagt   10200
acggaagaat gtgagaaaaa taagcaggac acaattacaa ctaaaaaata tatctaa     10257
```

METHOD FOR EVALUATING MULTIPLE DIFFERENT GENES OF INTEREST

CROSS-REFERENCE TO RELATED APPLICATIONS

This application is the U.S. National Stage of PCT/JP2018/013539, filed Mar. 30, 2019, which claims priority to JP 2017-069085, filed Mar. 30, 2017.

The instant application contains a Sequence Listing which has been submitted in ASCII format via EFS-WEB and is hereby incorporated by reference in its entirety. Said ASCII copy, created on Sep. 26, 2019, is named sequence.txt and is 103,053 bytes.

TECHNICAL FIELD

The present invention relates to, for instance, a method for evaluating multiple different genes of interest, and markers for detecting cancer, markers for detecting mutations that suppress differentiation, and drug sensitive or resistant markers that have been identified by the evaluation method.

BACKGROUND ART

The approval of an anti-cancer drug, gefitinib, erlotinib, or afatinib as first-line treatments for advanced lung cancers currently requires the presence of classical/sensitive EGFR mutations, such as exon 19 deletions or the L858R point mutation (Non Patent Literature 1). Further, EGFR tyrosine kinase inhibitors (TKIs), in general, are clinically used for patients with uncommon sensitive mutations including exon 18 insertions/deletions, E790 mutations (Non Patent Literature 2), G719 mutations (Non Patent Literature 3), exon 19 insertions (Non Patent Literature 4), the insertion FQEA into A763-764 (Non Patent Literature 5), 57681 mutation (Non Patent Literature 6), and L861Q mutation. However, preclinical and clinical trial data suggest that first-generation EGFR tyrosine kinase inhibitors (TKIs) such as gefitinib and erlotinib are less effective to uncommon EGFR mutations are frequently (Non Patent Literature 7). The main mechanism underlying resistance to gefitinib and erlotinib is attributable to T790M mutation in the EGFR gene, which can be overcome by treatment with osimertinib (Non Patent Literature 8). However, the osimertinib treatment is known to be not effective to C797 compound mutations (Non Patent Literature 9). In addition, insertions in exon 20 are known to be involved in EGFR TKI-insensitive mutations. As described above, many EGFR gene mutations are known to strongly affect anti-cancer drug sensitivity.

In addition to these primary genomic mutations, genes on the genomes of cancer patients contain a large number of nonsynonymous mutations, which result in amino acid substitution. For example, in the COSMIC database of somatic mutations (v78; http://cancer.sanger.ac.uk/cosmic/), total 770 nonsynonymous mutations have been reported for the EGFR gene. Similarly, 442 of such mutations have been reported for the ALK gene involved in lung cancer. However, the clinical relevance remains unknown for the vast majority of such mutations.

To select an appropriate drug for each patient, it is clinically critical to develop a method for revealing clinical significance of a large number of nonsynonymous and synonymous mutations, a method for evaluating transforming potential of a plurality of genes with unknown functions and/or mutants thereof, a method for quickly and accurately evaluating drug sensitivity of a subject, and a method for evaluating whether nonsynonymous and synonymous mutations are resistant or sensitive to an existing drug or new drug. Nevertheless, no technology capable of accurately and comprehensively analyzing and evaluating individual mutations is currently known.

CITATION LIST

Non Patent Literature

Non Patent Literature 1: Nature Medicine, 2015, 21, 2, p. 99
Non Patent Literature 2: Ackerman A. et al., J. Thorac. Oncol. 2012, 7, e 19-20
Non Patent Literature 3: Han, S. W. et al., J. Clin. Oncol. 2005, 23, pp. 2493-2501
Non Patent Literature 4: He, M. et al., Clin. Cancer Res., 2012, 18, pp. 1790-1797
Non Patent Literature 5: Yasuda, H. et al., Sci. Transl. Med., 2013, 5, 216ra177
Non Patent Literature 6: Kancha, R. K. et al, Clin. Cancer Res., 2009, 15, pp. 460-467
Non Patent Literature 7: Watanabe, S. et al. J. Thorac. Oncol., 2014, 9, pp. 189-194
Non Patent Literature 8: Cross, D. A. et al., Cancer Discov., 2014, 4, pp. 1046-1061
Non Patent Literature 9: Thress, K. S. et al., Nat. Med., 2015, 21, pp. 560-562

SUMMARY OF INVENTION

Technical Problems

It is an object of the present invention to provide a method for evaluating a function, such as transforming potential, of multiple different genes of interest and a method capable of evaluating drug sensitivity of a subject having each gene of interest. It is also an object of the present invention is to provide, for instance, markers for detecting cancer, drug sensitive markers, or drug resistant markers, which can be identified by the above methods, as well as means for detecting such markers.

Solution to Problem

The present inventors have found that multiple different genes of interest can be individually and comprehensively evaluated based on a method including: mixing and culturing multiple host cells to which polynucleotides comprising tag sequences and genes of interest, etc., linked to the tag sequence are integrated; quantifying each of the polynucleotides derived from the cultured host cells based on the tag sequence; and determining a relative cell count of each of the host cells after the culturing. In addition, the present inventors have found novel markers for detecting cancer and drug sensitive markers, etc based on this method. Then, the present invention has been completed.

Specifically, the present invention includes the following aspects.

(1) A method for evaluating multiple different genes of interest, comprising the steps of:
integrating, into host cell genomic DNA, polynucleotides each comprising a tag sequence and a gene of interest or a fragment thereof linked to the tag sequence;
mixing a plurality of host cells, each having the different polynucleotides integrated therein;
culturing the mixed host cells;
extracting the genomic DNA from the cultured host cells;

quantifying each of the polynucleotides in the extracted genomic DNA based on the tag sequence; and determining a relative cell count of each of the host cells having the respective polynucleotides after the culturing, based on the quantified values for the polynucleotides.

(2) The method according to (1), wherein the gene of interest includes a reference gene, wherein the method comprises the step of comparing the relative cell count of the host cells after the culturing with a reference value, and wherein the reference value is defined as a relative cell count of a host cell comprising a polynucleotide comprising the reference gene after the culturing.

(3) The method according to (2), further comprising the step of evaluating the gene of interest as having transforming potential, when the relative cell count after the culturing is higher than the reference value.

(4) The method according to (2), wherein the culturing is performed under a differentiation-inducing condition, and the method further comprises the step of evaluating, the gene of interest as a gene that suppresses the differentiation, when the relative cell count after the culturing is higher than the reference value.

(5) The method according to (1) or (2), wherein the culturing is performed under a test environment.

(6) The method according to (5), wherein the test environment is in the presence of a test substance.

(7) The method according to (6), wherein the genes of interest is oncogene, wherein the culturing is performed in a presence of an anti-cancer drug, and wherein the method comprises the step of evaluating sensitivity of the oncogene to the anti-cancer drug based on the relative cell count after the culturing.

(8) The method according to (7), wherein the anti-cancer drug is a low-molecular-weight compound and/or an antibody drug.

(9) A method for determining an anti-cancer drug, comprising the step of performing the method according to (7) or (8) for a plurality of anti-cancer drugs once or multiple times independently to determine an anti-cancer drug effective for the oncogene based on the obtained results of sensitivities to the anti-cancer drugs.

(10) The method according to (6), wherein the gene of interest is an tumor suppressor gene, wherein the host cells are cells deficient in the tumor suppressor gene, and the culturing is performed under treatment which causes the damage to the host cells that can be repaired by the tumor suppressor gene.

(11) The method according to (10), wherein the agent is a PARP inhibitor.

(12) The method according to any one of (1) to (11), wherein the plurality of host cells having the different polynucleotides integrated therein are derived from the same cell line.

(13) The method according to any one of (1) to (12), wherein the gene of interest includes a plurality of mutants of one oncogene.

(14) The method according to any one of (1) to (13), wherein the gene of interest includes a compound mutation-bearing gene containing a plurality of mutations to a wild-type gene.

(15) The method according to any one of (1) to (14), wherein the quantifying step is performed based on read counts obtained by next-generation sequencing.

(16) The method according to any one of (1) to (15), wherein the culturing is performed in vivo using a non-human animal.

(17) A marker for detecting cancer, consisting of an EGFR protein having an mutation selected from the group consisting of H304Y, P741L, S752-I759del, H773Y, A767V, V786M, L838P, E865K, A871G, G874S, V802I, and S1153I.

(18) A marker for detecting cancer, consisting of an EGFR protein having a compound mutation selected from the group consisting of L62R and G719S (trans), R108K and L858R (trans), A216T and E746-S752>V (cis), A216T and E746-S752>V (trans), A289T and L858R (cis), A289T and L858R (trans), V292L and L858R (cis), V292L and L858R (trans), S306L and L858R (cis), S306L and L858R (trans), L7031 and L858R (cis), L7031 and L858R (trans), I706T and G719A (cis), I706T and G719A (trans), E709A and G719C (cis), E709A and G719C (trans), E709A and G719S (cis), E709A and G719S (trans), E709A and L858R (cis), E709A and L858R (trans), E709G and L858R (trans), E709K and L858R (cis), E709K and L858R (trans), E709V and L858R (cis), E709V and L858R (trans), K714R and L858R (cis), K714R and L858R (trans), L718Q and L858R (cis), L718Q and L858R (trans), S720F and L858R (cis), S720F and L858R (trans), I744M and L858R (cis), S768I and G719A (cis), S768I and G719A (trans), S768I and G719C (cis), S768I and G719C (trans), S768I and G719S (cis), S768I and G719S (trans), S768I and L858R (cis), S768I and L858R (trans), R776C and L858R (cis), R776C and L858R (trans), R776G and L858R (cis), R776G and L858R (trans), T790M and C797S (cis), T790M and E746-A750del (cis), T790M and E746-A750del (trans), T790M and G719A (cis), T790M and G719A (trans), T790M and L858R (cis), T790M and L858R (trans), L833V and L858R (cis), L833V and L858R (trans), L838V and L858R (cis), L838V and L858R (trans), V843I and L858R (cis), V843I and L858R (trans), L861Q and G719A (cis), L861Q and G719A (trans), L861Q and L858R (cis), L861Q and L858R (trans), L861R and G719A (cis), L861R and G719A (trans), A871G and L858R (cis), A871G and L858R (trans), A1118T and E746-A750del (cis), and A1118T and E746-A750del (trans).

(19) A marker for detecting cancer, consisting of a polynucleotide encoding an EGFR protein having the mutation defined in (17) or (18).

(20) A fusion protein comprising a COL1A2 protein and a DCAF6 protein.

(21) The fusion protein according to (20), comprising: an amino acid sequence set forth in SEQ ID NO: 7; an amino acid sequence having 90% or more identity to the amino acid sequence set forth in SEQ ID NO: 7; or an amino acid sequence having a plurality of amino acid additions, deletions, and/or substitutions in the amino acid sequence set forth in SEQ ID NO: 7.

(22) A polynucleotide encoding the fusion protein according to (20) or (21).

(23) A marker for detecting a mutation that suppresses differentiation, consisting of the fusion protein according to (20) or (21) or the polynucleotide according to (22).

(24) A cetuximab sensitive marker consisting of an EGFR protein having a mutation elected from the group consisting of L62R, L62R and L858R (cis), R108K, R108K and L858R (cis), A216T, A289D, A289T, A289T and L858R (cis), A289V, V292L, V292L and L858R (cis), H304Y, S306L, P596L, G598V, R669Q, E709A, E709A and G719C (trans), E709K, E709V, K714R, L718Q, S720F, L747V, P753S, A767V, V769L, V769M, H773L, V774M, R776H, C797S, L833V, V843I, R776C, and R831L, or a polynucleotide encoding the protein.

(25) A cetuximab resistant marker consisting of an EGFR protein having a mutation selected from the group consisting of L62R and G719S (trans), L62R and L858R (trans), R108K and L858R (trans), A216T and E746-S752>V (cis), A216T and E746-S752>V (trans), A289T and L858R (trans), S306L and L858R (cis), S306L and L858R (trans), S492R, R669Q and L858R (cis), R669Q and L858R (trans), L703I, L703I and L858R (cis), L703I and L858R (trans), I706T and G719A (cis), I706T and G719A (trans), E709-T710>D, E709A and G719C (cis), E709A and G719S (cis), E709A and G719S (trans), E709A and L858R (cis), E709A and L858R (trans), E709K and L858R (cis), E709K and L858R (trans), E709V and L858R (cis), E709V and L858R (trans), K714R and L858R (cis), K714R and L858R (trans), L718Q and L858R (cis), L718Q and L858R (trans), G719A, G719C, G719S, S720F and L858R (cis), S720F and L858R (trans), G735S, K739N, K739N and L858R (cis), K739N and L858R (trans), I744M, I744M and L858R (cis), K745-E746insVPVAIK, E746-S752>V, E746-A750>IP, E746-P753>VS, E746-T751>V, L747-A750>P, L747-A750del, L747-P753>Q, L747-P753>S, L747-T751>P, L747-T751>S, L747-T751del, L747S, L747V and L858R (cis), L747V and L858R (trans), T751-I759>N, S752-I759del, I759M, I759M and L858R (cis), I759M and L858R (trans), D761-E762insEAFQ, A763-Y764insFQEA, V765M, S768I, S768I and G719A (cis), S768I and G719A (trans), S768I and G719C (cis), S768I and G719C (trans), S768I and G719S (cis), S768I and G719S (trans), S768I and L858R (cis), S768I and L858R (trans), D770-N771insSVD, N771-P772insN, H773-V774insH, H773Y, V774-C775insHV, R776C and L858R (cis), R776C and L858R (trans), R776G, R776G and L858R (cis), R776G and L858R (trans), T790M, T790M and C797S (cis), T790M and E746-A750del (cis), T790M and E746-A750del (trans), T790M and G719A (cis), T790M and G719A (trans), T790M and L858R (cis), T790M and L858R (trans), P798H, V802I, L833V and L858R (cis), L833V and L858R (trans), V834L, L838V, L838V and L858R (cis), L838V and L858R (trans), V843I and L858R (cis), V843I and L858R (trans), V851I, T854A, L858R, A859T, L861Q, L861Q and G719A (cis), L861Q and G719A (trans), L861Q and L858R (cis), L861Q and L858R (trans), L861R, L861R and G719A (cis), L861R and G719A (trans), E865K and L858R (cis), A871G, A871G and L858R (cis), A871G and L858R (trans), G873E, A1118T, A1118T and E746-A750del (cis), and A1118T and E746-A750del (trans), or a polynucleotide encoding the protein.

(26) A marker resistant to an EGFR tyrosine kinase inhibitor, consisting of an EGFR protein having A839T mutation.

(27) A gefitinib sensitive marker consisting of an EGFR protein having a mutation selected from the group consisting of R108K and L858R (cis), A216T, A216T and E746-S752>V (cis), A289T and L858R (cis), V292L and L858R (cis), V292L and L858R (trans), S306L, S306L and L858R (cis), S306L and L858R (trans), L703I and L858R (cis), L703I and L858R (trans), E709A and G719C (trans), E709G and L858R (trans), E709V and L858R (cis), K714R and L858R (cis), K714R and L858R (trans), L718Q and L858R (trans), G719C, S720F, S720F and L858R (cis), S720F and L858R (trans), T751-I759>N, S752-I759del, S768I and G719C (cis), R776C and L858R (cis), R776C and L858R (trans), R776G and L858R (cis), R776G and L858R (trans), R831L, V834M, H835L, L838V and L858R (cis), V843I and L858R (cis), V843I and L858R (trans), L861Q and L858R (cis), A871G, A871G and L858R (cis), A871G and L858R (trans), A1118T, A1118T and E746-A750del (cis), L62R, R108K, R108K and L858R (trans), R222C, R252C, A289D, A289T, A289T and L858R (trans), A289V, V292L, H304Y, S492R, P596L, G598V, L703I, L703P, I706T and G719A (trans), E709A and L858R (cis), E709A and L858R (trans), E709K, E709K and L858R (cis), E709K and L858R (trans), E709V, E709V and L858R (trans), K714R, G719A, G719S, G735S, P741L, I744M, I744M and L858R (cis), K745-E746insVPVAIK, L747S, T751I, P753S, D761-E762insEAFQ, A763-Y764insFQEA, V765M, A767V, S768I and G719A (trans), S768I and G719C (trans), S768I and L858R (trans), V769M, H773Y, R776C, R776G, R776H, G779S, V786M, C797S, P798H, V802I, R831H, L833F, L833V, L833V and L858R (cis), L833V and L858R (trans), V834L, L838V, L838V and L858R (trans), V843I, P848L, A859T, K860I, L861Q, L861Q and G719A (trans), L861Q and L858R (trans), L861R, L861R and G719A (trans), E865K, G874S, and S1153I, or a polynucleotide encoding the protein.

(28) A gefitinib resistant marker consisting of an EGFR protein having a mutation selected from the group consisting of L62R and G719S (trans), I706T and G719A (cis), E709-T710>D, E709A, E709A and G719C (cis), E709A and G719S (cis), E709A and G719S (trans), E709G, L718Q, L718Q and L858R (cis), S768I, S768I and G719A (cis), S768I and G719S (trans), V769L, H773L, V774M, T790M and G719A (cis), T790M and G719A (trans), V851I, T854A, L861Q and G719A (cis), L861R and G719A (cis), A864T, A871T, G873E, and A1118T and E746-A750del (trans), or a polynucleotide encoding the protein.

(29) An erlotinib sensitive marker consisting of an EGFR protein having a mutation selected from the group consisting of R108K and L858R (cis), R108K and L858R (trans), A216T, A216T and E746-S752>V (cis), A216T and E746-S752>V (trans), A289T and L858R (cis), A289T and L858R (trans), V292L and L858R (cis), V292L and L858R (trans), S306L, S306L and L858R (cis), S306L and L858R (trans), L703I and L858R (cis), L703I and L858R (trans), E709A and G719C (cis), E709A and G719C (trans), E709G and L858R (trans), E709K and L858R (cis), E709K and L858R (trans), E709V and L858R (cis), E709V and L858R (trans), K714R and L858R (cis), K714R and L858R (trans), L718Q and L858R (trans), G719C, G719S, S720F, S720F and L858R (cis), S720F and L858R (trans), T751-I759>N, S752-I759del, S768I and G719C (cis), S768I and L858R (cis), R776C and L858R (cis), R776C and L858R (trans), R776G and L858R (cis), R776G and L858R (trans), L833V and L858R (cis), L838V and L858R (cis), L838V and L858R (trans), V843I and L858R (cis), V843I and L858R (trans), L861Q and L858R (cis), A871G and L858R (cis), A871G and L858R (trans), A1118T, A1118T and E746-A750del (cis), L62R, R108K, R222C, R252C, A289D, A289T, A289V, V292L, H304Y, S492R, P596L, G598V, L703I, L703P, I706T and G719A (trans), E709A and L858R (cis), E709A and L858R (trans), E709K, E709V, K714R, G719A, G735S, P741L, I744M, I744M and L858R (cis), K745-E746insVPVAIK, L747S, T751I, P753S, D761-E762insEAFQ, A763-Y764insFQEA, V765M, A767V, S768I, S768I and G719A (trans), S768I and G719C (trans), S768I and L858R (trans), V769M, H773Y, R776C, R776G, R776H, G779S, V786M, C797S, P798H, V802I, R831H, R831L, L833F, L833V, L833V and L858R (trans), V834L, V834M, H835L, L838V, L838V and L858R (trans), V843I, P848L, A859T, K860I, L861Q, L861Q and G719A (trans), L861Q and L858R (trans), L861R, L861R and G719A (trans), A864T, E865K, A871G, A871T, G874S, S1153I, or a polynucleotide encoding the protein.

(30) An erlotinib resistant marker consisting of an EGFR protein having a mutation selected from the group consisting of L62R and G719S (trans), I706T and G719A (cis), E709-T710>D, E709A, E709A and G719S (cis), E709A and G719S (trans), E709G, L718Q, L718Q and L858R (cis), S768I and G719A (cis), S768I and G719S (cis), S768I and G719S (trans), V769L, N771-P772insN, N771-P772insN, H773L, V774M, T790M and G719A (cis), T790M and G719A (trans), V851I, T854A, L861Q and G719A (cis), L861R and G719A (cis), G873E, and A1118T and E746-A750del (trans), or a polynucleotide encoding the protein.

(31) An afatinib sensitive marker consisting of an EGFR protein having a mutation selected from the group consisting of L62R, R108K, R108K and L858R (cis), R108K and L858R (trans), A216T, A216T and E746-S752>V (cis), A216T and E746-S752>V (trans), R222C, R252C, A289D, A289T, A289T and L858R (cis), A289T and L858R (trans), A289V, V292L, V292L and L858R (cis), V292L and L858R (trans), H304Y, S306L, S306L and L858R (cis), S306L and L858R (trans), S492R, P596L, G598V, L703I, L703I and L858R (cis), L703I and L858R (trans), L703P, I706T and G719A (trans), E709-T710>D, E709A, E709A and G719C (trans), E709A and L858R (cis), E709A and L858R (trans), E709G, E709G and L858R (trans), E709K, E709K and L858R (cis), E709K and L858R (trans), E709V, E709V and L858R (cis), E709V and L858R (trans), K714R, K714R and L858R (cis), K714R and L858R (trans), L718Q and L858R (trans), G719A, G719C, G719S, S720F, S720F and L858R (cis), S720F and L858R (trans), G735S, P741L, I744M, I744M and L858R (cis), L747-P753>Q, L747S, T751-1759>N, S752-1759del, P753S, D761-E762insEAFQ, A763-Y764insFQEA, V765M, A767V, S768I and G719A (trans), S768I and G719C (trans), S768I and G719S (cis), S768I and L858R (cis), S768I and L858R (trans), V769M, H773Y, R776C, R776C and L858R (cis), R776C and L858R (trans), R776G, R776G and L858R (cis), R776G and L858R (trans), R776H, V786M, P798H, V802I, R831H, R831L, L833F, L833V, L833V and L858R (cis), L833V and L858R (trans), V834L, V834M, H835L, L838V, L838V and L858R (cis), L838V and L858R (trans), V843I, V843I and L858R (cis), V843I and L858R (trans), P848L, K860I, L861Q, L861Q and G719A (trans), L861Q and L858R (cis), L861Q and L858R (trans), L861R, A864T, E865K, A871G, A871G and L858R (cis), A871G and L858R (trans), A871T, G874S, A1118T, A1118T and E746-A750del (cis), S1153I, T751I, S768I, V769L, H773L, V774M, G779S, T854A, A859T, and G873E, or a polynucleotide encoding the protein.

(32) An afatinib resistant marker consisting of an EGFR protein having a mutation selected from the group consisting of L62R and G719S (trans), I706T and G719A (cis), E709A and G719C (cis), E709A and G719S (cis), E709A and G719S (trans), L718Q, L718Q and L858R (cis), S768I and G719A (cis), S768I and G719C (cis), S768I and G719S (trans), V769-D770insASV, D770-N771insSVD, N771-P772insN, H773-V774insH, H773-V774insPH, V774-C775insHV, T790M and G719A (cis), T790M and G719A (trans), C797S, V851I, L861Q and G719A (cis), L861R and G719A (cis), L861R and G719A (trans), and A1118T and E746-A750del (trans), or a polynucleotide encoding the protein.

(33) An osimertinib sensitive marker consisting of an EGFR protein having a mutation selected from the group consisting of L62R, R108K, R108K and L858R (cis), R108K and L858R (trans), A216T, A216T and E746-S752>V (cis), A216T and E746-S752>V (trans), R222C, R252C, A289D, A289T, A289T and L858R (cis), A289T and L858R (trans), A289V, V292L, V292L and L858R (cis), V292L and L858R (trans), H304Y, S306L, S306L and L858R (cis), S306L and L858R (trans), S492R, P596L, G598V, L703I and L858R (cis), L703I and L858R (trans), L703P, E709A and G719C (trans), E709A and G719S (trans), E709A and L858R (trans), E709G and L858R (trans), E709K and L858R (cis), E709K and L858R (trans), E709V and L858R (cis), E709V and L858R (trans), K714R and L858R (cis), K714R and L858R (trans), G719C, G719S, S720F, S720F and L858R (cis), S720F and L858R (trans), G735S, P741L, I744M and L858R (cis), K745-E746insVPVAIK, E746-A750>IP, E746-P753>VS, E746-T751>V, L747-A750>P, L747-A750del, L747-P753>Q, L747-P753>S, L747-T751>P, L747-T751>S, L747-T751del, L747S, T751-1759>N, T751I, S752-1759del, P753S, D761-E762insEAFQ, A763-Y764insFQEA, V765M, A767V, S768I and L858R (cis), V769-D770insASV, V769L, V769M, N771-P772insN, H773-V774insH, H773-V774insPH, H773L, H773Y, V774-C775insHV, V774M, R776C, R776C and L858R (cis), R776C and L858R (trans), R776G, R776G and L858R (cis), R776G and L858R (trans), R776H, G779S, V786M, T790M, T790M and G719A (trans), T790M and L858R (trans), P798H, V802I, R831H, R831L, L833F, L833V, L833V and L858R (cis), L833V and L858R (trans), V834L, V834M, H835L, L838V and L858R (cis), L838V and L858R (trans), V843I, V843I and L858R (cis), V843I and L858R (trans), P848L, V851I, T854A, L858R, A859T, K860I, L861Q, L861Q and L858R (cis), L861Q and L858R (trans), A864T, A871G, A871G and L858R (cis), A871G and L858R (trans), G873E, G874S, E746-S752>V, A1118T, A1118T and E746-A750del (cis), S1153I, L62R and G719S (trans), I706T and G719A (cis), I706T and G719A (trans), E709-T710>D, E709A, E709A and G719C (cis), E709G, E709K, E709V, K714R, G719A, I744M, S768I, S768I and G719A (trans), S768I and G719C (cis), S768I and G719C (trans), S768I and G719S (cis), S768I and G719S (trans), S768I and L858R (trans), D770-N771insSVD, T790M and E746-A750del (trans), L838V, L861Q and G719A (trans), L861R, L861R and G719A (cis), and L861R and G719A (trans), or a polynucleotide encoding the protein.

(34) An osimertinib resistant marker consisting of an EGFR protein having a mutation selected from the group consisting of S306L, L703I, E709A and G719S (cis), E709A and L858R (cis), L718Q, L718Q and L858R (cis), L718Q and L858R (trans), S768I and G719A (cis), T790M and E746-A750del (cis), T790M and G719A (cis), C797S, L861Q and G719A (cis), E865K, A871T, and A1118T and E746-A750del (trans), or a polynucleotide encoding the protein.

(35) A rociletinib sensitive marker consisting of an EGFR protein having a mutation selected from the group consisting of E746-A750>IP, E746-P753>VS, E746-T751>V, L747-A750>P, L747-A750del, L747-P753>Q, L747-P753>S, L747-T751>P, L747-T751>S, L747-T751del, T751-1759>N, S752-1759del, H835L, L858R, A871T, A1118T, R108K, R222C, R252C, A289D, A289T, H304Y, P596L, L62R, G719A, G719C, G719S, G735S, K745-E746insVPVAIK, L747S, T751I, D761-E762insEAFQ, V765M, H773L, V774-C775insHV, V774M, V786M, T790M, P798H, R831H, L833F, V851I, K860I, L861Q, G873E, G874S, and S1153I, or a polynucleotide encoding the protein.

(36) A rociletinib resistant marker consisting of an EGFR protein having a mutation selected from the group consisting of A289V, S492R, G598V, L703P, E709-T710>D, E709A, E709G, E709K, E709V, S720F, P741L, P753S, A763-Y764insFQEA, A767V, S768I, V769-D770insASV, V769L, V769M, D770-N771insSVD, N771-P772insN, H773-V774insH, H773-V774insPH, H773Y, R776C, R776H, G779S, C797S, V802I, R831L, L833V, V834L, V834M, V843I, P848L, T854A, A859T, A864T, E865K, and A871G, or a polynucleotide encoding the protein.

(37) A marker for detecting cancer, consisting of a BRCA2 protein having a mutation selected from the group consisting of R2659G, N3124I, L2604P, W31C, E2663K, W2626R, D3073G, G2609D, P2329L, D2913H, P2639L, S3291C, D23V, I2664M, K485*, L997*, Q1502*, K1984*, C2535*, and W2970*, or a polynucleotide encoding the protein.

(38) A primer set, a probe, an aptamer, or an antibody, or a kit comprising any thereof, for detecting the marker according to any one of (17) to (19) and (23) to (37).

(39) A method for assisting in determining whether or not a subject suffers from cancer or has a possibility of suffering from cancer, comprising the step of detecting the marker according to any one of (17) to (19) and (37) in a sample obtained from the subject.

(40) A method for assisting in determining whether or not a subject has a mutation that suppresses differentiation or has a possibility of suffering from cancer, comprising the step of detecting the marker according to (23) in a sample obtained from the subject.

(41) A method for assisting in determining sensitivity to cetuximab, comprising the step of detecting the marker according to (24) or (25) in a sample obtained from a subject.

(42) A method for assisting in determining sensitivity to a drug, comprising the step of detecting at least one marker according to any one of (26) to (36) in a sample obtained from a subject.

(43) A cell population comprising at least two different cells, each comprising a polynucleotide encoding an EGFR protein having the mutation defined in (17) or (18).

(44) A cell population comprising at least two different cells, each comprising a polynucleotide encoding the fusion protein according to (20) or (21).

(45) A cell population comprising at least two different cells, each comprising a polynucleotide encoding an EGFR protein having the mutation defined in (24) to (36).

(46) A cell population comprising at least two different cells, each comprising a polynucleotide encoding a BRCA2 protein having the mutation defined in (37).

The disclosure of JP Patent Application No. 2017-069085, from which the present application claims priority, is herein incorporated.

Advantageous Effects of Invention

The present invention allows for quick, accurate, and comprehensive evaluation of a function such as transforming potential of multiple different genes of interest and drug sensitivity or resistance of cells with each gene of interest. Further, use of various markers identified by the methods of the present invention makes it possible to evaluate whether or not a subject suffers from cancer or has a possibility of suffering from cancer as well as drug sensitivity, etc.

BRIEF DESCRIPTION OF DRAWINGS

FIG. 5-1 shows the sensitivity of cells expressing the wild-type EGFR (WT) or each EGFR protein having each mutation to gefitinib, erlotinib, afatinib, osimertinib, or rociletinib. In the graphs, the ordinate indicates drug concentrations (including, from the top to bottom, 0.0001 µM, 0.0005 µM, 0.001 µM, 0.005 µM, 0.01 µM, 0.05 µM, 0.1 µM, 0.5 µM, 1 µM, 5 µM, and 10 µM); and the abscissa indicates the used cells with each mutation. The kind of each mutation (i.e., a missense mutation, deletion, or insertion) is represented by graduated shading at the top section. Regarding the rest portions, the relative viability is color-coded and as the color becomes deeper, the viability is indicated to be lower.

FIG. 5-2 This figure is a continued sheet of FIG. 5-1.

FIG. 6-1 shows the sensitivity of cells expressing an EGFR protein having each mutation to gefitinib, erlotinib, afatinib, or osimertinib. In the graphs, the ordinate indicates drug concentrations (including, from the top to bottom, 0.0001 µM, 0.0005 µM, 0.001 µM, 0.005 µM, 0.01 µM, 0.05 µM, 0.1 µM, 0.5 µM, 1 µM, 5 µM, and 10 µM); and the abscissa indicates the used cells with each mutation. The relative viability is color-coded and as the color becomes deeper, the viability is indicated to be lower.

FIG. 6-2 This figure is a continued sheet of FIG. 6-1.

FIG. 7 shows the results of evaluating cells expressing an EGFR protein containing each single mutation or each compound mutation by 3T3 focus-formation assay. The results indicate that as the color of the solution becomes deeper, the cells proliferate more and thus have stronger transforming potential. The GFP and the Wt indicates evaluation of cells expressing a green fluorescent protein and a wild-type EGFR-containing protein, respectively. The Single indicates evaluation of cells expressing a protein containing each mutation listed in the left column of the table; the Cis indicates evaluation of cells expressing a protein containing L858R (at a cis position) in addition to each mutation listed in the left column of the table; and the Trans indicates evaluation of cells expressing a protein containing L858R (at a trans position) in addition to each mutation listed in the left column of the table.

FIG. 8-1 shows the sensitivity of cells expressing an EGFR protein having each mutation to cetuximab. In the graphs, the ordinate indicates drug concentrations (including, from the top to bottom, 0.001 µg/mL, 0.01 µg/mL, 0.1 µg/mL, 1 µg/mL, 10 µg/mL, and 100 µg/mL); and the abscissa indicates the used cells with each mutation. The relative viability is color-coded and as the color becomes deeper, the viability is indicated to be lower.

FIG. 8-2 This figure is a continued sheet of FIG. 8-1.

DESCRIPTION OF EMBODIMENTS

Figure 1:
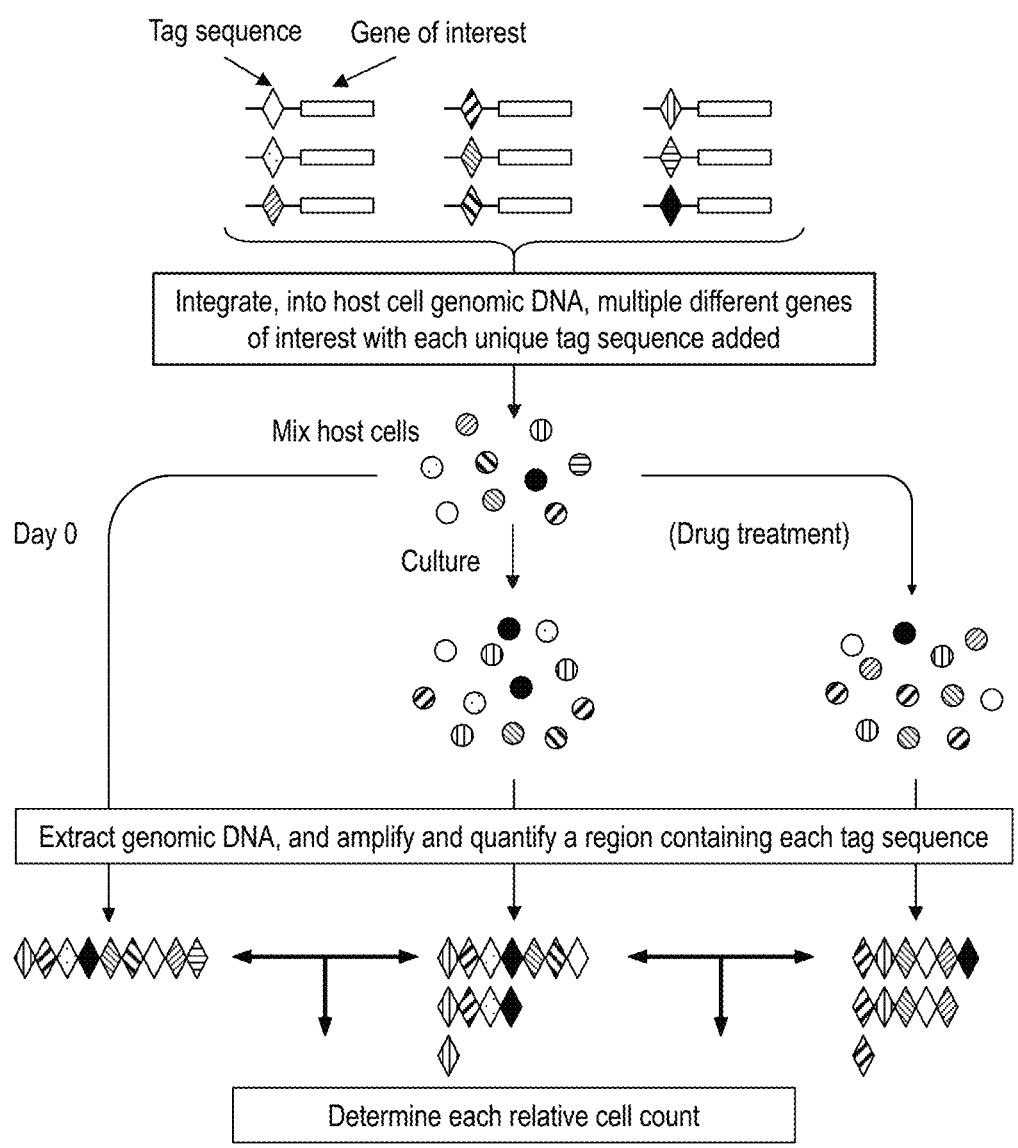
FIG. 1 is a conceptual diagram illustrating one embodiment of method of evaluating multiple different genes of interest of the present invention.

<Method of Evaluating Multiple Genes of Interest>
(Evaluation Method According to the Present Invention)

In one aspect, the present invention relates to a method for evaluating multiple different genes of interest (hereinafter, also simply referred to as an "evaluation method of the present invention"). As used herein, the lower limit of the "multiple" range is not particularly limited but may be, for example, 2 or more, 3 or more, 4 or more, 5 or more, 10 or more, 20 or more, 30 or more, 50 or more, or 100 or more. Likewise, the upper limit of the "multiple" range is not particularly limited but may be, for example, 1000 or less, 500 or less, or 300 or less.

As used herein, the kind of the "gene of interest" is not particularly limited. The method of the present invention can evaluate the proliferation rate and/or viability of a cell, so that the gene of interest may be a gene affecting the proliferation rate and/or viability of the cell. Examples of the gene affecting the proliferation rate and/or viability of a cell include: oncogenes; tumor suppressor genes; apoptosis-related genes; cellular senescence-related genes; genes that suppress differentiation (under a differentiation-inducing condition); genes involving sternness maintenance; drug sensitive or resistant (in the presence of a drug) genes; and stress sensitive or resistant (under a stress condition) genes. Examples of the oncogenes include EGFR (Epidermal Growth Factor Receptor) genes, ALK (Anaplastic Lymphoma Kinase) genes, RAS genes (e.g., the KRAS gene, NRAS gene, HRAS gene), and RET (REarranged during Transfection) genes. Examples of the tumor suppressor genes include BRCA1, BRCA2, TP53, MSH2, MSH6, MLH1, APC, NF1, INK4A, PTEN, and RB1 genes.

Both of a wild-type gene of interest and mutants thereof may have a function to be evaluated. Alternatively, either a wild-type gene of interest or mutants thereof may have a function to be evaluated. As used herein, the term "mutation" means having a trait different from a vast majority (wild-type) of a population; and the term "mutant" means a material such as a nucleic acid and protein harboring such a trait. In general, the mutation can be identified by comparing a gene nucleotide sequence or protein amino acid sequence in a subject with such a sequence of wild-type in healthy subjects.

Examples of the kind of a mutation include, but are not limited to, mutations at the gene level, i.e. mutations on nucleotide sequences such as nonsynonymous mutations including nonsense mutations that change an amino acid codon to a stop codon; missense mutations that substitute a nucleotide in a codon to produce an amino acid substitution; insertion/deletion mutations that insert and/or delete a nucleotide(s) in a codon to produce an amino acid(s) insertion and/or deletion; and frame-shift mutations that cause a codon reading frame to be shifted by insertion or deletion of a nucleotide. Examples of the mutations herein further include silent mutations (synonymous mutations) that cause a mutation in a nucleotide sequence but there is no amino acid alteration. Furthermore, examples of the mutations of the present invention include: fusion mutations formed by fusing one gene and another gene; and exon skipping that produces a transcript in which a part of an exon(s) is removed. A mutation in a gene of interest may be a mutation with known meaning or a VUS (Variant of Uncertain Significance).

Genes of interest may include multiple mutants of one gene such as an oncogene.

In addition, gene(s) of interest may contain a compound mutation where multiple mutations are included in a wild-type gene. For instance, the number of multiple mutations included in a compound mutation is, but is not limited to, 2, 3, or 4.

The method for evaluating genes of interest according to the present invention comprises the essential steps of: integrating, into host cell genomic DNA, polynucleotides each comprising a tag sequence and a gene of interest or a fragment thereof linked to the tag sequence (integration step); mixing a plurality of host cells having the different polynucleotides integrated therein (mixing step); culturing the mixed host cells (culturing step); extracting the genomic DNA from the cultured host cells (extracting step); quantifying each of the polynucleotides in the extracted genomic DNA based on the tag sequence (quantification step); and determining a relative cell count of each of the host cells having the respective polynucleotides after the culturing, based on the quantified values for the polynucleotides (determination step).

In addition, the evaluation method of the present invention may further comprise, as an optional step, after the determination step, the step of comparing the relative cell count of the host cells after the culturing with a reference value (comparison step), wherein the gene of interest includes a reference gene, and the reference value is defined as a relative cell count of a host cell comprising a polynucleotide comprising the reference gene after the culturing. In addition to the comparison step, the evaluation method of the present invention may further optionally comprise, after the determination step or the comparison step, the step of evaluating the gene of interest by comparing it with the reference value obtained in the comparison step or with other genes of interest (evaluation step).

The evaluation method according to one embodiment of the present invention is described with reference to FIG. 1. In FIG. 1, polynucleotides containing genes of interest with tag sequences are integrated into host cell genomic DNA; the respective cells are mixed; and part of the cells is randomly collected to give a sample at Day 0. Next, the mixed cells are cultured under any condition (e.g., a regular culture condition or drug treatment condition) for a suitable time period. Subsequently, genomic DNA is extracted from the cells and nucleic acid region(s) containing tag sequence (s) is amplified and then quantified. After that, based on the quantified value, a relative count of the cell having the gene of interest is determined. When determining the relative count of the cell, the count may be optionally normalized by the value at Day 0 (before the culturing). The method for evaluating multiple different genes of interest according to the present invention may be used for evaluating, for instance, whether or not they have transforming potential, whether or not they include a gene that suppresses differentiation, and whether the oncogene is sensitive to an anti-cancer drug(s).

Each step included in the method of the present invention is described below in detail.

(Integration Step)

In the integration step, polynucleotides comprising tag sequences and genes of interest or a fragment thereof linked to the tag sequences are integrated into host cell genomic DNA.

As used herein, the "tag sequence" or "bar code sequence" means a unique identification sequence added to each gene of interest or a fragment thereof. The tag sequence may be directly linked to a gene of interest or may be indirectly linked to a gene of interest via another sequence such as a spacer sequence.

By integrating a gene of interest linked to a tag sequence into genomic DNA, each polynucleotides in the genomic DNA can be quantified based on the tag sequence in the quantification step described below. The length of the tag sequence is not limited, and, preferably, such a length that the each gene of interest can be identified. The nucleotide length of the tag sequence may be, for instance, 2 or more, 3 or more, 4 or more, 5 or more, 6 or more, or 8 or more and 50 or less, 40 or less, 30 or less, 20 or less, or 10 or less. When the nucleotide length of the tag sequence is set to n, it is theoretically possible to add each unique tag sequence to each of $4^n$ different genes of interest.

A method for integrating a gene of interest into host cell genomic DNA is not limited and any methods known to those skilled in the art can be used therefor. Examples of such a method include: methods using a viral vector such as a retroviral vector or lentiviral vector; methods using, for instance, a Cre-Lox recombinase system; gene introduction methods using a transposase, such as Piggy Bac Transposon Vector System; and methods using a genome-editing protein such as TALEN (Transcription activator-like effector nuclease) (see, for instance, WO2011/072246), CRISPR-Cas9 (Clustered Regularly Interspaced Short Palindromic Repeat/CRISPR associated protein 9) (see, for instance, Hendel A. et al., Nature Biotechnology, 2015, 33, pp. 985-989), or ZFN (zinc finger nuclease) (see, for instance, M. Bibikova et al., Genetics, 2002, 161, pp. 1169-1175).

In the integration step, polynucleotides are integrated into host cell genomic DNA in a state in which a gene of interest can be expressed. The "state in which a gene of interest can be expressed" means a state in which a gene of interest is present in combination with a regulatory sequence which is necessary for its expression so that the gene of interest can be expressed. Examples of the regulatory sequence include promoters, enhancers, terminators, S-D (Shine-Dalgarno) sequences or ribosome binding sites, replication origins, and poly-A sites. These regulatory sequences may be endogenous ones in host cell genomic DNA or may be exogenous ones that have been artificially integrated into host cell genome together with gene(s) of interest in the integration step. In addition, gene(s) of interest may be integrated into host cell genome together with a selection marker such as a drug resistance gene, and this selection marker may be used to select a cell having the gene of interest introduced therein after the integration.

The kind of the host cell is not limited and is preferably a cell of mammal, for example, primates (e.g., a human, chimpanzee), experimental animals (e.g., a rat, mouse), domestic animals (e.g., a pig, cow, horse, sheep, goat), and pets (e.g., a dog, cat), preferably, human. Examples of cells that can be used for the evaluation method of the present invention include: cell lines such as HEK293 cells, 3T3 cells, Ba/F3 cells, CHO cells; and primary cultured cells. The cells used can be suitably selected depending on gene(s) of interest to be evaluated, taking into account the presence or absence of a disease, the presence or absence of a mutation, and/or a tissue origin.

The cultured cells may be wild-type cells or may be a mutated cells in which oncogenes; tumor suppressor genes; apoptosis-related genes; cellular senescence-related genes; genes that suppress differentiation; genes involving stemness maintenance; drug sensitive or resistant genes; and stress sensitive or resistant genes are knock out or deficient.

In the evaluation method of the present invention, two or more different cells may be used to evaluate a function of gene(s) of interest in cells. To exclude influences due to a difference in, for instance, the proliferation rate between cell lines during the culturing step described below, it is preferable that the same cell line is used for the integration step and the later mixing step.

(Mixing Step)

In the mixing step, a plurality of host cells are mixed, having the polynucleotides containing each different gene of interest integrated therein in the above integration step. In this step, it is preferable that the plurality of host cells are mixed in substantially equal proportions, but they may be mixed in different proportions. To normalize the quantified values described below, the cells immediately after the mixing may be sampled as reference cells. The results of host cell(s) may be normalized by using the results of the reference cells, after the culturing step described below, so that a difference in the proportion between the numbers of cells mixed in the mixing step can be corrected.

(Culturing Step)

In the culturing step, the host cells mixed at the above mixing step are cultured under suitable conditions. In the culturing step, culture conditions such as medium components, temperature, pH, humidity, and $CO_2$ level, may be set to regular conditions known to those skilled in the art or may be under a specific test environment. The "test environment" means a particular condition in which gene(s) of interest of the present invention is tested. Examples of the test environment include: under the presence of a drug such as an anti-cancer drug; under conditions that suppress or promote differentiation; and under stress conditions such as conditions under starvation stress or temperature stress.

The duration of the culturing step is not particularly limited. The duration of the culturing step may be, for instance, 1 day or longer, 2 days or longer, 3 days or longer, 4 days or longer, 5 days or longer, 6 days or longer, 1 week or longer, or 2 weeks or longer, and 3 months or shorter, 2 months or shorter, 1 month or shorter, or 2 weeks or shorter. For example, the duration of the culturing step may be 3 days or longer and 2 weeks or shorter.

Although the culturing step may be performed either in vitro or in vivo, it is preferable that the culturing step is performed in vitro from the viewpoint of test convenience. When the culturing step is performed in vivo, the host cells mixed at the above mixing step may be transplanted into non-human animals, for instance, experimental animals such as rats and mice, and may be subjected to the extraction step described below after a certain period.

(Extraction Step)

In the extraction step, genomic DNA is extracted from the host cells after culturing in the above culturing step (and, optionally, host cells after the mixing step and before the culturing step) using a conventional method. The method for extracting genomic DNA extraction is known to those skilled in the art and may be referred to, for instance, the method described in Green and Sambrook, Molecular Cloning, 4th Ed (2012), Cold Spring Harbor Laboratory Press. Specifically, the genomic DNA can be extracted by a common phenol/chloroform extraction method or by using a commercially available kit such as the PureLink (registered trademark) Genomic DNA kit (Thermo Fisher Scientific) and the Mag Extractor™-Genome kit (TOYOBO). The extracted DNA can be used for PCR as it is or after purification. Incidentally, if the culturing step is performed in vivo, a suitable tissue(s) or organ(s) of the host cell-transplanted non-human animal are collected and then subjected to genomic DNA extraction using the above procedure.

(Quantification Step)

In the quantification step, the amount of the polynucleotide(s) in the genomic DNA extracted in the above extraction step is quantified based on the tag sequence(s) to give a quantified value. The "quantified value" is a measured value obtained by a quantification procedure. The quantified value may be an absolute value such as a volume or weight or may be a value relative to a reference value.

The quantification step may be conducted by using a quantification procedure known to those skilled in the art, such as a quantification procedure using a probe, semi-quantitative PCR using specific primers, or real-time PCR. The quantification step is not particularly limited but is preferably performed based on read counts obtained by next-generation sequencing from the viewpoint of quick and accurate operation. The next-generation sequencing is a method for acquiring sequence information by using a next-generation sequencer and is characterized in that compared to the Sanger method, a vast number of sequencing reactions are conducted in parallel and simultaneously (see, for example, Rick Kamps et al., Int. J. Mol. Sci., 2017, 18(2), p. 308 and Int. Neurourol. J., 2016, 20 (Suppl. 2), S76-83).

Typical steps of the next-generation sequencing are described below. First, sample preparation (step (1)) is performed. In the sample preparation, nucleic acid to be analyzed is enzymatically or mechanically fragmented depending on the read length of a next-generation sequencer. Next, in many cases, an adapter sequence that is necessary for a later sequencing step is added thereto. In addition, to analyze a specific gene region, the specific gene region may be enriched by PCR, etc. The gene region is enriched by, for instance, an amplification step of 4 to 12 cycles.

Subsequently, sequencing (step (2)) is performed. Details of the sequencing step vary depending on the kind of each next-generation sequencer. Typically, the nucleic acid is attached to a base plate via the adapter sequence; and sequencing reactions are performed using the adapter sequence as a priming site. Regarding details of the sequencing reactions, please see, for example, Rick Kamps et al. (supra).

Finally, data output (step (3)) is performed. This step gives a collection of sequence information obtained through the sequencing reactions. The output data may be further analyzed to lead more significant results.

The "read count", which may be used in the quantification step, refers to the amount of amplification of an amplification product having a specific sequence. In the quantification step of the present invention, the read count of a region containing a specific tag sequence as obtained by next-generation sequencing can be regarded as the relative amount of a gene of interest liked to the tag sequence and integrated in the genomic DNA.

In the quantification step of the present invention, it is preferable that, in particular, the nucleic acid region(s) containing tag sequence(s) subjected to PCR is subjected to next-generation sequencing. This PCR step makes it possible to not only add an adapter sequence which is necessary for next-generation sequencing but also enrich tag sequence-containing region(s), thereby increasing detection sensitivity. In addition, the same host endogenous PCR priming site and/or the same PCR priming site integrated into host cell genome may be preferably used to carry out a PCR reaction using the same primer. This enables the PCR reaction to be performed without affected by the difference in the amplification efficiency due to use of different primers, keeping the ratio before the amplification.

(Determination Step)

In the determination step, a relative cell count of each of the host cells having the respective polynucleotides after the culturing is determined based on the quantified values determined for the polynucleotides in the quantification step.

In the quantification step, each different polynucleotide in the genomic DNA is quantified, and thus not affected by the difference in level of expression, unlike in the case of quantifying mRNA or protein. Thus, a quantified value for each of the polynucleotides reflects a cell count of the host cells having the respective polynucleotides after the culturing.

Here, part of cells immediately after mixing in the mixing step may be collected as reference cells, and the cell count of the host cells after the culturing, which count is obtained by the determination step, may be normalized by using the cell count of the host cells immediately after the mixing. By doing so, a difference in the proportion between the numbers of cells mixed in the mixing step can be corrected.

(Comparison Step)

The comparison step is an optional step that can be included after the determination step in the evaluation method of the present invention. When the comparison step is included, genes of interest shall include a reference gene. As used herein, the "reference gene" means a gene as a reference for evaluating a function of gene(s) of interest. Examples of the kind include, but are not limited to, negative control genes that do not affect cell proliferation, namely that are known to have no transforming potential (e.g., wild-type genes without transforming potential) and positive control genes that are known to confer an positive or negative effect on cell proliferation (e.g., oncogenes, drug sensitive genes, drug resistant genes).

In the comparison step, the relative cell count of the host cells after the culturing is compared with the reference value, which count has been determined at the above determination step, wherein the reference value is defined as a relative cell count of a host cell comprising a polynucleotide comprising the reference gene after the culturing. Even in the absence of the reference gene, gene(s) of interest can be evaluated by, for instance, comparing it with other gene(s) of interest. However, when compared to the reference gene, gene(s) of interest can be evaluated more accurately.

(Evaluation Step)

The evaluation step is an optional step that can be included after the determination step or the comparison step in the evaluation method of the present invention. In the evaluation step, gene(s) of interest can be evaluated by comparing it with the reference value obtained in the comparison step or with other gene(s) of interest.

For instance, when the reference gene is the above negative control gene, when a relative cell count of a host cell comprising a polynucleotide comprising a gene of interest after culturing is higher than the reference value, the gene of interest may be evaluated as having transforming potential. Likewise, when the reference gene is the above positive control gene, when a relative cell count of a host cell comprising a polynucleotide comprising a gene of interest after culturing is comparable to the reference value, the gene of interest may be evaluated as having transforming potential. In these embodiments, the evaluation method of the present invention may be used as a method for identifying an oncogene (candidate).

Further, when the proliferation potential of gene(s) of interest is evaluated, for instance, based on read counts obtained by next-generation sequencing, the proliferation score calculated by the following calculation equation may be used to identify an oncogene (candidate).

$$\text{Proliferation score of gene } A \text{ of interest} = (A_X \times T_0)/(A_0 \times T_X)$$

[wherein $A_X$=the read count of a tag sequence added to gene A of interest in cells collected at Day X;

$T_0$=the total read count of all tag sequences in cells collected at Day 0;

$A_0$=the read count of the tag sequence added to gene A of interest in the cells collected at Day 0; and $T_X$=the total read count of all tag sequences in the cells collected at Day X.]

(The proliferation score indicates that the higher the score is, the higher the proliferation potential (transforming potential) of the gene of interest is. Here, Day 0 represents the results before culturing; and Day X represents the results after X days of culturing. (the same applies to the following))

Usually, when cells are cultured under a differentiation-inducing condition, the differentiation is induced and the cells stop their growth. Thus, when the culturing step is performed under a differentiation-inducing condition and cells having a mutation are found to proliferate even under the differentiation-inducing condition, the mutation can be evaluated as a mutation that suppresses the differentiation, for instance, a mutation suppress the differentiation having transforming potential.

Specifically, for instance, when the reference gene is the above negative control gene known to not affect differentiation, when a relative cell count of a host cell comprising a polynucleotide comprising a gene of interest after culturing under a differentiation-inducing condition is higher than the reference value, the gene of interest may be evaluated as having an ability to suppress the differentiation. Likewise, when the reference gene is the above positive control gene known to affect differentiation, when a relative cell count of a host cell comprising a polynucleotide comprising a gene of interest after culturing under a differentiation-inducing condition is comparable to the reference value, the gene of interest may be evaluated as having transforming potential. In these embodiments, the evaluation method of the present invention may be used as a method for identifying a (candidate) gene that suppresses differentiation.

Further, when the proliferation potential of gene(s) of interest is evaluated, for instance, based on read counts obtained by next-generation sequencing, the score about an ability to suppress differentiation as calculated by the following calculation equation may be used to identify a (candidate) gene that suppresses differentiation.

$$\text{Score about an ability to suppress differentiation by gene } A \text{ of interest} = (AI_X \times T_X)/(A_X \times TI_X)$$

[wherein $AI_X$=the read count of a tag sequence added to gene A of interest in cells collected at Day X after differentiation induction;

$T_X$=the total read count of all tag sequences in cells collected at Day X;

$A_X$=the read count of the tag sequence added to gene A of interest in the cells collected at Day X; and $TI_X$=the total read count of all tag sequences in the cells collected at Day X after differentiation induction.]

(The score about an ability to suppress differentiation indicates that the higher the score is, the higher the ability to suppress differentiation by the gene of interest is.)

Furthermore, the evaluation method of the present invention may be used to evaluate drug sensitivity or resistance. For instance, if read counts obtained by next-generation sequencing are used to evaluate drug sensitivity, the drug sensitivity score can be calculated by the following calculation equation:

$$\text{Drug sensitivity score of gene } A \text{ of interest} = (AD_X \times T_X)/(A_X \times TD_X)$$

wherein $A_X$=the read count of a tag sequence added to gene A of interest in cells collected at Day X;

$T_X$=the total read count of all tag sequences in the cells collected at Day X;

$AD_X$=the read count of the tag sequence added to gene A of interest in cells collected at Day X after drug administration; and $TD_X$=the total read count of all tag sequences in the cells collected at Day X after drug administration.

(The drug sensitivity score indicates viability of a cell having the gene of interest introduced therein at that drug concentration. The higher the score is, the lower the drug sensitivity (the higher the drug resistance) is.)

When whether a gene of interest is sensitive or resistant to a drug is evaluated, the kind of the drug is not limited. Preferable examples of the drug include anti-cancer drugs such as low-molecular-weight compounds and/or antibodies. Examples of the low-molecular-weight compound acting as an anti-cancer drug include EGFR tyrosine kinase inhibitors (TKIs) such as gefitinib, erlotinib, afatinib, osimertinib, rociletinib, crizotinib, and alectinib. Examples of the antibody acting as an anti-cancer drug include EGFR antibodies such as cetuximab.

In an embodiment of the present invention, gene(s) of interest is an oncogene. In this embodiment, the evaluation method of the present invention may include a step of evaluating whether an oncogene is sensitive (or resistant) to the anti-cancer drug based on the relative cell count after the culturing, while the culturing step is performed in the presence of an anti-cancer drug.

The sensitivity or resistance to the anti-cancer drug may be defined by comparing them to those of a reference gene (e.g., a wild-type gene) or those of other genes of interest. For instance, either a drug sensitive gene or a drug resistant gene may be used as the reference gene. Also, the drug sensitivity or resistance can be evaluated based on cell viability at a specific drug concentration(s) without including the reference gene.

In addition, the drug sensitivity or resistance may be determined based on the viability at a drug concentration after the drug concentration is suitably selected in view of the kind of the drug and the in vivo level of the drug concentration, etc. When the anti-cancer drug is the above low-molecular-weight compound, the drug sensitivity or resistance can be evaluated based on cell viabilities at the concentration of for instance, from 0.0001 µM to 10 µM, from 0.0005 µM to 5 µM, from 0.001 µM to 1 µM, from 0.005 µM to 0.5 µM, or from 0.01 µM to 0.1 µM. When the anti-cancer drug is the above antibody, the drug sensitivity or resistance can be evaluated based on cell viabilities at the concentration of, for instance, from 0.001 μg/mL to 100 μg/mL, from 0.01 μg/mL to 10 μg/mL, or from 0.1 μg/mL to 1 μg/mL.

When the cell survival at these drug concentrations is high, for example, the cell viabilities is, for instance, 50% or higher, 60% or higher, 70% or higher, 80% or higher, 90% or higher, or 100%, the cell having the gene of interest is determined to be resistant to the drug. When the cell survival at these drug concentrations is low and the cell viabilities is, for instance, 50% or higher, 50% or lower, 40% or lower, 30% or lower, 20% or lower, 10% or lower, or 0%, the cell having the gene of interest is determined to be sensitive to the drug.

As used herein, the sensitivity can be further divided into the "strict sensitivity", in which the probability of the drug to exert its effect is high, and the "partial sensitivity", in which the probability of the drug to exert its effect is poorer than that of the strict sensitivity. Whether a gene of interest is strictly sensitive, partially sensitive, or resistant to a drug can be defined based on, for instance, IC90 (i.e., a drug concentration at which growth of cells are inhibited by 90%) as follows.

For instance, regarding gefitinib, erlotinib, and osimertinib, the case of IC90<0.1 μM can be defined as strictly sensitive; the case of 0.1 μM≤IC90≤0.5 μM can be defined as partially sensitive; and the case of IC90>0.5 μM can be defined as resistant. In addition, regarding afatinib, the case of IC90<0.005 μM can be defined as strictly sensitive; the case of 0.005 μM≤IC90≤0.01 μM can be defined as partially sensitive; and the case of IC90>0.01 μM can be defined as resistant. Regarding rociletinib, the case of IC90<0.1 μM can be defined as strictly sensitive; the case of 0.1 μM≤IC90≤1 μM can be defined as partially sensitive; and the case of IC90>1 μM can be defined as resistant. Regarding cetuximab, the case of IC90<1 μg/mL can be defined as strictly sensitive; the case of 1 μg/mL≤IC90≤100 μg/mL can be defined as partially sensitive; and the case of IC90>100 μg/mL can be defined as resistant.

In one embodiment of the present invention, gene(s) of interest is a tumor suppressor gene such as the BRCA1 gene or BRCA2 gene. In this embodiment, host cells may be cells deficient in a gene of interest such as a tumor suppressor gene. Also, in this embodiment, the culturing step may be performed under treatment which causes the damage to the host cells that can be repaired by the tumor suppressor gene. Examples of the treatment which causes the damage to the host cells that can be repaired by the tumor suppressor gene include: treatment with an agent such as PARP (poly(ADP-ribose)polymerase) inhibitor or cytotoxic anti-cancer drug (such as a platinum anti-cancer drug cisplatin, carboplatin); and radiation treatment. Examples of the PARP inhibitor include olaparib, niraparib, veliparib, and talazoparib. In this embodiment, the evaluation method of the present invention may include a step of evaluating a tumor suppressor gene based on the relative cell count after the culturing. For instance, a cell having a functional tumor suppressor gene introduced has a repair function, and thus the number of cells is not decreased even when adding an agent such as the PARP inhibitor. By contrast, a cell having a function-deficient tumor suppressor gene introduced has no repair function, and thus the number of cells is decreased when adding an agent such as the PARP inhibitor. According to such criteria, a tumor suppressor gene may be evaluated based on the relative cell count after the culturing.

<Method for Determining Anti-Cancer Drug>

In one aspect, the present invention relates to a method for determining an anti-cancer drug. The method for determining an anti-cancer drug according to the present invention comprises the steps of performing the above method for evaluating drug sensitivity for a plurality of anti-cancer drugs; and determining an anti-cancer drug effective for an oncogene based on the results obtained. The culturing step of the method for evaluating drug sensitivity may be conducted in the presence of a plurality of drugs, so that the plurality of anti-cancer drugs can be evaluated at once. This makes it possible to evaluate whether a gene of interest is sensitive to a combination drug or combination therapy. In addition, the method for evaluating drug sensitivity may be independently conducted per drug, so that the sensitivity regarding each drug can be independently evaluated. This enables each drug sensitivity to be compared so as to determine a more sensitive drug. In this case, it is preferable that the drugs have different mechanisms of action in order to broadly examine whether each gene is sensitive to various drugs. Especially, the present inventors have found that there is a big difference between the antibody sensitivity and the low-molecular-weight compound sensitivity of each oncogene. Hence, a more suitable drug can be selected by evaluating both of the antibody sensitivity and the drug sensitivity.

<Markers for Detecting Cancer>

In one aspect, the present invention relates to a marker for detecting cancer. A marker for detecting cancer means a factor as an indicator for detecting cancer. Examples of cancer detected with a marker for detecting cancer according to the present invention include, but are not limited to, brain tumor, pharyngeal cancer, thyroid cancer, lung cancer, breast cancer, esophageal cancer, gastric cancer, liver cancer, pancreatic cancer, renal cancer, small intestine cancer, large intestine cancer, bladder cancer, prostate cancer, cervical cancer, ovarian cancer, lymphoma, and melanoma, preferably, lung cancer.

In one embodiment, a marker for detecting cancer according to the present invention, preferably a marker for detecting lung cancer, consists of an EGFR protein having a mutation selected from the group consisting of A767V, A871G, E865K, G874S, H304Y, H773Y, L838P, P741L, 511531, S752-1759del, V786M, and V802I, or a polynucleotide encoding the protein.

As used herein, the EGFR protein preferably comprises, but is not limited to, the amino acid sequence of the human EGFR protein set forth in SEQ ID NO: 1. In addition, a polynucleotide encoding the EGFR protein preferably comprises, but is not limited to, the nucleotide sequence set forth in SEQ ID NO: 2, which encodes the amino acid sequence set forth in SEQ ID NO: 1.

As used herein, a substitution mutation is denoted as "$X_1 a_1 X_2$". This means that when the start methionine in the amino acid sequence of a protein is set to position 1, amino acid $X_1$ at position $a_1$ is substituted with amino acid $X_2$. For instance, the above A767V of the EGFR protein means that leucine at position 767 of the amino acid sequence set forth in SEQ ID NO: 1 is substituted with arginine. Incidentally, single letter amino acid code herein follows standard amino acid lettering.

In addition, as used herein, an insertion mutation is denoted as "$X_1 a_1 - X_2 a_2 ins X_3$". This means that amino acid $X_3$ is inserted (ins: insert) between amino acid $X_1$ at position $a_1$ and amino acid $X_2$ at position $a_2$ of a protein. Here, $X_3$ may be two or more amino acid residues. For instance, K745-E746insVPVAIK of the EGFR protein means that a valine, a proline, a valine, an alanine, an isoleucine, and a lysine are inserted between a lysine at position 745 and a glutamic acid at position 746 of the amino acid sequence set forth in SEQ ID NO: 1.

In addition, as used herein, a deletion mutation is denoted as "$X_1a_1$-$X_2a_2$del" or "del$X_1a_1$-$X_2a_2$". This means that a portion from (amino acid $X_1$ at) position $a_1$ to (amino acid $X_2$ at) position $a_2$ of a protein is deleted (del: delete). For instance, L747-A750del of the EGFR protein means that a leucine at position 747 to an alanine at position 750 of the amino acid sequence set forth in SEQ ID NO: 1 are deleted.

As used herein, a deletion substitution mutation is denoted as "$X_1a_1$-$X_2a_2$>$X_3$". This means that amino acid $X_1$ at position $a_1$ to amino acid $X_2$ at position $a_2$ of a protein are substituted with amino acid $X_3$. Amino acid $X_3$ may be two or more amino acid residues. Here, the "deletion substitution mutation" means a mutation by which one or two or more amino acids of an original amino acid sequence are substituted with one or two or more different amino acids. The deletion substitution mutation is distinguishable from a regular substitution mutation because the number of amino acid residues deleted differs from the number of amino acid residues substituted. For instance, E709-T710>D of the EGFR protein means that a glutamic acid at position 709 to a threonine at position 710 of the amino acid sequence set forth in SEQ ID NO: 1 are deleted and substituted with an aspartic acid; and E746-A750>IP of the EGFR protein means that a glutamic acid at position 746 to an alanine at position 750 of the amino acid sequence set forth in SEQ ID NO: 1 are deleted and substituted with an isoleucine and a proline.

In one aspect, a marker for detecting cancer according to the present invention consists of an EGFR protein having a compound mutation or a polynucleotide encoding the protein. The compound mutation refers to a plurality of different mutations present in one wild-type gene.

As used herein, a compound mutation containing two or more mutations is represented by a combination of the above mutation denotations, like "$X_1a_1X_2$ and $X_3a_2X_4$" or "$X_1a_1X_2$+$X_3a_2X_4$". This means that amino acid $X_1$ at position $a_1$ of a protein is substituted with amino acid $X_2$ and amino acid $X_3$ at position $a_2$ is substituted with amino acid $X_4$. For instance, R108K and L858R of the EGFR protein means that R (arginine) at position 108 of the amino acid sequence set forth in SEQ ID NO: 1 is substituted with K and L at position 858 is substituted with R. The compound mutation includes: a cis type, in which a gene on the same chromosome contains a plurality of mutations; and a trans type, in which an allele on a different chromosome contains a different mutation. As used herein, the cis-type compound mutation is represented by (cis) and the trans-type compound mutation is represented by (trans).

In one embodiment, a marker for detecting cancer according to the present invention, preferably a marker for detecting lung cancer, consists of an EGFR protein having a compound mutation selected from the group consisting of L62R and G719S (trans), R108K and L858R (trans), A216T and E746-5752>V (cis), A216T and E746-5752>V (trans), A289T and L858R (cis), A289T and L858R (trans), V292L and L858R (cis), V292L and L858R (trans), 5306L and L858R (cis), 5306L and L858R (trans), L7031 and L858R (cis), L7031 and L858R (trans), I706T and G719A (cis), I706T and G719A (trans), E709A and G719C (cis), E709A and G719C (trans), E709A and G719S (cis), E709A and G719S (trans), E709A and L858R (cis), E709A and L858R (trans), E709G and L858R (trans), E709K and L858R (cis), E709K and L858R (trans), E709V and L858R (cis), E709V and L858R (trans), K714R and L858R (cis), K714R and L858R (trans), L718Q and L858R (cis), L718Q and L858R (trans), S720F and L858R (cis), S720F and L858R (trans), I744M and L858R (cis), S768I and G719A (cis), S768I and G719A (trans), S768I and G719C (cis), S768I and G719C (trans), S768I and G719S (cis), S768I and G719S (trans), S768I and L858R (cis), S768I and L858R (trans), R776C and L858R (cis), R776C and L858R (trans), R776G and L858R (cis), R776G and L858R (trans), T790M and C797S (cis), T790M and E746-A750del (cis), T790M and E746-A750del (trans), T790M and G719A (cis), T790M and G719A (trans), T790M and L858R (cis), T790M and L858R (trans), L833V and L858R (cis), L833V and L858R (trans), L838V and L858R (cis), L838V and L858R (trans), V843I and L858R (cis), V843I and L858R (trans), L861Q and G719A (cis), L861Q and G719A (trans), L861Q and L858R (cis), L861Q and L858R (trans), L861R and G719A (cis), L861R and G719A (trans), A871G and L858R (cis), A871G and L858R (trans), A1118T and E746-A750del (cis), and A1118T and E746-A750del (trans), or a polynucleotide encoding the protein.

In one embodiment, a marker for detecting cancer according to the present invention consists of a BRCA2 protein having a mutation selected from the group consisting of: R2659G, N3124I, L2604P, W31C, E2663K, W2626R, D3073G, G2609D, P2329L, D2913H, P2639L, S3291C, D23V, I2664M, K485*, L997*, Q1502*, K1984*, C2535*, and W2970*, or, preferably R2659G, N3124I, L2604P, W31C, E2663K, W2626R, D3073G, G2609D, and P2329L, or a polynucleotide encoding the protein.

As used herein, the BRCA2 protein preferably comprises, but is not limited to, the amino acid sequence of the human BRCA2 protein set forth in SEQ ID NO: 13. In addition, a polynucleotide encoding the BRCA2 protein preferably comprises, but is not limited to, the nucleotide sequence set forth in SEQ ID NO: 14, which encodes the amino acid sequence set forth in SEQ ID NO: 13.

As used herein, a nonsense mutation is denoted as "$X_1a_1$*". This means that when the start methionine in the amino acid sequence of a protein is set to position 1, nucleotides encoding amino acid $X_1$ at position $a_1$ are substituted with nucleotides encoding a stop codon. For instance, the above K485* of the BRCA2 protein means that nucleotides encoding a lysine at position 485 of the amino acid sequence set forth in SEQ ID NO: 13 are substituted with nucleotides encoding a stop codon.

<COL1A2/DCAF6 Fusion Protein>

In one aspect, the present invention relates to a fusion protein comprising a COL1A2 (collagen type I alpha 2) protein and a DCAF6 (DDB1 and CUL4 associated factor 6) protein or a polynucleotide encoding the fusion protein. The origin of each of the COL1A2 protein and the DCAF6 is not limited and is preferably a mammal. Examples of the mammal include primates (e.g., a human, chimpanzee), experimental animals (e.g., a rat, mouse), domestic animals (e.g., a pig, cow, horse, sheep, goat), and pets (e.g., a dog, cat), preferably, a human.

The COL1A2 protein may be preferably a polypeptide containing an amino acid sequence of the human COL1A2 protein set forth in SEQ ID NO: 3, or an amino acid sequence having, for instance, 70% or more, 80% or more, preferably 90% or more, 95% or more, 97% or more, 98% or more, or 99% or more identity to the amino acid sequence set forth in SEQ ID NO: 3. In addition, the COL1A2 protein may be a polypeptide containing an amino acid sequence having one or more amino acid additions, deletions, and/or substitutions in the amino acid sequence set forth in SEQ ID NO: 3. A polynucleotide encoding the COL1A2 protein may be preferably a polynucleotide containing a nucleotide sequence set forth in SEQ ID NO: 4 encoding the amino acid sequence set forth in SEQ ID NO: 3, or a nucleotide sequence having, for instance, 70% or more, 80% or more, preferably 90% or more, 95% or more, 97% or more, 98% or more, or 99% or more identity to the nucleotide sequence set forth in SEQ ID NO: 4. In addition, the polynucleotide encoding the COL1A2 protein may be a polynucleotide containing a nucleotide sequence having one or more nucleotide additions, deletions, and/or substitutions in the nucleotide sequence set forth in SEQ ID NO: 4.

As used herein, the identity value about amino acid sequences and nucleotide sequences is indicated as a value calculated by software (e.g., FASTA, DANASYS, and BLAST), which calculates identity among a plurality of sequences, in a default setting. For the details of the identity-calculating method, see, for example, Altschul et al., Nuc. Acids. Res. 25, 3389-3402, 1977 and Altschul et al., J. Mol. Biol. 215, 403-410, 1990. Meanwhile, the range of "one or more" herein include 1 to 10, preferably 1 to 7, more preferably 1 to 5, and still more preferably 1 to 3 or 1 or 2.

The DCAF6 protein may be preferably a polypeptide containing an amino acid sequence of the human DCAF6 protein set forth in SEQ ID NO: 5, or an amino acid sequence having, for instance, 70% or more, 80% or more, preferably 90% or more, 95% or more, 97% or more, 98% or more, or 99% or more identity to the amino acid sequence set forth in SEQ ID NO: 5. In addition, the DCAF6 protein may be a polypeptide containing an amino acid sequence having one or more amino acid additions, deletions, and/or substitutions in the amino acid sequence set forth in SEQ ID NO: 5. A polynucleotide encoding the DCAF6 protein may be preferably a polynucleotide containing a nucleotide sequence set forth in SEQ ID NO: 6 encoding the amino acid sequence set forth in SEQ ID NO: 5, or a nucleotide sequence having, for instance, 70% or more, 80% or more, preferably 90% or more, 95% or more, 97% or more, 98% or more, or 99% or more identity to the nucleotide sequence set forth in SEQ ID NO: 6. In addition, the polynucleotide encoding the DCAF6 protein may be a polynucleotide containing a nucleotide sequence having one or more nucleotide additions, deletions, and/or substitutions in the nucleotide sequence set forth in SEQ ID NO: 6.

A fusion protein comprising a COL1A2 protein and a DCAF6 protein is not limited as long as the fusion protein can suppress differentiation. Preferably, a portion of the COL1A2 protein is included at the N-terminus of the fusion protein and a portion of the DCAF6 protein is included at the C-terminus of the fusion protein.

A fusion protein comprising a COL1A2 protein and a DCAF6 protein may be preferably a polypeptide containing an amino acid sequence of the human COL1A2/human DCAF6 fusion protein set forth in SEQ ID NO: 7, or an amino acid sequence having, for instance, 70% or more, 80% or more, preferably 90% or more, 95% or more, 97% or more, 98% or more, or 99% or more identity to the amino acid sequence set forth in SEQ ID NO: 7. In addition, the COL1A2/DCAF6 fusion protein may be a polypeptide containing an amino acid sequence having one or more amino acid additions, deletions, and/or substitutions in the amino acid sequence set forth in SEQ ID NO: 7. A polynucleotide encoding the COL1A2/DCAF6 fusion protein may be preferably a polynucleotide containing a nucleotide sequence set forth in SEQ ID NO: 8 encoding the amino acid sequence set forth in SEQ ID NO: 7, or a nucleotide sequence having, for instance, 70% or more, 80% or more, preferably 90% or more, 95% or more, 97% or more, 98% or more, or 99% or more identity to the nucleotide sequence set forth in SEQ ID NO: 8. In addition, the polynucleotide encoding the COL1A2/DCAF6 fusion protein may be a polynucleotide containing a nucleotide sequence having one or more nucleotide additions, deletions, and/or substitutions in the nucleotide sequence set forth in SEQ ID NO: 8.

The COL1A2/DCAF6 fusion protein can suppress differentiation, for example, can suppress differentiation into myocytes, and/or may have transforming potential due to the ability to suppress differentiation. Thus, the fusion protein or a polynucleotide encoding the fusion protein may be used as a marker for detecting a mutation that suppresses differentiation or a marker for detecting cancer such as lung cancer. The marker for detecting a mutation that suppresses differentiation means a factor as an indicator for detecting a mutation that suppresses differentiation.

<Drug Sensitive or Resistant Markers>

In one aspect, the present invention relates to a drug sensitive marker or drug resistant marker. The drug sensitive marker means a factor as an indicator for evaluating drug sensitivity. The drug resistant marker means a factor as an indicator for evaluating drug resistance. The drug sensitive marker or drug resistant marker of the present invention can be used to select a suitable drug(s).

The drug sensitive marker or resistant marker may be determined by comparing them to, for instance, a reference gene(s) (e.g., a wild-type gene) or other genes of interest in accordance with the evaluation method of the present invention. For instance, the drug sensitive or resistant marker for the EGFR protein may be determined using a wild-type (WT) as a reference based on FIGS. 5 and 6 of the specification of the present application. For instance, regarding gefitinib, a protein having a mutation that confers higher cell viability than WT or a polynucleotide encoding the protein may be used as a gefitinib-sensitive marker based on FIGS. 5 and 6. Specific examples of such a mutation include mutations selected from the group consisting of L62R, R108K, A289D, H304Y, P596L, G719C, G719S, S720F, K745-E746insVPVAIK, E746-A750>IP, E746-P753>VS, E746-T751>V, L747-A750>P, L747-A750del, L747-P753>Q, L747-P753>S, L747-T751>P, L747-T751>S, L747-T751del, T751-1759>N, 5752-1759del, V765M, R776C, R776H, V786M, V802I, R831H, R831L, V834M, H835L, P848L, L858R, A864T, A871G, A871T, G873E, G874S, A1118T, and S1153I. By contrast, regarding gefitinib, a protein having a mutation that confers lower cell viability than WT or a polynucleotide encoding the protein may be used as a gefitinib-resistant marker based on FIGS. 5 and 6. Specific examples of such a mutation include mutations selected from the group consisting of E709-T710>D, E709A, E709G, V769-D770insASV, V769L, D770-N771insSVD, N771-P772insN, H773-V774insH, H773-V774insPH, H773L, V774-C775insHV, V774M, T790M, T7900M and C797S, V851I, and T854A. Likewise, based on FIGS. 5 and 6, it is possible to determine a marker that is sensitive or resistant to a drug including erlotinib, afatinib, osimertinib, and rociletinib.

In addition, the drug sensitivity or resistance may be determined based on the viability at a drug concentration after the drug concentration is suitably selected in view of the kind of the drug and the in vivo level of the drug concentration, etc. When the anti-cancer drug is the above low-molecular-weight compound, the drug sensitivity or resistance can be evaluated based on cell viabilities at the concentration of for instance, from 0.0001 µM to 10 µM, from 0.0005 µM to 5 µM, from 0.001 µM to 1 µM, from 0.005 µM to 0.5 µM, or from 0.01 µM to 0.1 µM. When the anti-cancer drug is the above antibody, the drug sensitivity or resistance can be evaluated based on cell viabilities at the concentration of, for instance, from 0.001 μg/mL to 100 μg/mL, from 0.01 μg/mL to 10 μg/mL, or from 0.1 μg/mL to 1 μg/mL. When the cell survival at these drug concentrations is high, for example, the cell viabilities is, for instance, 50% or higher, 60% or higher, 70% or higher, 80% or higher, 90% or higher, or 100%, the cell having the gene of interest is determined to be resistant to the drug. When the cell survival at these drug concentrations is low and the cell viabilities is, for instance, 50% or lower, 40% or lower, 30% or lower, 20% or lower, 10% or lower, or 0%, the cell having the gene of interest is determined to be sensitive to the drug.

Figures 1, 5:
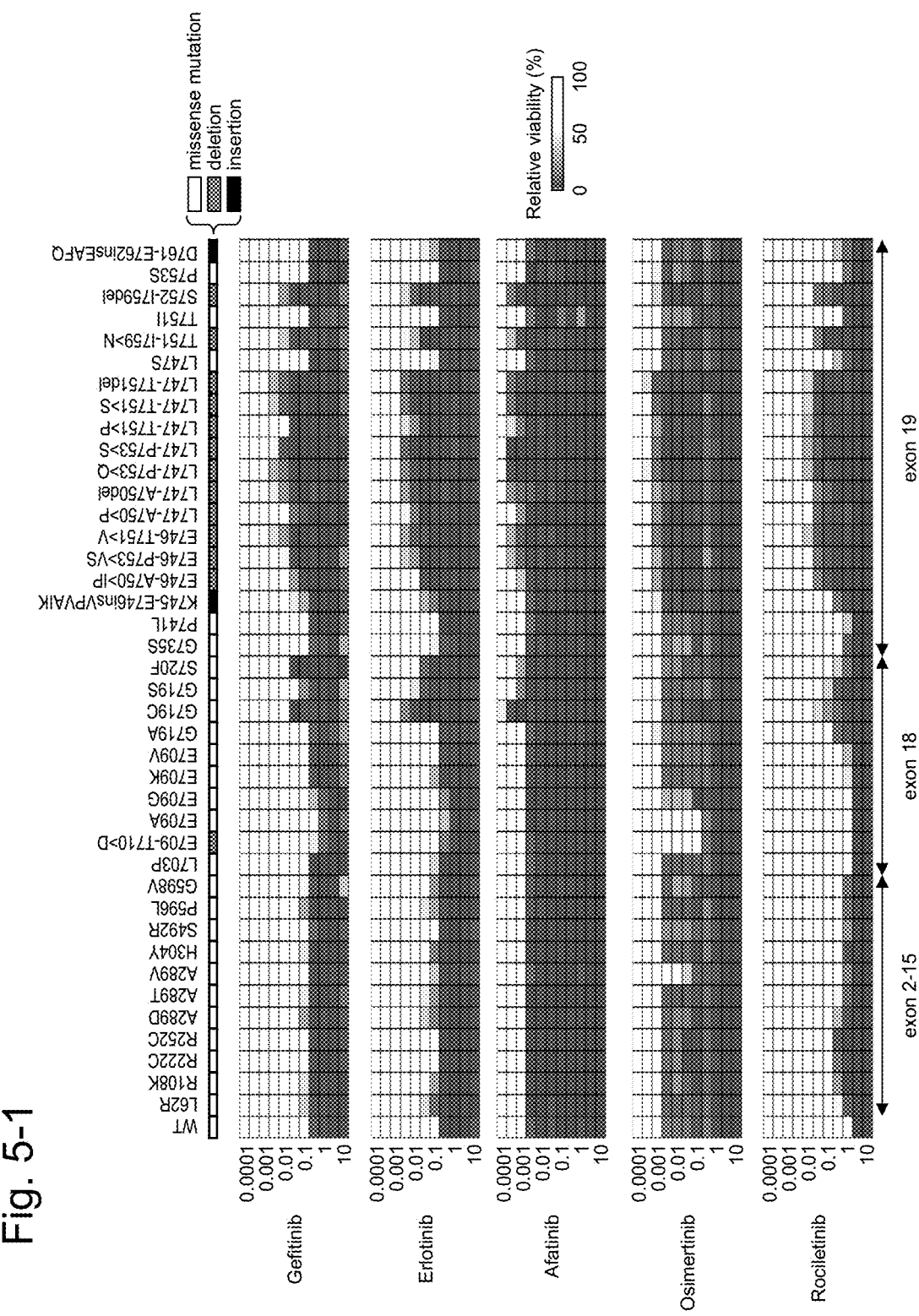
Figures 2, 5:
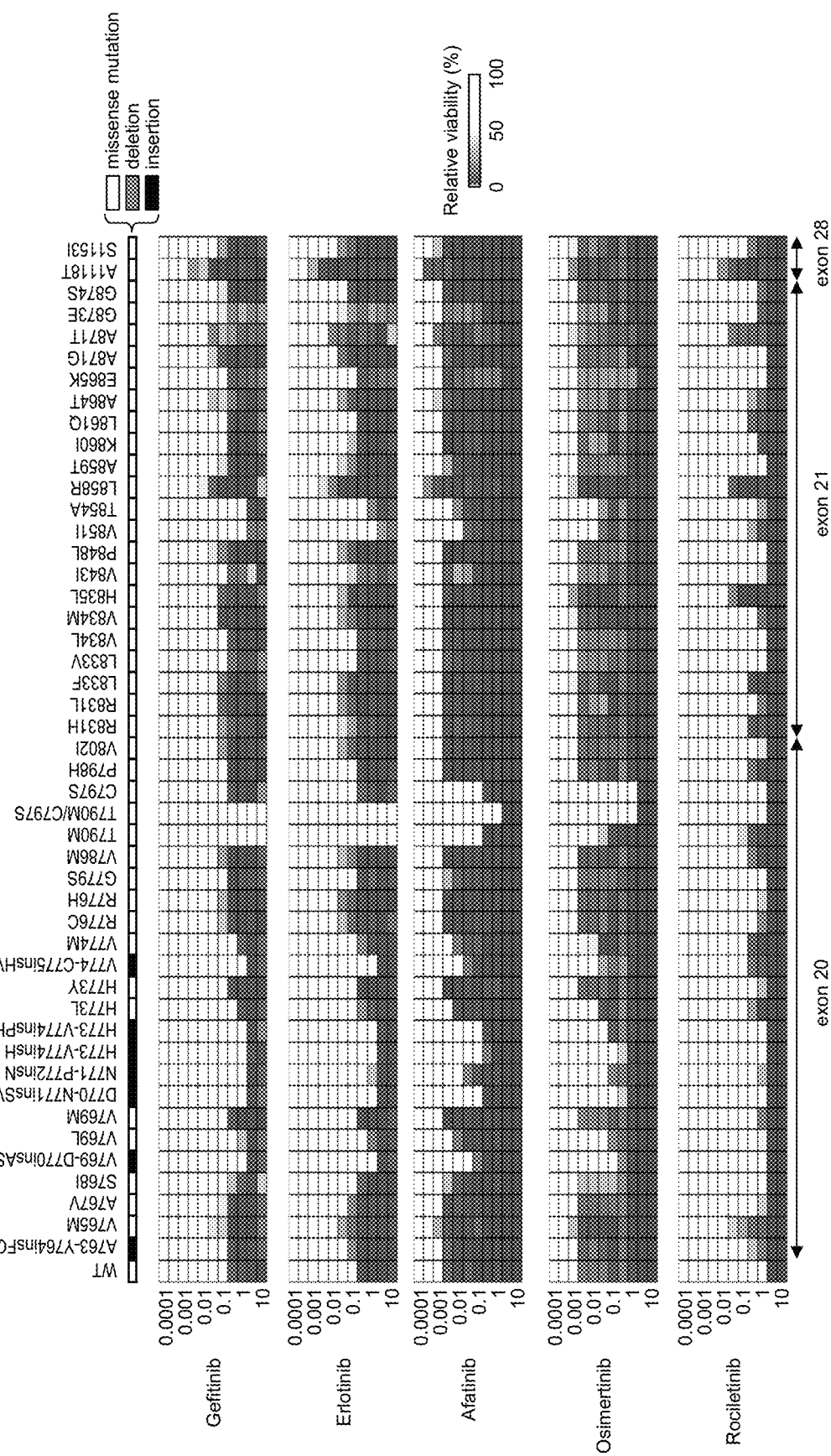
Figures 1, 6:
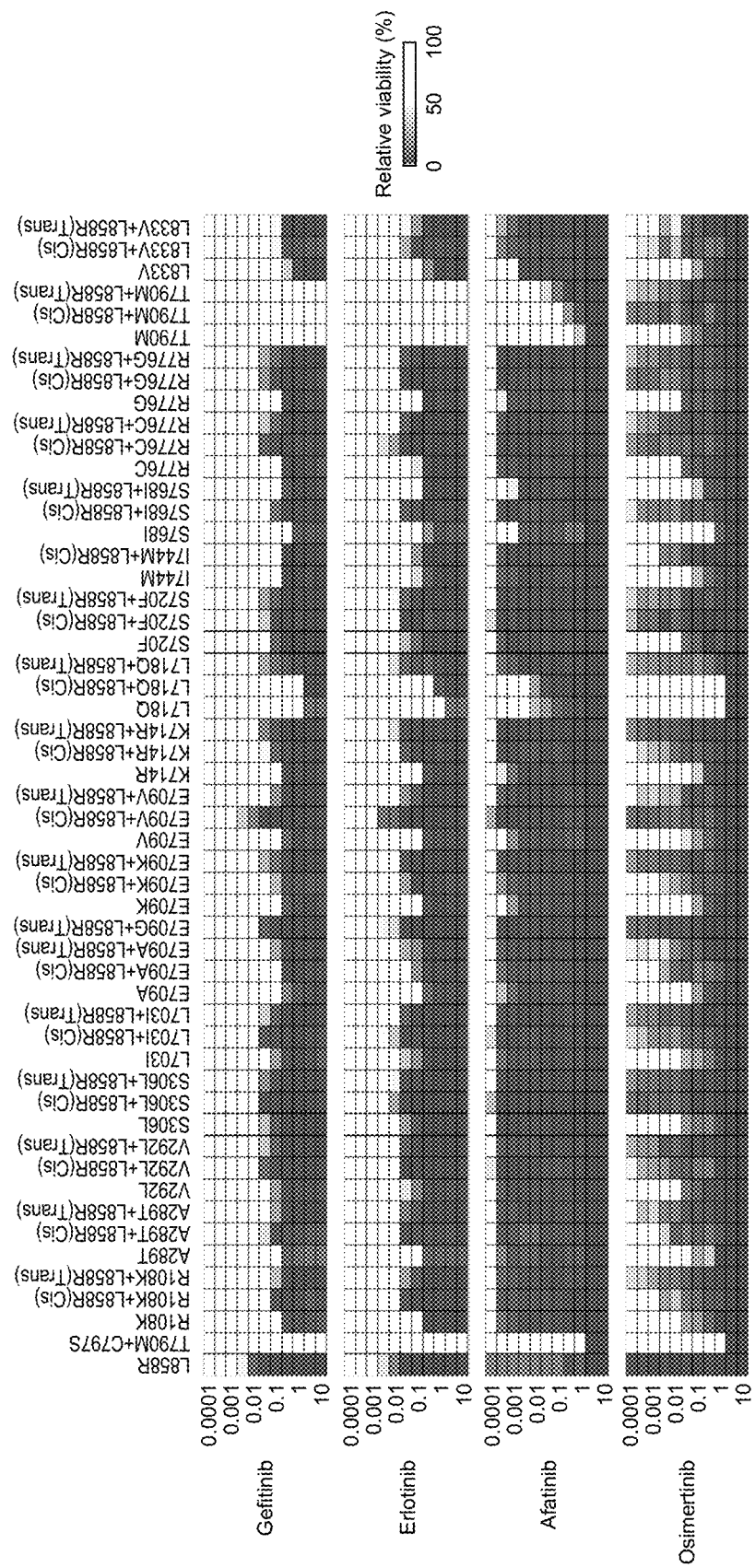
Figures 2, 6:
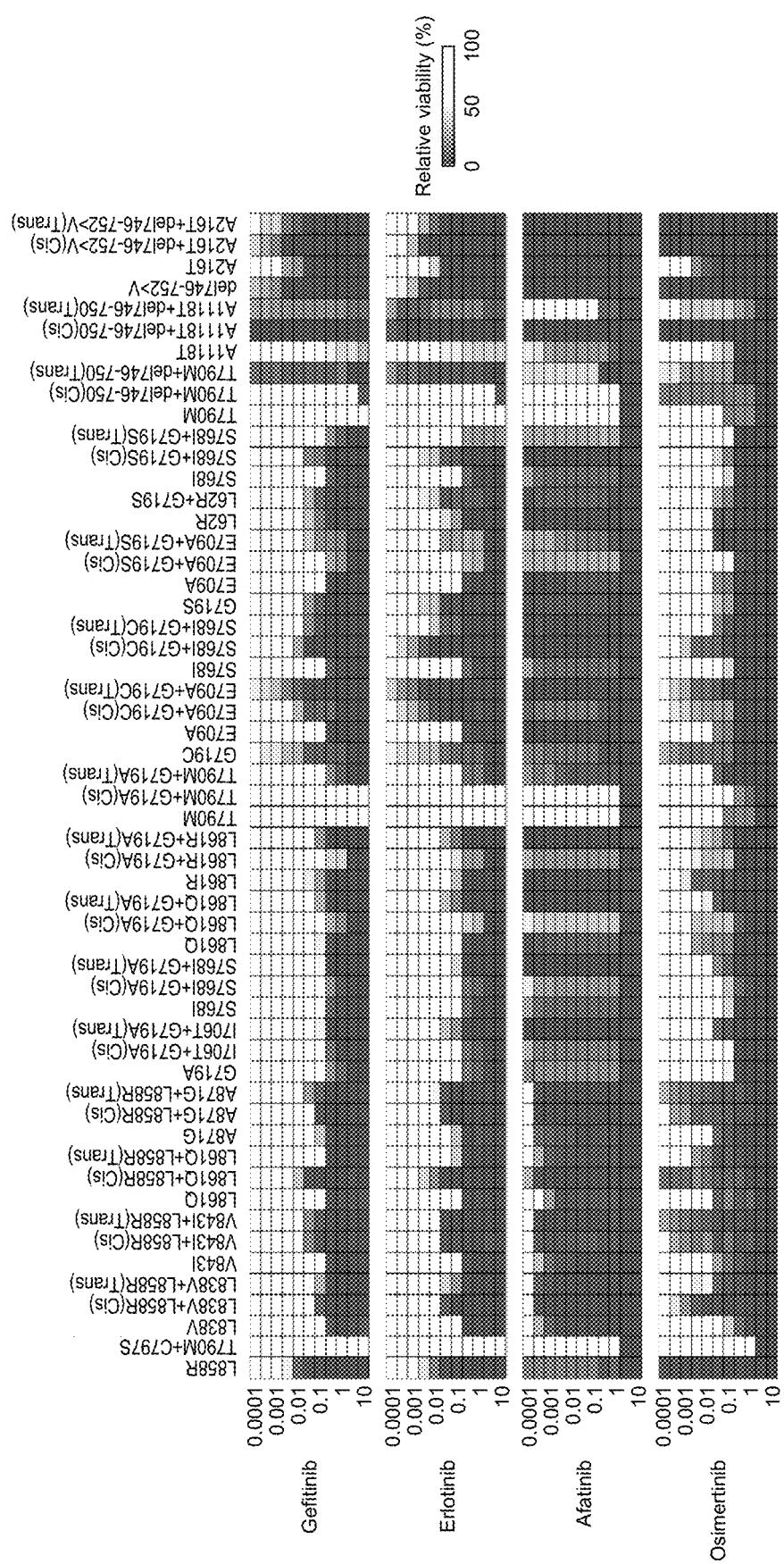

For instance, regarding gefitinib, a protein having each mutation that confers low cell viability at, for example, 0.05 μM, 0.1 μM, or 0.5 μM, preferably 0.1 μM or a polynucleotide encoding the protein may be used as a gefitinib-sensitive marker based on FIGS. 5 and 6. Specific examples of such a mutation include mutations selected from the group consisting of L62R, R108K, A289D, H304Y, P596L, G719C, G719S, S720F, K745-E746insVPVAIK, E746-A750>IP, E746-P753>VS, E746-T751>V, L747-A750>P, L747-A750del, L747-P753>Q, L747-P753>S, L747-T751>P, L747-T751>S, L747-T751del, T751-1759>N, S752-1759del, V765M, R776C, R776H, V786M, V802I, R831H, R831L, V834M, H835L, P848L, L858R, A864T, A871G, A871T, G873E, G874S, A1118T, and S1153I which are colored in FIG. 5.

By contrast, regarding gefitinib, a protein having each mutation that confers high cell viability at, for example, 0.1 μM, 0.5 μM, or 1 μM, preferably 0.5 μM or a polynucleotide encoding the protein may be used as a gefitinib-resistant marker based on FIGS. 5 and 6. Specific examples of such a mutation include mutations selected from the group consisting of E709-T710>D, E709A, V769-D770insASV, V769L, D770-N771insSVD, N771-P772insN, H773-V774insH, H773-V774insPH, H773L, V774-C775insHV, V774M, T790M, T7900M and C797S, V851I, and T854A which are not colored in FIG. 5.

Likewise, it is possible to determine, a marker that is sensitive or resistant to a drug including erlotinib, afatinib, osimertinib, and rociletinib based on FIGS. 5 and 6. For instance, it is possible to use, as a marker that is sensitive to each drug, a protein having a mutation selected from the mutations colored at 0.05 μM, 0.1 μM, or 0.5 μM, preferably 0.1 μM in FIG. 5 or 6 or a polynucleotide encoding the protein for erlotinib; the mutation selected from the mutations colored at 0.0005 μM, 0.001 μM, or 0.005 μM, preferably 0.001 μM in FIG. 5 or 6 or a polynucleotide encoding the protein for afatinib and osimertinib; and the mutation selected from the mutations colored at 0.5 μM, 1 μM, or 5 μM, preferably 1 μM n FIG. 5 or 6 or a polynucleotide encoding the protein for the rociletinib.

In addition, it is possible to use, as a marker that is resistant to a drug, a protein having a mutation, for example, the mutation selected from the mutations not colored at 0.1 μM, 0.5 μM, or 1 μM, preferably 0.5 μM in FIG. 5 or 6 or a polynucleotide encoding the protein for erlotinib; the mutation selected from the mutations not colored at 0.001 μM, 0.005 μM, or 0.01 μM, preferably 0.005 μM in FIG. 5 or 6 or a polynucleotide encoding the protein for afatinib and osimertinib; and the mutation selected from the mutations not colored at 1 μM, 5 μM, or 10 μM, preferably 5 μM in FIG. 5 or 6 or a polynucleotide encoding the protein for rociletinib.

Figures 1, 8:
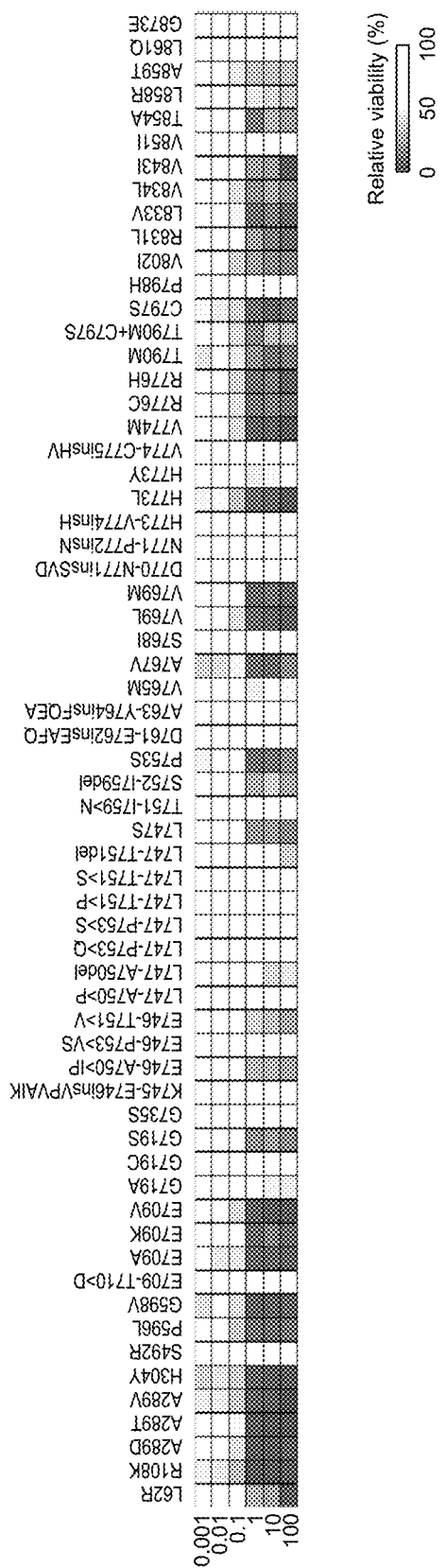
Figures 2, 8:
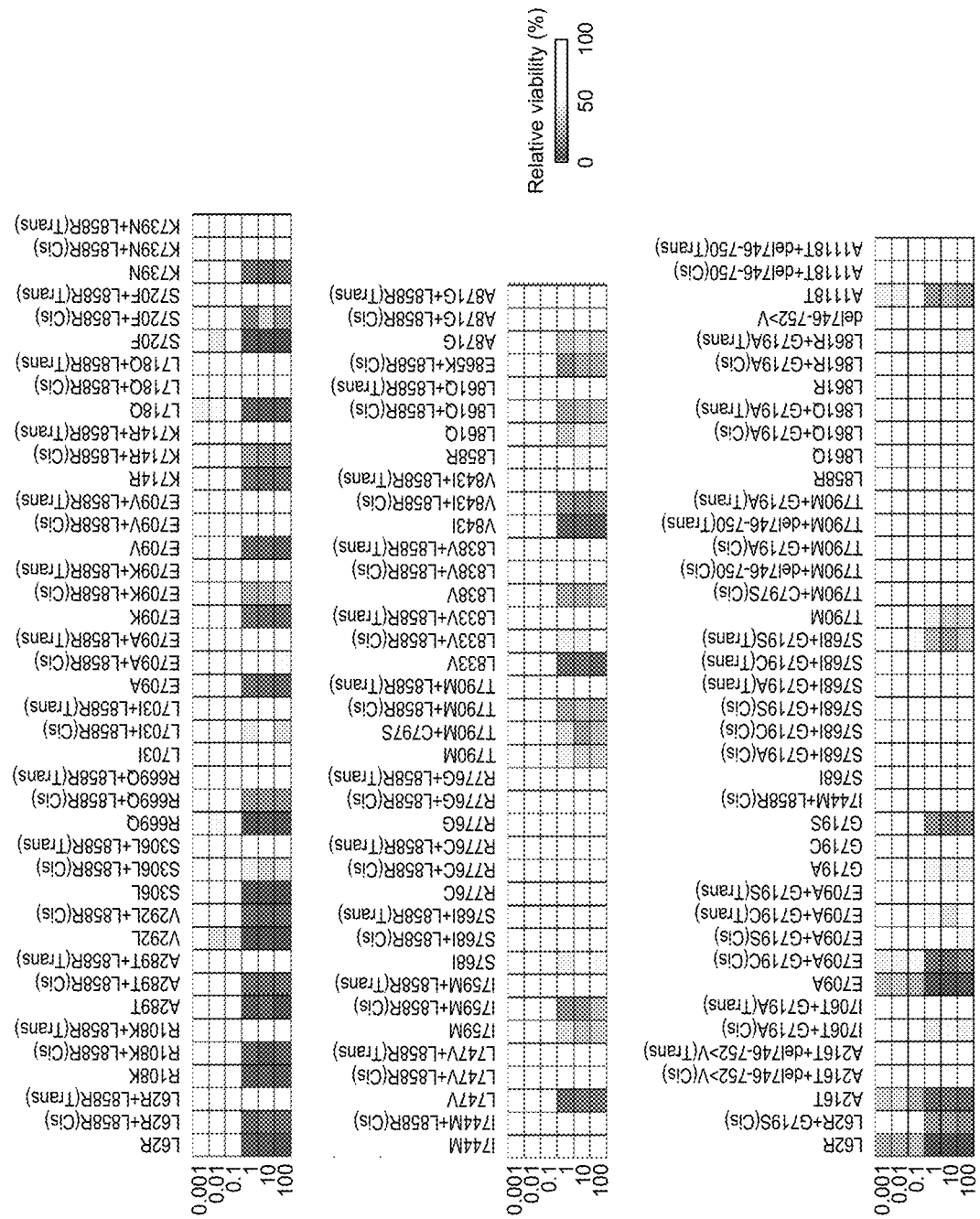

Further, in FIG. 8, it is possible to use, mutations not colored at 0.1 μg/mL, 1 μg/mL, 10 μg/mL, or 100 μg/mL, preferably 1 μg/mL as sensitive markers and, in turn, mutations colored thereat as resistant marker for cetuximab.

As used herein, the sensitive marker can be further divided into the "strictly sensitive marker", on which the probability of the drug to exert its effect is high, and the "partially sensitive marker", on which the probability of the drug to exert its effect is poorer than that on the former. Whether a marker is strictly sensitive, partially sensitive, or resistant to each drug can be defined based on, for instance, IC90 (i.e., 90% inhibitory concentration for cells) as follows. For instance, regarding gefitinib, erlotinib, and osimertinib, mutations causing IC90<0.1 μM can be defined as strictly sensitive markers; mutations causing 0.1 μM≤IC90≤0.5 μM can be defined as partially sensitive markers; and mutations causing IC90>0.5 μM can be defined as resistant markers. Regarding afatinib, mutations causing IC90<0.005 μM can be defined as strictly sensitive markers; mutations causing 0.005 μM≤IC90≤0.01 μM can be defined as partially sensitive markers; and mutations causing IC90>0.01 μM can be defined as resistant markers. Regarding rociletinib, the case of IC90<0.1 μM can be defined as strictly sensitive markers; the case of 0.1 μM≤IC90≤1 μM can be defined as partially sensitive markers; and the case of IC90>1 μM can be defined as resistant markers. Markers that are strictly sensitive, partially sensitive, or resistant to gefitinib, erlotinib, afatinib, osimertinib, and/or rociletinib as determined in accordance with the above definitions are shown below.

A gefitinib strictly sensitive marker includes an EGFR protein having a mutation selected from the group consisting of R108K and L858R (cis), A216T, A216T and E746-S752>V (cis), A216T and E746-S752>V (trans), A289T and L858R (cis), V292L and L858R (cis), V292L and L858R (trans), S306L, S306L and L858R (cis), S306L and L858R (trans), L703I and L858R (cis), L703I and L858R (trans), E709A and G719C (trans), E709G and L858R (trans), E709V and L858R (cis), K714R and L858R (cis), K714R and L858R (trans), L718Q and L858R (trans), G719C, S720F, S720F and L858R (cis), S720F and L858R (trans), T751-1759>N, S752-1759del, S768I and G719C (cis), R776C and L858R (cis), R776C and L858R (trans), R776G and L858R (cis), R776G and L858R (trans), R831L, V834M, H835L, L838V and L858R (cis), V843I and L858R (cis), V843I and L858R (trans), L861Q and L858R (cis), A871G, A871G and L858R (cis), A871G and L858R (trans), A1118T, and A1118T and E746-A750del (cis), or a polynucleotide encoding the protein. A gefitinib partially sensitive marker includes an EGFR protein having a mutation selected from the group consisting of L62R, R108K, R108K and L858R (trans), R222C, R252C, A289D, A289T, A289T and L858R (trans), A289V, V292L, H304Y, S492R, P596L, G598V, L703I, L703P, I706T and G719A (trans), E709A and L858R (cis), E709A and L858R (trans), E709K, E709K and L858R (cis), E709K and L858R (trans), E709V, E709V and L858R (trans), K714R, G719A, G719S, G735P, P741L, I744M, I744M and L858R (cis), K745-E746insVPVAIK, L747S, T751I, P753S, D761-E762insEAFQ, A763-Y764insFQEA, V765M, A767V, S768I and G719A (trans), S768I and G719C (trans), S768I and G719S (cis), S768I and L858R (cis), S768I and L858R (trans), V769M, H773Y, R776C, R776G, R776H, G779S, V786M, C797S, P798H, V802I, R831H, L833F, L833V, L833V and L858R (cis), L833V and L858R (trans), V834L, L838V, L838V and L858R (trans), V843I, P848L, A859T, K860I, L861Q, L861Q and G719A (trans), L861Q and L858R (trans), L861R, L861R and G719A (trans), E865K, G874S, and S1153I, or a polynucleotide encoding the protein.

A gefitinib resistant marker includes an EGFR protein having a mutation selected from the group consisting of L62R and G719S (trans), I706T and G719A (cis), E709-T710>D, E709A, E709A and G719C (cis), E709A and G719S (cis), E709A and G719S (trans), E709G, L718Q, L718Q and L858R (cis), S768I, S768I and G719A (cis), S768I and G719S (trans), V769L, H773L, V774M, T790M and G719A (cis), T790M and G719A (trans), V851I, T854A, L861Q and G719A (cis), L861R and G719A (cis), A864T, A871T, G873E, and A1118T and E746-A750del (trans), or a polynucleotide encoding the protein.

An erlotinib strictly sensitive marker includes an EGFR protein having a mutation selected from the group consisting of R108K and L858R (cis), R108K and L858R (trans), A216T, A216T and E746-S752>V (cis), A216T and E746-S752>V (trans), A289T and L858R (cis), A289T and L858R (trans), V292L and L858R (cis), V292L and L858R (trans), S306L, S306L and L858R (cis), S306L and L858R (trans), L703I and L858R (cis), L703I and L858R (trans), E709A and G719C (cis), E709A and G719C (trans), E709G and L858R (trans), E709K and L858R (cis), E709K and L858R (trans), E709V and L858R (cis), E709V and L858R (trans), K714R and L858R (cis), K714R and L858R (trans), L718Q and L858R (trans), G719C, G719S, S720F, S720F and L858R (cis), S720F and L858R (trans), T751-1759>N, S752-1759del, S768I and G719C (cis), S768I and L858R (cis), R776C and L858R (cis), R776C and L858R (trans), R776G and L858R (cis), R776G and L858R (trans), L833V and L858R (cis), L838V and L858R (cis), V843I and L858R (cis), V843I and L858R (trans), L861Q and L858R (cis), A871G and L858R (cis), A871G and L858R (trans), A1118T, and A1118T and E746-A750del (cis), or a polynucleotide encoding the protein. An erlotinib partially sensitive marker includes an EGFR protein having a mutation selected from the group consisting of L62R, R108K, R222C, R252C, A289D, A289T, A289V, V292L, H304Y, S492R, P596L, G598V, L703I, L703P, I706T and G719A (trans), E709A and L858R (cis), E709A and L858R (trans), E709K, E709V, K714R, G719A, G735S, P741L, I744M, I744M and L858R (cis), K745-E746insVPVAIK, L747S, T751I, P753S, D761-E762insEAFQ, A763-Y764insFQEA, V765M, A767V, S768I, S768I and G719A (trans), S768I and G719C (trans), S768I and L858R (trans), V769M, H773Y, R776C, R776G, R776H, V786M, C797S, P798H, V802I, R831H, R831L, L833F, L833V, L833V and L858R (trans), V834L, V834M, H835L, L838V, L838V and L858R (trans), V843I, P848L, A859T, K860I, L861Q, L861Q and G719A (trans), L861Q and L858R (trans), L861R, L861R and G719A (trans), A864T, E865K, A871G, A871T, G874S, and S1153I, or a polynucleotide encoding the protein.

An erlotinib resistant marker includes an EGFR protein having a mutation selected from the group consisting of L62R and G719S (trans), I706T and G719A (cis), E709-T710>D, E709A, E709A and G719S (cis), E709A and G719S (trans), E709G, L718Q, L718Q and L858R (cis), S768I and G719A (cis), S768I and G719S (cis), S768I and G719S (trans), V769L, N771-P772insN, N771-P772insN, H773L, V774M, T790M and G719A (cis), T790M and G719A (trans), V851I, T854A, L861Q and G719A (cis), L861R and G719A (cis), G873E, and A1118T and E746-A750del (trans), or a polynucleotide encoding the protein.

An afatinib strictly sensitive marker includes an EGFR protein having a mutation selected from the group consisting of L62R, R108K, R108K and L858R (cis), R108K and L858R (trans), A216T, A216T and E746-S752>V (cis), A216T and E746-S752>V (trans), R222C, R252C, A289D, A289T, A289T and L858R (cis), A289T and L858R (trans), A289V, V292L, V292L and L858R (cis), V292L and L858R (trans), H304Y, S306L, S306L and L858R (cis), S306L and L858R (trans), S492R, P596L, G598V, L703I, L703I and L858R (cis), L703I and L858R (trans), L703P, I706T and G719A (trans), E709-T710>D, E709A, E709A and G719C (trans), E709A and L858R (cis), E709A and L858R (trans), E709G, E709G and L858R (trans), E709K, E709K and L858R (cis), E709K and L858R (trans), E709V, E709V and L858R (cis), E709V and L858R (trans), K714R, K714R and L858R (cis), K714R and L858R (trans), L718Q and L858R (trans), G719A, G719C, G719S, S720F, S720F and L858R (cis), S720F and L858R (trans), G735S, P741L, I744M, I744M and L858R (cis), L747-P753>Q, L747S, T751-1759>N, S752-1759del, P753S, D761-E762insEAFQ, A763-Y764insFQEA, V765M, A767V, S768I and G719A (trans), S768I and G719C (trans), S768I and G719S (cis), S768I and L858R (cis), S768I and L858R (trans), V769M, H773Y, R776C, R776C and L858R (cis), R776C and L858R (trans), R776G, R776G and L858R (cis), R776G and L858R (trans), R776H, V786M, P798H, V802I, R831H, R831L, L833F, L833V, L833V and L858R (cis), L833V and L858R (trans), V834L, V834M, H835L, L838V, L838V and L858R (cis), L838V and L858R (trans), V843I, V843I and L858R (trans), P848L, K860I, L861Q, L861Q and G719A (trans), L861Q and L858R (cis), L861Q and L858R (trans), L861R, A864T, E865K, A871G, A871G and L858R (cis), A871G and L858R (trans), A871T, G874S, A1118T, A1118T and E746-A750del (cis), and S1153I, or a polynucleotide encoding the protein. An afatinib partially sensitive marker includes an EGFR protein having a mutation selected from the group consisting of T751I, S768I, V769L, H773L, V774M, V779S, T854A, A859T, and G873E, or a polynucleotide encoding the protein.

An afatinib resistant marker includes an EGFR protein having a mutation selected from the group consisting of L62R and G719S (trans), I706T and G719A (cis), E709A and G719C (cis), E709A and G719S (cis), E709A and G719S (trans), L718Q, L718Q and L858R (cis), S768I and G719A (cis), S768I and G719C (cis), S768I and G719S (trans), V769-D770insASV, D770-N771insSVD, N771-P772insN, H773-V774insH, H773-V774insPH, V774-C775insHV, T790M and G719A (cis), T790M and G719A (trans), C797S, V851I, L861Q and G719A (cis), L861R and G719A (cis), L861R and G719A (trans), and A1118T and E746-A750del (trans), or a polynucleotide encoding the protein.

An osimertinib strictly sensitive marker includes an EGFR protein having a mutation selected from the group consisting of L62R, R108K, R108K and L858R (cis), R108K and L858R (trans), A216T, A216T and E746-S752>V (cis), A216T and E746-S752>V (trans), R222C, R252C, A289D, A289T, A289T and L858R (cis), A289T and L858R (trans), A289V, V292L, V292L and L858R (cis), V292L and L858R (trans), H304Y, S306L and L858R (cis), S306L and L858R (trans), S492R, P596L, G598V, L703I and L858R (cis), L703I and L858R (trans), L703P, E709A and G719C (trans), E709A and G719S (trans), E709A and L858R (trans), E709G and L858R (trans), E709K and L858R (cis), E709K and L858R (trans), E709V and L858R (cis), E709V and L858R (trans), K714R and L858R (cis), K714R and L858R (trans), G719C, G719S, S720F, S720F and L858R (cis), S720F and L858R (trans), G735S, P741L, I744M and L858R (cis), K745-E746insVPVAIK, E746-A750>IP, E746-P753>VS, E746-T751>V, L747-A750>P, L747-A750del, L747-P753>Q, L747-P753>S, L747-T751>P, L747-T751>S, L747-T751del, L747S, T751-1759>N, T751I, S752-1759del, P753S, D761-

E762insEAFQ, A763-Y764insFQEA, V765M, A767V, S768I and L858R (cis), V769-D770insASV, V769L, V769M, N771-P772insN, H773-V774insH, H773-V774insPH, H773L, H773Y, V774-C775insHV, V774M, R776C, R776C and L858R (cis), R776C and L858R (trans), R776G, R776G and L858R (cis), R776G and L858R (trans), R776H, G779S, V786M, T790M, T790M and G719A (trans), T790M and L858R (trans), P798H, V802I, R831H, R831L, L833F, L833V, L833V and L858R (cis), L833V and L858R (trans), V834L, V834M, H835L, L838V and L858R (cis), L838V and L858R (trans), V843I, V843I and L858R (cis), V843I and L858R (trans), P848L, V851I, T854A, L858R, A859T, K860I, L861Q, L861Q and L858R (cis), L861Q and L858R (trans), A864T, A871G, A871G and L858R (cis), A871G and L858R (trans), G873E, G874S, E746-S752>V, A1118T, A1118T and E746-A750del (cis), and S1153I, or a polynucleotide encoding the protein. An osimertinib partially sensitive marker includes an EGFR protein having a mutation selected from the group consisting of L62R and G719S (trans), I706T and G719A (cis), I706T and G719A (trans), E709-T710>D, E709A, E709A and G719C (cis), E709G, E709K, E709V, K714R, G719A, I744M, S768I, S768I and G719A (trans), S768I and G719C (cis), S768I and G719C (trans), S768I and G719S (cis), S768I and G719S (trans), S768I and L858R (trans), D770-N771insSVD, T790M and E746-A750del (trans), L838V, L861Q and G719A (trans), L861R, L861R and G719A (cis), and L861R and G719A (trans), or a polynucleotide encoding the protein.

An osimertinib resistant marker includes an EGFR protein having a mutation selected from the group consisting of S306L, L7031, E709A and G719S (cis), E709A and L858R (cis), L718Q, L718Q and L858R (cis), L718Q and L858R (trans), S768I and G719A (cis), T790M and E746-A750del (cis), T790M and G719A (cis), C797S, L861Q and G719A (cis), E865K, A871T, and A1118T and E746-A750del (trans), or a polynucleotide encoding the protein.

A rociletinib strictly sensitive marker includes an EGFR protein having a mutation selected from the group consisting of E746-A750>IP, E746-P753>VS, E746-T751>V, L747-A750>P, L747-A750del, L747-P753>Q, L747-P753>S, L747-T751>P, L747-T751>S, L747-T751del, T751-1759>N, S752-1759del, H835L, L858R, A871T, A1118T, or a polynucleotide encoding the protein. A rociletinib partially sensitive marker includes an EGFR protein having a mutation selected from the group consisting of R108K, R222C, R252C, A289D, A289T, H304Y, P596L, L62R, G719A, G719C, G719S, G735S, K745-E746insVPVAIK, L747S, T751I, D761-E762insEAFQ, V765M, H773L, V774-C775insHV, V774M, V786M, T790M, P798H, R831H, L833F, V851I, K860I, L861Q, G873E, G874S, and S1153I, or a polynucleotide encoding the protein.

A rociletinib resistant marker includes an EGFR protein having a mutation selected from the group consisting of A289V, S492R, G598V, L703P, E709-T710>D, E709A, E709G, E709K, E709V, S720F, P741L, P753S, A763-Y764insFQEA, A767V, S768I, V769-D770insASV, V769L, V769M, D770-N771insSVD, N771-P772insN, H773-V774insH, H773-V774insPH, H773Y, R776C, R776H, G779S, C797S, V802I, R831L, L833V, V834L, V834M, V843I, P848L, T854A, A859T, A864T, E865K, and A871G, or a polynucleotide encoding the protein.

Regarding cetuximab, for instance, mutations causing IC90<1 μg/mL can be defined as strictly sensitive markers; mutations causing 1 μg/mL IC90≤100 μg/mL can be defined as partially sensitive markers; and mutations causing IC90>100 μg/mL can be defined as resistant markers. Markers that are strictly sensitive, partially sensitive, or resistant to cetuximab as determined in accordance with the above definitions are shown below.

A cetuximab strictly sensitive marker includes an EGFR protein having a mutation selected from the group consisting of L62R, L62R and L858R (cis), R108K, R108K and L858R (cis), A216T, A289D, A289T, A289T and L858R (cis), A289V, V292L, V292L and L858R (cis), H304Y, S306L, P596L, G598V, R669Q, E709A, E709A and G719C (trans), E709K, E709V, K714R, L718Q, S720F, L747V, P753S, A767V, V769L, V769M, H773L, V774M, R776H, C797S, L833V, and V843I, or a polynucleotide encoding the protein.

A cetuximab partially sensitive marker includes an EGFR protein having a mutation selected from the group consisting of R776C and R831L, or a polynucleotide encoding the protein.

A cetuximab resistant marker includes an EGFR protein having a mutation selected from the group consisting of L62R and G719S (trans), L62R and L858R (trans), R108K and L858R (trans), A216T and E746-S752>V (cis), A216T and E746-S752>V (trans), A289T and L858R (trans), S306L and L858R (cis), S306L and L858R (trans), S492R, R669Q and L858R (cis), R669Q and L858R (trans), L7031, L7031 and L858R (cis), L7031 and L858R (trans), I706T and G719A (cis), I706T and G719A (trans), E709-T710>D, E709A and G719C (cis), E709A and G719S (cis), E709A and G719S (trans), E709A and L858R (cis), E709A and L858R (trans), E709K and L858R (cis), E709K and L858R (trans), E709V and L858R (cis), E709V and L858R (trans), K714R and L858R (cis), K714R and L858R (trans), L718Q and L858R (cis), L718Q and L858R (trans), G719A, G719C, G719S, S720F and L858R (cis), S720F and L858R (trans), G735S, K739N, K739N and L858R (cis), K739N and L858R (trans), I744M, I744M and L858R (cis), K745-E746insVPVAIK, E746-S752>V, E746-A750>IP, E746-P753>VS, E746-T751>V, L747-A750>P, L747-A750del, L747-P753>Q, L747-P753>S, L747-T751>P, L747-T751>S, L747-T751del, L747S, L747V and L858R (cis), L747V and L858R (trans), T751-1759>N, S752-1759del, I759M, I759M and L858R (cis), I759M and L858R (trans), D761-E762insEAFQ, A763-Y764insFQEA, V765M, S768I, S768I and G719A (cis), S768I and G719A (trans), S768I and G719C (cis), S768I and G719C (trans), S768I and G719S (cis), S768I and G719S (trans), S768I and L858R (cis), S768I and L858R (trans), D770-N771insSVD, N771-P772insN, H773-V774insH, H773Y, V774-C775insHV, R776C and L858R (cis), R776C and L858R (trans), R776G, R776G and L858R (cis), R776G and L858R (trans), T790M, T790M and C797S (cis), T790M and E746-A750del (cis), T790M and E746-A750del (trans), T790M and G719A (cis), T790M and G719A (trans), T790M and L858R (cis), T790M and L858R (trans), P798H, V802I, L833V and L858R (cis), L833V and L858R (trans), V834L, L838V, L838V and L858R (cis), L838V and L858R (trans), V843I and L858R (cis), V843I and L858R (trans), V851I, T854A, L858R, A859T, L861Q, L861Q and G719A (cis), L861Q and G719A (trans), L861Q and L858R (cis), L861Q and L858R (trans), L861R, L861R and G719A (cis), L861R and G719A (trans), E865K and L858R (cis), A871G, A871G and L858R (cis), A871G and L858R (trans), G873E, A1118T, A1118T and E746-A750del (cis), and A1118T and E746-A750del (trans), or a polynucleotide encoding the protein.

In one aspect, the present invention relates to a marker that is resistant to each EGFR tyrosine kinase inhibitor, consisting of an EGFR protein having A839T mutation or a polynucleotide encoding the protein. Examples of the EGFR tyrosine kinase include gefitinib, erlotinib, afatinib, and osimertinib.

<Means or Kit for Detecting Marker>

In one aspect, the present invention relates to means, such as a primer set, a probe, an aptamer, or an antibody, or a kit comprising any thereof, for detecting the above marker(s) for detecting cancer, marker(s) for detecting a mutation that suppresses differentiation, drug sensitive marker(s), or drug resistant marke(s). These means can be easily designed depending on the above markers by those skilled in the art.

The primer set is not particularly limited as long as it can be used to specifically detect a protein or gene mutation site of each specific marker. For instance, when the above maker is a mutation of the EGFR protein, examples of a forward primer and a reverse primer include:

(1) a forward primer comprising nucleotides comprising consecutive 14 to 30 nucleotides such as 16 to 28 nucleotides and preferably 18 to 26 nucleotides of SEQ ID NO: 2 and a reverse primer comprising nucleotides comprising consecutive 14 to 30 nucleotides such as 16 to 28 nucleotides and preferably 18 to 26 nucleotides of a sequence complementary to the sequence set forth in SEQ ID NO: 2; and (2) a forward primer comprising nucleotides comprising 14 to 30 nucleotides such as 16 to 28 nucleotides and preferably 18 to 26 nucleotides of a sequence which hybridizes with nucleic acid consisting of a complementary sequence of SEQ ID NO: 2 under a stringent condition and a reverse primer comprising nucleotides comprising 14 to 30 nucleotides such as 16 to 28 nucleotides and preferably 18 to 26 nucleotides of a sequence which hybridizes with nucleic acid consisting of a sequence of SEQ ID NO: 2 under a stringent condition.

When a marker is a COL1A2/DCAF6 fusion protein, a primer set may be prepared in the same way based on the nucleotide sequence set forth in SEQ ID NO: 4, 6, or 8.

As used herein, the "stringent condition" means a condition in which what is called a specific hybrid is formed and a non-specific hybrid is not formed. The stringent condition may employ a condition of known hybridization protocols. For instance, the condition can be suitably determined, referring to Green and Sambrook, Molecular Cloning, 4th Ed (2012), Cold Spring Harbor Laboratory Press. Specifically, the stringent condition can be set by a temperature and a salt concentration in a solution during a hybridization protocol and a temperature and a salt concentration in a solution at a washing step during a hybridization protocol. Examples of a more detailed stringent condition include a sodium concentration of from 25 to 500 mM and preferably from 25 to 300 mM and a temperature of from 42 to 68° C. and preferably from 42 to 65° C. More specific examples include 5×SSC (83 mM NaCl and 83 mM sodium citrate) and a temperature of 42° C.

The probe for detecting a polynucleotide encoding each marker is not particularly limited as long as it can be used to detect a protein or gene mutation site of a marker.

For instance, when the maker is a mutation of the EGFR protein, the probe preferably comprises:

(1) a polynucleotide which hybridizes with a polynucleotide comprising a sequence of at least consecutive 14, for example 20, and preferably 30 nucleotides of the sequence set forth in SEQ ID NO: 2 under a stringent condition; or (2) a polynucleotide which hybridizes with a polynucleotide comprising a sequence complementary to a sequence of at least consecutive 14, for example 20, and preferably 30 nucleotides of SEQ ID NO: 2, under a stringent condition.

When a marker is a COL1A2/DCAF6 fusion protein, a probe may be likewise prepared based on the nucleotide sequence set forth in SEQ ID NO: 4, 6, or 8. In this case, in particular, it is preferable to make a probe that can detect a portion at which a COL1A2 protein and a DCAF6 protein is fused.

The primer and the probe can be prepared by using a known process known to those skilled in the art and are not limited. For instance, a chemical synthesis process may be used for the preparation.

An aptamer for the above maker may be prepared by the SELEX (systematic evolution of ligands by exponential enrichment) protocol, etc. The SELEX protocol is a method of selecting nucleic acid bound more strongly to a target molecule, comprising repeating several to several dozen rounds of a series of cycle including: selecting a nucleic acid molecule bound to a target molecule from pooled nucleic acid molecules having a random sequence region and a primer-binding region at both ends thereof; collecting and then amplifying the nucleic acid molecules bound; and using the resulting molecules as pooled nucleic acid at the next round (see, for example, Tuerk C, Gold L (1990) Science 249 (4968): 505-510).

An antibody that specifically binds to the marker may be any one of a polyclonal antibody, a monoclonal antibody, a recombinant antibody, and a synthetic antibody. The "polyclonal antibody" refers to a population of multiple kinds of immunoglobulins that can recognize different epitopes of the same antigen. The polyclonal antibody can be obtained from serum of an animal which has been immunized with a target molecule as an antigen. The "monoclonal antibody" refers to a population of single immunoglobulin clone. The monoclonal antibody can be prepared by using a hybridoma prepared by isolating an antibody-producing B cell from an immunized anima, and fusing the B cell with a myeloma cancer cell. The "recombinant antibody" herein means an antibody created by combining amino acid sequences of antibodies of different animal origins (e.g., a chimeric antibody and a humanized antibody). In addition, the "synthetic antibody" herein means an antibody synthesized by a chemical process or a recombinant DNA technique. Examples include single chain Fvs (scFv: single chain Fragment of variable region), diabodies, triabodies, and tetrabodies.

The kit of the present invention may include for example, a buffer, an enzyme, and an instruction, in addition to the above primer set, probe, aptamer, or antibody.

<Method for Assisting in Determining Whether or Not Subject Has Mutation That Suppresses Differentiation or Suffers from Cancer or Has Possibility of Suffering from Cancer>

In one aspect, the present invention relates to a method for assisting in determining whether or not a subject suffers from cancer or has a possibility of suffering from cancer. Examples of the kind of cancer from which a subject is determined to suffer according to the aspect include, but are not limited to, brain tumor, pharyngeal cancer, thyroid cancer, lung cancer, breast cancer, esophageal cancer, gastric cancer, liver cancer, pancreatic cancer, renal cancer, small intestine cancer, large intestine cancer, bladder cancer, prostate cancer, cervical cancer, ovarian cancer, lymphoma, and melanoma, and Preferably, lung cancer.

This method comprises a step of detecting a marker for detecting cancer or a marker for detecting a mutation that suppresses differentiation as described herein in a sample obtained from a subject among subjects (detection step). The detection method in the detection step is not limited and the detection may use means such as a primer set, a probe, an aptamer, or an antibody, or a kit comprising any thereof, for detecting the above marker. Alternatively, the detection may be conducted by sequence analysis using a next-generation sequencer.

In addition, this method comprises, as an optional step, a step of determining that a subject suffers from cancer or has a high possibility of suffering from cancer when a marker for detecting cancer as described herein is detected (determination step), in addition to the detection step.

The biological species of a subject herein is not limited and is preferably a mammal, for example, the mammal such as primates (e.g., a human, chimpanzee), experimental animals (e.g., a rat, mouse), domestic animals (e.g., a pig, cow, horse, sheep, goat), and pets (e.g., a dog, cat), and preferably, a human.

As used herein, the "sample" means a biological sample that is subjected to a method of the present invention. Examples of the sample that can be used in the present invention include, but are not limited to, cells and tissues isolated from a living body. The tissues involve cancer lesions and examples include the brain, pharynx, thyroid, lung, breast, esophagus, stomach, liver, pancreas, kidney, small intestine, large intestine, bladder, prostate, uterus, and ovary, and preferably, lung. For instance, a biopsy sample of these tissues may be used.

In one aspect, the present invention relates to a method for assisting in determining the presence or absence of a mutation that suppresses differentiation. This method comprises a step of detecting a marker for detecting a mutation that suppresses differentiation as described herein in a sample obtained from a subject (detection step). The detection method in the detection step is not limited and the detection may use means for detecting a marker that suppresses differentiation, such as a primer set, a probe, an aptamer, or an antibody, or a kit comprising any thereof. Alternatively, the detection may be conducted by sequence analysis using a next-generation sequencer. In addition, this method comprises, as an optional step, a step (determination step) of determining that a subject has a mutation that suppresses the differentiation when a marker for detecting a mutation that suppresses differentiation as described herein is detected, in addition to the detection step.

<Method for Evaluating Drug Sensitivity>

In one aspect, the present invention relates to a method for assisting in determining whether a subject is sensitive (or resistant) to a drug such as an anti-cancer drug. This method comprises a step of detecting a drug sensitive or resistant marker as described herein in a sample obtained from a subject (detection step). The detection method in the detection step is not limited and the detection may use means for detecting the above drug sensitive or resistant marker, such as a primer set, a probe, an aptamer, or an antibody, or a kit comprising any thereof. Alternatively, the detection may be conducted by sequence analysis using a next-generation sequencer.

In addition, this method comprises, as an optional step, a step (determination step) of determining that a subject is sensitive to the drug when a drug sensitive marker as described herein is detected and/or a subject is resistant to the drug when a drug resistant marker as describe herein is detected, in addition to the detection step.

This method may be used to evaluate whether a subject is sensitive or resistant to a drug and it is possible to select a suitable drug based on the evaluation.

<Cell Population>

In one aspect, the present invention relates to a cell population. A cell population of the present invention contains at least 2, for instance, 3 or more, 4 or more, 5 or more, 7 or more, 10 or more, 20 or more, 50 or more and 500 or less, 200 or less, or 100 or different cells comprising different polynucleotides constituting makers for detecting cancer, markers for detecting a mutation that suppresses differentiation, or drug sensitive or resistant makers as described herein.

Especially, these polynucleotides are preferably linked to each unique tag sequence. In this case, such a cell population may be used in the evaluation method of the present invention. When the cell population of the present invention is used in the evaluation method of the present invention, the integration step and the mixing step may be omitted.

EXAMPLES

Example 1: Evaluation of Sensitivity and Accuracy of MANO (Mixed All Nominated Mutants in One) Method Materials and Methods
1. Cell Lines HEK (Human Embryonic kidney) 293 cells and mouse 3T3 fibroblasts were obtained from the American Type Culture Collection and maintained in Dulbecco's modified Eagle medium-F-12 (DMEM-F12) supplemented with 10% FBS (both from Thermo Fisher Scientific, Waltham, Mass.). Ba/F3 cells were cultured in RPMI 1640 medium (Thermo Fisher Scientific) supplemented with 10% FBS and mouse IL-3 (20 U/mL; Sigma, St. Louis, Mo.).

2. Construction of Retroviral Vector with Random Bar Code Sequence.

First, 60-bp nucleotides (SEQ ID NO: 9) were inserted into the BamHI restriction enzyme site of pcx4-bleo vector (https://www.addgene.org/vector-database/2309/). Next, each primer containing each 6-bp random sequence was used to perform site-directed mutagenesis to produce each pcx5-bleo with each bar code sequence. Then, cDNA of wild-type human EGFR was isolated from a frozen sample of a subject having the wild-type EGFR and was ligated into pcx5-bleo. The cDNAs encoding the EGFR mutants were generated using the QuickChange II Site-Directed Mutagenesis kit (Agilent Technologies, Santa Clara, Calif.) and ligated into pcx5-bleo. In addition, cDNAs for EML4-ALK (Manabu Soda et al., nature, 2007, 448, pp. 561-566), KIFSB-RET (Takashi Kohnol et al., nature medicine, 2012, 18(3), pp. 375-377), KRAS (G12V), CD74-ROS1 (Kengo Takeuchi et al., nature medicine, 2012, 18(3), pp. 378-381), EGFR (E746-A750del), EGFR (L858R), BRAF (V600E), MET exon 14 skipping 22 and 23, and ERBB2(V777L) were isolated from frozen samples of lung cancer patients positive for the respective mutations and cloned into the pcx5-bleo vector.

3. Preparation of Retrovirus and Transduction of Cell Lines

The recombinant plasmids prepared as described above were introduced together with packaging plasmids (Takara Bio, Shiga, Japan) into HEK293 cells to obtain recombinant retroviral particles. For the focus-formation assay, 3T3 cells were infected with ecotropic recombinant retroviruses using 4 µg/mL polybrene (Sigma-Aldrich, St. Louis, Mo., USA) for 24 hours and further cultured in DMEM-F12 supplemented with 5% calf serum for up to 2 weeks. Cell transformation was assessed through either phase-contrast microscopy or staining with Giemsa solution.

4. Detection by MANO Method

Genomic DNA from the cell lysates was PCR-amplified, using the primers 5'-TGGAAAGGACCTTACACAGT-CCTG-3' (SEQ ID NO: 10) and 5'-GACTCGTT-GAAGGGTAGACTAGTC-3' (SEQ ID NO: 11), to give a region containing a bar code sequence. The PCR conditions were as follows:

initial denaturation: 3 min at 95° C.;
denaturation: 15 sec at 95° C.;
annealing: 30 sec at 60° C.;
extension: 60 sec at 72° C.;
the number of cycles: 30; and
final extension: 10 min at 72° C.

The amplified PCR products were purified using AMPure beads (Beckman Coulter, Brea, Calif.). The sequencing libraries were generated using the NEB Next Ultra DNA Library Prep Kit (NEB, Ipswich, Mass.) according to the manufacturer's instructions. The library quality was assessed using a Qubit 2.0 fluorometer (Thermo Fisher Scientific) and the Agilent 2200 Tape Station system. The library was sequenced on an Illumina MiSeq (at 300 cycles) using Reagent Kit V2 to give 150-bp paired-end reads. These sequence reads included the following bar code-containing sequences: 5'-CTAGACTGCCGGATCACTCT-3' (SEQ ID NO: 12) (where N denotes any nucleotide) and their complementary sequences. The amount of each mutant was estimated by determining the read counts for these bar code sequences. DMSO-treated cell mixtures were used as the reference control for scaling of each cell clone signal. Thus, the signal from each treated cell line was calculated as 100×(median read count)/(median read count of the DMSO control). The median read count was obtained by three independent experiments.

5. In Vitro MANO Method

Two days after the virus infection, the number of cells with transduced genes was counted and the same number of cells was mixed, and a portion of the mixed cells was used for DNA extraction (at day 0). Subsequently, the mixed cells were cultured in the absence of a drug (transforming potential evaluation) and in the presence of a drug at varied concentrations (drug sensitivity evaluation). Then, the cells were collected at examination time points and were subjected to DNA extraction. The drugs used and their manufacturers are shown below:

gefitinib, erlotinib, afatinib, osimertinib, rociletinib, and crizotinib: LC laboratories;
alectinib: Selleck Chemicals;
puromycin: Invitrogen; and
cetuximab: Merck Serono.

6. In Vivo MANO Method

Individually transduced cell clones were mixed in equal numbers, and $2.5\times10^6$ cells of this mixture ($1\times10^5$ cells from each of 25 cell clones) were subcutaneously injected into 6-week-old female nude mice according to the animal use protocol approved by the University of Tokyo Animal Care and Use Committee. The mice were treated once daily for 16 days by gavage with the EGFR TKI erlotinib (50 mg/kg body weight) or vehicle control (1% sodium carboxymethyl cellulose), beginning 5 days after injection of the cell lines.

The tumors were resected, and each tumor was cut into four pieces. Relative abundance of each cell clone was determined by the MANO method. Specifically, for each sample, the numbers of bar codes derived from the cell mixture used for the injection were used to convert the number of bar codes corresponding to each cell line to a relative cell count ($A_X/T_X$). Each relative cell count was used to calculate a relative contribution to tumors containing the respective cell lines.

7. Calculation of Proliferation Potential Score and Drug Sensitivity Score.

The scores for the proliferation potential and drug sensitivity of each gene of interest were calculated by the following calculation equations:

$$\text{Proliferation potential score of gene } A \text{ of interest} = (A_X \times T_0)/(A_0 \times T_X); \text{ and}$$

$$\text{Drug sensitivity score of gene } A \text{ of interest} = (AD_X \times T_X)/(A_X \times TD_X),$$

[wherein $A_X$=the read count of a bar code added to gene A of interest in cells collected at Day X;

$T_0$=the total read count of all bar codes in cells collected at Day 0;

$A_0$=the read count of the bar code added to gene A of interest in the cells collected at Day 0;

$T_X$=the total read count of all bar codes in the cells collected at Day X;

$AD_X$=the read count of the bar codes added to gene A of interest in cells collected at Day X after drug administration; and $TD_X$=the total read count of all bar codes in the cells collected at Day X after drug administration.]

The proliferation potential score of gene A of interest indicates that the higher the score is, the higher the proliferation potential of gene A of interest is. The drug sensitivity score of gene A of interest indicates the viability of a cell having the gene A of interest introduced therein at the indicated concentration.

8. Alamar Blue Cell Viability Assay

After incubating the cells in 96-well plates (with 100 μL of culture medium per well), 10 μL of Alamar Blue (Thermo Fisher Scientific) was added, and the fluorescence was measured (excitation, 530 nm; emission, 590 nm) at the indicated times. Wells without cells were assayed as negative controls. Adjustment for fluorescence gain for every well was performed against the well with the maximum fluorescence intensity.

(Results)

First, to determine sensitivity of the MANO method, cDNAs (EML4-ALK, KIF5B-RET, KRAS(G12V), CD74-ROS1, EGFR(E746-A750del), and EGFR(L858R)) were each introduced with a bar code sequence into Ba/F3 cells. Next, only the number of cells having the EGFR(L858R) cDNA introduced was varied (from 100 to 20000 cells) and the cells were mixed with 20000 cells from each of the rest cells having the other 5 different cDNAs introduced. Then, genomic DNA was isolated from each cell mixture and subjected to PCR and next-generation sequencing. The read count of a bar code sequence corresponding to each Ba/F3 cell having each of 5 different cDNAs other than the EGFR(L858R) cDNA introduced was constant in each mixture. By contrast, the read count of a bar code sequence corresponding to the Ba/F3 cell expressing EGFR(L858R) which was mixed with varied cell numbers was changed proportionally to the number of cells mixed (r=0.99; data not shown). This result demonstrates that the MANO method is very sensitive and can quantitatively detect the number of cells, even in a range of just about 0.1%.

Figure 2:
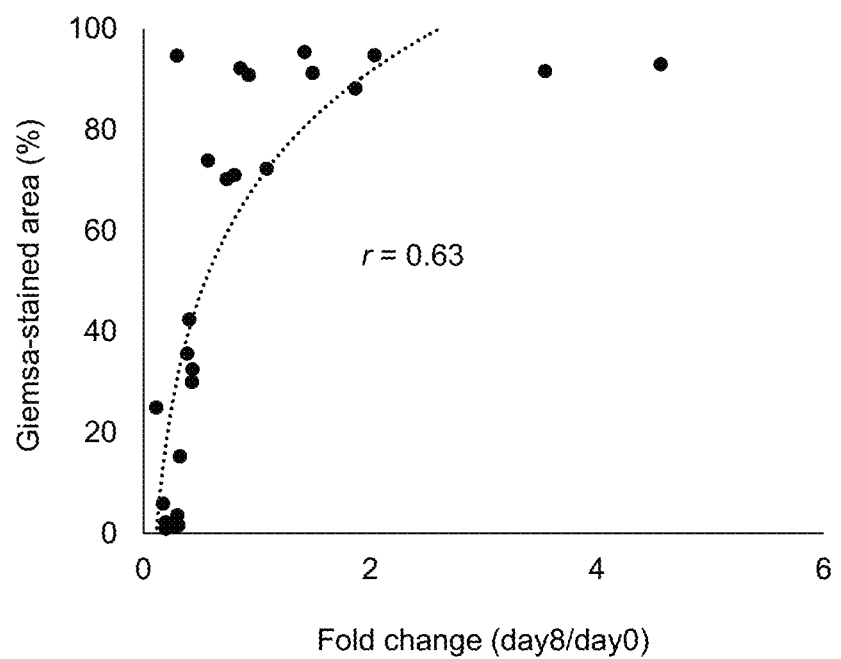
FIG. 2 is a graph showing that the Giemsa-stained area (%) in a focus-formation assay is positively correlated (r=0.63) with the fold change (day 8/day 0) obtained by one embodiment of a method for evaluating multiple different genes of interest of the present invention.

Subsequently, whether the MANO method was able to evaluate transforming potential was examined. First, typical 3T3 focus-formation assay was conducted to measure transforming potential of 14 different EGFR mutations (EGFR (T790M), EGFR (G719C), EGFR (G719S), EGFR (L861Q), EGFR (S768I), EGFR (E709K), EGFR (E709A), EGFR (A289V), EGFR (G598V), EGFR (E865K), EGFR (E865R), EGFR (P794H), EGFR (T790M/C797S), and EGFR(E746-A750del)) and wild-type EGFR. Other oncogenes such as BRAF(V600E), MET exon 14 skipping22 and 23, and ERBB2(V777L) were likewise assayed. Next, each cDNA was subjected to the MANO method using 3T3 cells. When the 3T3 cells were cultured under different medium conditions, the proportion of each gene was substantially the same (data not shown). In addition, the Giemsa-stained area (%) in the focus-formation assay was positively correlated with the fold change (day 8/day 0) (i.e., the proliferation potential score) obtained by the MANO method (r=0.63; FIG. 2). This result demonstrates that the MANO method can evaluate transforming potential like Giemsa staining.

The tumor formation potential was assayed in vivo in nude mice by the MANO method using 3T3 cells. Cells expressing green fluorescence protein (GFP) or wild-type EGFR, or ERBB2 or MET were depleted 11 days after transplantation, whereas cells expressing EGFR(L858R) or EGFR(E746-A750del) gradually proliferated at that time (data not shown). Such results are consistent with the in vitro assay results. These results demonstrate that the MANO method is a method in which in vivo transforming potential can be evaluated.

Figure 3:
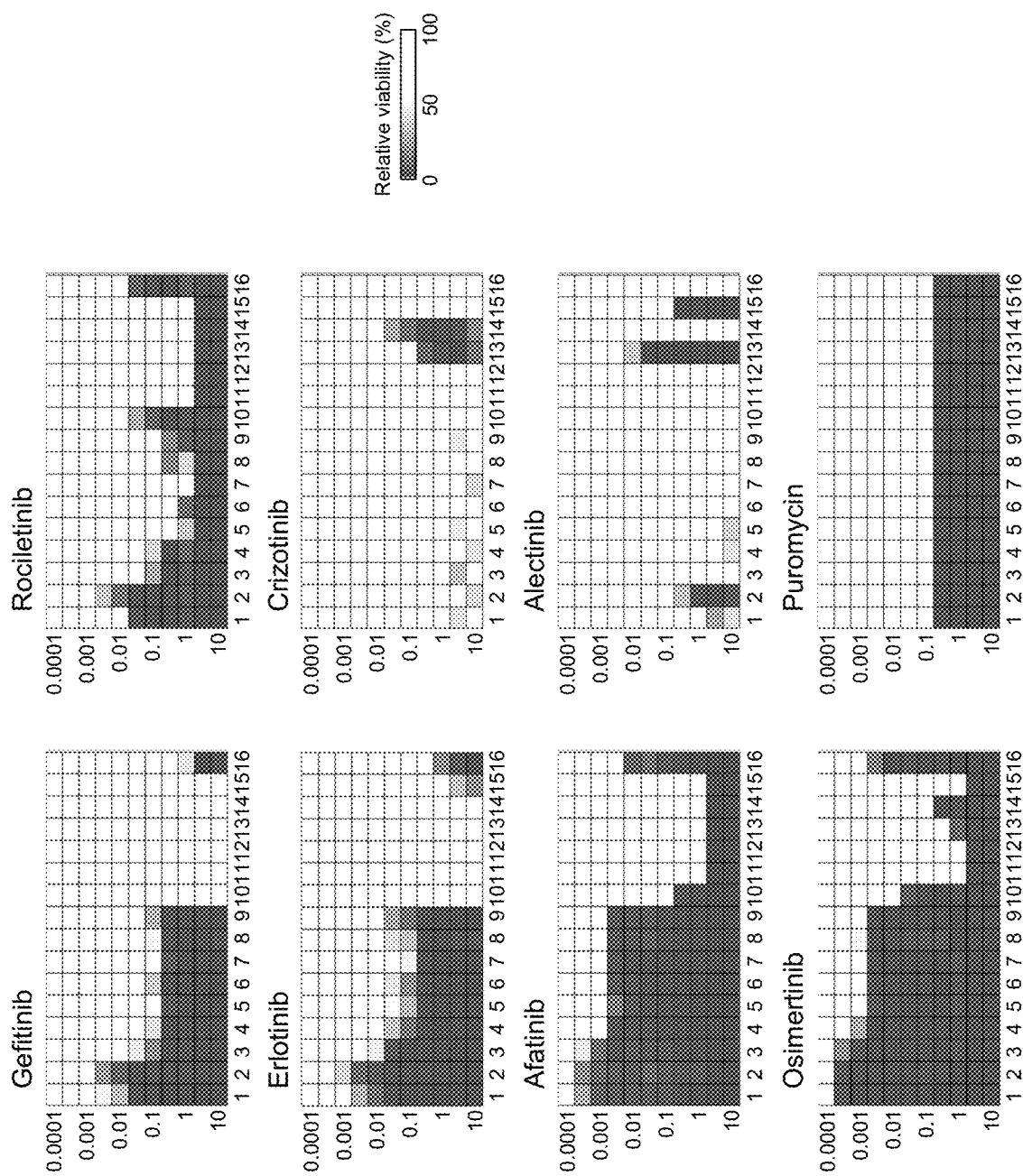
FIG. 3 is diagrams showing the results of testing various tyrosine kinase inhibitors (hereinafter, referred to as TKIs) for pooled 16 Ba/F3 cells, each expressing each of active EGFR mutants (11 kinds) and other oncoproteins (5 kinds). Here, in order to take into account the different doubling time of each transgenic cell, each Ba/F3 cell treated with each TKI was compared to a vehicle-treated control to calculate the growth inhibition of each cell clone. The drugs used include gefitinib, erlotinib, afatinib, osimertinib, rociletinib, crizotinib, alectinib, and puromycin. In the diagrams, the ordinate indicates drug concentrations (including, from the top to bottom, 0.0001 µM, 0.0005 µM, 0.001 µM, 0.005 µM, 0.01 µM, 0.05 µM, 0.1 µM, 0.5 µM, 1 µM, 5 µM, and 10 µM); and the abscissa indicates used cells with each mutation (1:EGFR:L858R, 2:EGFR:746-750del, 3:EGFR:G719S, 4:EGFR:L861Q, 5:EGFR:S768I, 6:EGFR:E709K, 7:EGFR:E709A, 8:EGFR:A289V, 9:EGFR:G598V, 10:EGFR:T790M, 11:EGFR:T790M and C797S, 12:KRAS:G12V, 13:EML4-ALK, 14:CD74-ROS1, 15:KIFB-RET, and 16:ERBB2:V777L). The relative viability is color-coded and as the color becomes deeper, the viability is indicated to be lower.

Next, various tyrosine kinase inhibitors (hereinafter, referred to as TKIs) were tested in pooled 16 different Ba/F3 cells, expressing active EGFR mutants (11 kinds) or other oncoproteins (5 kinds). Here, each Ba/F3 cell treated with each TKI was compared to a vehicle-treated control to calculate the growth inhibition (drug sensitivity score) of each cell clone, in order to take into account the different doubling time of each transgenic cell (FIG. 3). Puromycin, a cytotoxic compound, induced uniform cell death among cell clones, whereas EGFR TKIs (gefitinib, erlotinib, afatinib, osimertinib, and rociletinib) caused dose-dependent cell death of each cell having each of 5 TKI-sensitive EGFR mutants (L858R, E746-A750 del, G719S, E861Q, and S768I) among the pooled cells. The EGFR(T790M)-expressing Ba/F3 cell was resistant to the first and second generation EGFR TKIs (gefitinib, erlotinib, and afatinib), but was sensitive to the third generation EGFR TKIs (osimertinib and rociletinib). By contrast, the EGFR(T790M/C797S)-expressing cells were also resistant to the third generation EGFR TKIs. Likewise, crizotinib, which is a TKI for ALK and ROS1, suppressed proliferation of a cell expressing EML4-ALK or CD74-ROS1; and alectinib, which is another inhibitor for ALK and RET, inhibited proliferation of a cell expressing EML4-ALK or KIF5B-RET (FIG. 3). To independently assess sensitivity of EGFR mutants, Alamar Blue assay, which is an assay for quantifying cell viability based on a mitochondrial enzyme activity, was used to count the number of living cells. The read count of the MANO method and the relative fold number (indicating the number of cells) were correlated with Alamar Blue data (r=0.89; data not shown). These results are consistent with the reports using conventional assays and demonstrate that the MANO method is a method which can evaluate whether a cell having an oncogene is sensitive to a drug.

Further, 25 different 3T3 clones were pooled and xenografted subcutaneously into mice. Then, the mice were treated with a vehicle, erlotinib, or afatinib for 14 days. The erlotinib treatment caused a marked decrease in the relative abundance ratios of clones expressing 6 out of 6 different TKI-sensitive EGFR mutants (L858R, E746-A750del, L861Q, G719C, G719S, and S768I). However, at the same time, there was an increase in the relative abundance ratios of clones expressing 2 out of 2 different TKI-resistant EGFR mutants (T790M and T790M/C797S) and 9 out of 9 other oncogenes (data not shown). Similar results were obtained even in the afatinib treatment (data not shown). These results demonstrate that the MANO method can evaluate drug sensitivity in vivo.

Example 2: Evaluation of EGFR VUS (Variants of Unknown Significance) by MANO Method The materials and methods were as described in the "1. Cell Lines" to "5. In Vitro MANO Method" of Example 1. Provided that EGFR VUS were used as evaluation targets as follows.

The EGFR VUS used as evaluation targets in both BaF3 cells and 3T3 cells were 98 variants including the following: R108K, R252C, T263P, A289D, A289T, A289V, H304Y, S492R, P596L, G598V, L62R, L703P, E709-T710>D, E709A, E709G, E709K, E709V, G719A, G719C, G719S, S720F, G735S, P741L, K745-A750>T, K745-A750del, K745-E746insVPVAIK, K745-E749del, E746-A750>IP, E746-P753>VS, E746-P753del, E746-T751>V, L747-A750>P, L747-A750del, L747-P753>Q, L747-P753>S, L747-P753del, L747-T751>P, L747-T751>S, L747-T751del, L747S, T751-1759>N, T751I, 5752-1759del, P753S, D761-E762insEAFQ, A763-Y764insFQEA, V765M, A767V, S768I, V769-D770insASV, V769L, V769M, D770-N771insSVD, N771-P772insN, P772-H773insPR, H773-V774insH, H773-V774insPH, H773L, H773R, H773Y, V774-C775insHV, V774M, R776C, R776H, G779S, V786M, T790M, C797S, P798H, V802I, R831H, R831L, L833F, L833V, V834L, V834M, H835L, R836C, L838P, A839T, V843I, P848L, V851I, T854A, G857E, G857R, L858R, A859T, K860I, L861Q, A864T, E865K, A871G, A871T, G873E, G874S, and 511531. Other than the above, A1118T was assessed only in BaF3 cells and E746-E749del and R222C were assessed only in 3T3 cells (the total 101 EGFR mutants were evaluated). In addition, wild-type EGFR and GFP were included as controls.
(Results)

Figure 4:
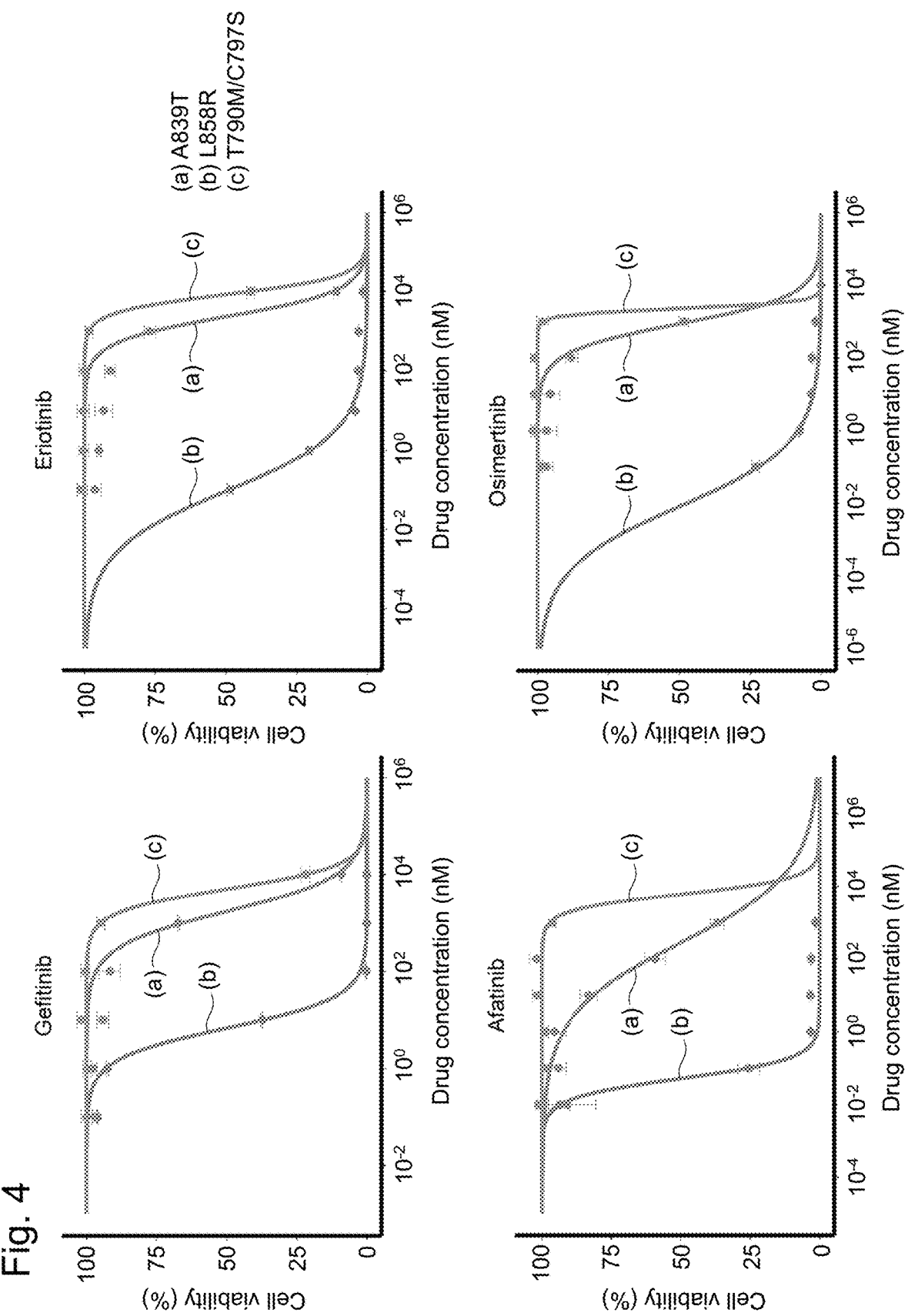
FIG. 4 shows the sensitivity of cells expressing each EGFR protein having A839T, L858R, or T790M/C797S to gefitinib, erlotinib, afatinib, or osimertinib. The abscissa indicates the drug concentration (nM) and the ordinate indicates the cell viability (%).

Here, 101 EGFR mutants, which have been reported in the COSMIC database 4 to 7386 times, were assessed by the MANO method. As a result, the assays in 3T3 cells and Ba/F3 cells have determined that the total of 80 EGFR mutants contribute to transforming potential (62 mutants were found in both the assays; 11 mutants were found only in 3T3 cells; and 7 mutants were found only in Ba/F3 cells). The mutants conferring stronger transforming potential than wild-type one in 3T3 cells or Ba/F3 cells were as follows: L62R, R108K, R222C, R252C, A289D, A289T, A289V, H304Y, S492R, P596L, G598V, L703P, E709-T710>D, E709A, E709G, E709K, E709V, G719A, G719C, G719S, S720F, G735S, P741L, K745-E746insVPVAIK, E746-A750>IP, E746-P753>VS, E746-T751>V, L747-A750>P, L747-A750del, L747-P753>Q, L747-P753>S, L747-T751>P, L747-T751>S, L747-T751del, L747S, T751-1759>N, T751I, 5752-1759del, P753S, D761-E762insEAFQ, A763-Y764insFQEA, V765M, A767V, 57681, V769-D770insASV, V769L, V769M, D770-N771insSVD, N771-P772insN, H773-V774insH, H773-V774insPH, H773L, H773Y, V774-C775insHV, V774M, R776C, R776H, G779S, V786M, P798H, V802I, R831H, R831L, L833F, L833V, V834L, V834M, H835L, V843I, P848L, V851I, L858R, A859T, K860I, L861Q, A864T, E865K, A871G, A871T, G873E, G874S, A1118T, and S1153I. Then, 22 EGFR mutants without transforming potential were further tested. Interestingly, A839T mutant was demonstrated to confer marked resistance to EGFR TKIs of all the generations (FIG. 4).

Example 3: Evaluation of Sensitivity to Small Molecular Compound in Cells with Oncogenic Mutation by MANO Method Next, the TKI (small molecular compound) sensitivity of each EGFR mutant was calculated as a drug sensitivity score by using the MANO method. As shown in FIG. 5, L858R and E746-A750del mutants were shown to be sensitive to any of the TKIs, whereas T790M, C797S, T790M/C797S, and T854A substitution mutants and an exon-20 insertion mutant exhibited resistance to some of the TKIs. These results have indicated that the MANO method is consistent with sensitivity data of previous studies. Interestingly, all of mutants with an extracellular domain mutation (exons 2 to 15), E709 mutation (exon 18), an exon-19 missense mutation, V769L (exon 20), or V851I (exon 21) was less sensitive to the TKIs than a mutant with L858R or an exon-19 deletion. The sensitivity of a mutant with an exon-20 insertion decreased in osimertinib or rociletinib treatment; but a change to N771-P772insN conferred higher sensitivity than the other mutants (FIG. 5).

Example 4: Evaluation of Compound Mutations by MANO Method

The materials and methods were as described in the "1. Cell Lines" to "5. In Vitro MANO Method" of Example 1. Provided that EGFR compound mutations were used as evaluation targets.
(Results)
The drug sensitivity score of each compound mutation was likewise calculated by the MANO method. The compound mutations shown in FIG. 6 were shown to have transforming potential (data not shown). In addition, the drug sensitivity of each compound mutation was tested. Then, different mutations exhibited different sensitivities to drugs (FIG. 6). Further, 3T3 focus-formation assay was conducted for each compound mutation. Almost no or no transforming potential was found for, in particular, L858R and E709V(cis), L858R and S720F(cis), and L858R and E709G(cis), whereas the other compound mutations tested were found to have transforming potential (FIG. 7).

Example 5: Evaluation of Sensitivity to Antibody Drug in Cells with Oncogenic Mutation by MANO Method The materials and methods were as described in the "1. Cell Lines" to "5. In Vitro MANO Method" of Example 1. Provided that single mutations or compound mutations of EGFR were evaluation targets and an antibody drug (cetuximab) was used as a drug.
(Results)
The antibody drug (cetuximab) was used to likewise conduct experiments and the drug sensitivity scores were calculated. The results revealed that the sensitivity to the antibody drug largely differed from the sensitivity to each small molecular compound (FIG. 8). It was also revealed that the sensitivity to the antibody drug substantially varied domain by domain and mutation by mutation (FIG. 8).

Example 6: Evaluation of Oncogenes which Suppress Differentiation by MANO-D (MANO-Differentiation) Method Materials and Methods
The materials and methods were as described in the "1. Cell Lines" to "5. In Vitro MANO Method" of Example 1. Provided that cells of interest were transfected, according to the manufacturer's protocol, with pTet-On Advanced Vector or a pTRE-Tight Vector having MYOD1 or RFP which is cloned by using the Tet-On Advanced inducible expression system (Clontech, Inc.), and the following tag-added genes (GFP, BRD3-NUT (French C A. et al., Oncogene, 2008 3; 27(15), pp. 2237-42), and COL1A2/DCAF6 fusion gene (SEQ ID NO: 8)) and the a differentiation-inducing transcription factor MYOD1 or RFP (Red fluorescent protein, control). The resulting cells were mixed and then cultured for 14 days under cell differentiation-inducing conditions (with 2% horse serum and 10 ng/mL DOX, which promotes expression of each transfected gene) or under regular conditions (with 10% FBS). After that, the cells were collected and were subjected to DNA extraction.

An equation for calculating the score about an ability to suppress differentiation is as follows:

$$\text{Score about an ability to suppress differentiation by gene } A \text{ of interest} = (AI_X \times T_X)/(A_X \times TI_X)$$

wherein $AI_X$=the read count of a bar code added to gene A of interest in cells collected at Day X after differentiation induction;
$T_x$=the total read count of all bar codes in cells collected at Day X;
$A_X$=the read count of the bar code added to gene A of interest in the cells collected at Day X; and
$TI_x$=the total read count of all bar codes in the cells collected at Day X after differentiation induction.
(The score about an ability to suppress differentiation by gene A of interest indicates that the higher the score is, the higher the ability to suppress differentiation by the gene A of interest is.)
(Results)
The table below shows the results of this test (scores about an ability to suppress differentiation).

TABLE 1

|  | RFP Expression 2% HS + dox | MYOD1 Expression 2% HS + dox | RFP Expression 10% FBS | MYOD1 Expression 10% FBS |
| --- | --- | --- | --- | --- |
| GFP | 0.6807 | 1.0437 | 0.5581 | 0.4287 |
| BRD3-NUT | 0.4592 | 2.5046 | 0.4708 | 0.4686 |
| COL1A2-DCAF6 | 0.7882 | 3.4662 | 0.4844 | 0.4429 |

For BRD3-NUT, which is an oncogene that suppresses differentiation, a higher value (2.5046) than the value (0.6807) for GFP was detected under differentiation-inducing conditions (with 2% HS+dox and MYOD1 expression). Thus, the MANO method were demonstrated to be capable of evaluating oncogenes that suppress differentiation. In addition, in this method, the COL1A2/DCAF6 fusion protein exhibited a high value (3.4662) under the differentiation-inducing conditions, suggesting that the COL1A2/DCAF6 fusion protein is a novel gene that suppresses differentiation.

Example 7: Evaluation of BRCA2 Genes by MANO-B (MANO-BRCA) Method

Materials and Methods

First, 3 different unique bar code sequences were added (to conduct experiments at n=3) to each of 11 different plasmids including: plasmids having wild-type BRCA2, K2729N mutation (benign), D2723H mutation (pathogenic), and 7 truncate variants in which a stop codon is introduced about every 500 amino acids (K485*, L997*, Q1502*, K1984*, C2535*, W2970*, C3304*); and piggyBac empty vector (System Biosciences, LLC). Accordingly, the total of 33 different plasmids were prepared. DLD1 BRCA2 (−/−) line was transfected with each plasmid and a transposase expression plasmid pCMV-hyPBase (Sanger Institute) in accordance with the manufacturer's protocol. In this way, cells having BRCA genes stably introduced in their genome were prepared.

Different cell lines having mutated genes tagged with bar code sequences introduced were mixed in equal numbers. At this time point, genomic DNA was once extracted (Day 0). Here, a PARP inhibitor (olaparib) was given at varied concentrations and then cultured. Genomic DNA was extracted from the cells collected at Day 12 and was used as a template to PCR-amplify each bar code sequence. After that, deep-sequencing was performed with a next-generation sequencer. The effects of each mutation on the drug sensitivity and the cell proliferation potential were assessed from a change in the ratio of bar code read counts between the case of no chemical treatment and the case of chemical treatment.

The results (the averages of n=3) of analyzing each sample collected at Day 12 are listed in Table 2. The results were normalized while the read count when no chemical was given was set to 1.

TABLE 2

|        | wild type | K2729N | D2723H | K485* | L997* | Q1502* | K1984* | C2535* | W2970* | C3304* | Empty vector |
|--------|-----------|--------|--------|-------|-------|--------|--------|--------|--------|--------|--------------|
| 0 M    | 1         | 1      | 1      | 1     | 1     | 1      | 1      | 1      | 1      | 1      | 1            |
| 1 nM   | 1.22      | 1.08   | 0.97   | 0.79  | 0.85  | 1      | 0.94   | 0.94   | 0.97   | 0.98   | 0.98         |
| 5 nM   | 1.52      | 1.58   | 0.76   | 0.66  | 0.71  | 0.88   | 0.84   | 0.78   | 0.93   | 1.14   | 0.82         |
| 10 nM  | 1.92      | 1.36   | 0.67   | 0.54  | 0.54  | 0.78   | 0.77   | 0.77   | 0.75   | 1.17   | 0.69         |
| 50 nM  | 3.19      | 1.74   | 0.34   | 0.26  | 0.24  | 0.43   | 0.36   | 0.4    | 0.45   | 0.94   | 0.38         |
| 100 nM | 3.82      | 2.31   | 0.18   | 0.15  | 0.13  | 0.24   | 0.25   | 0.27   | 0.22   | 0.69   | 0.21         |
| 500 nM | 4.2       | 4.76   | 0.07   | 0.06  | 0.06  | 0.12   | 0.08   | 0.08   | 0.09   | 0.3    | 0.07         |
| 1 μM   | 4.42      | 3.72   | 0.07   | 0.05  | 0.07  | 0.07   | 0.05   | 0.05   | 0.07   | 0.29   | 0.05         |

When functional BRCA2 is introduced into cells, homologous recombination-mediated repair function is restored, and thus the sensitivity to the drug, a PARP inhibitor, decreases and the cells become resistant to the inhibitor. By contrast, cells having a function-deficient BRCA2 introduced are sensitive to the PARP inhibitor, so that the relative cell count decreases when the PARP inhibitor is added. Based on such criteria, the function of each mutated BRCA2 was examined. K2729N mutant exhibited substantially the same resistance to the PARP inhibitor as the wild-type. Thus, the mutation was determined to be a function-preserving, benign mutation, which is consistent with past reports. By contrast, D2723H mutant did not exhibit resistance, so that the mutation was determined to be a function-deficient, pathogenic mutation, which is consistent with past reports.

In addition, in this Example, any of K485*, L997*, Q1502*, K1984*, C2535*, and W2970* was newly considered to be a function-deficient, cancer-related BRCA2 mutation.

Example 8: Evaluation of BRCA2 Genes by MANO-B (MANO-BRCA) Method

Figure 9:
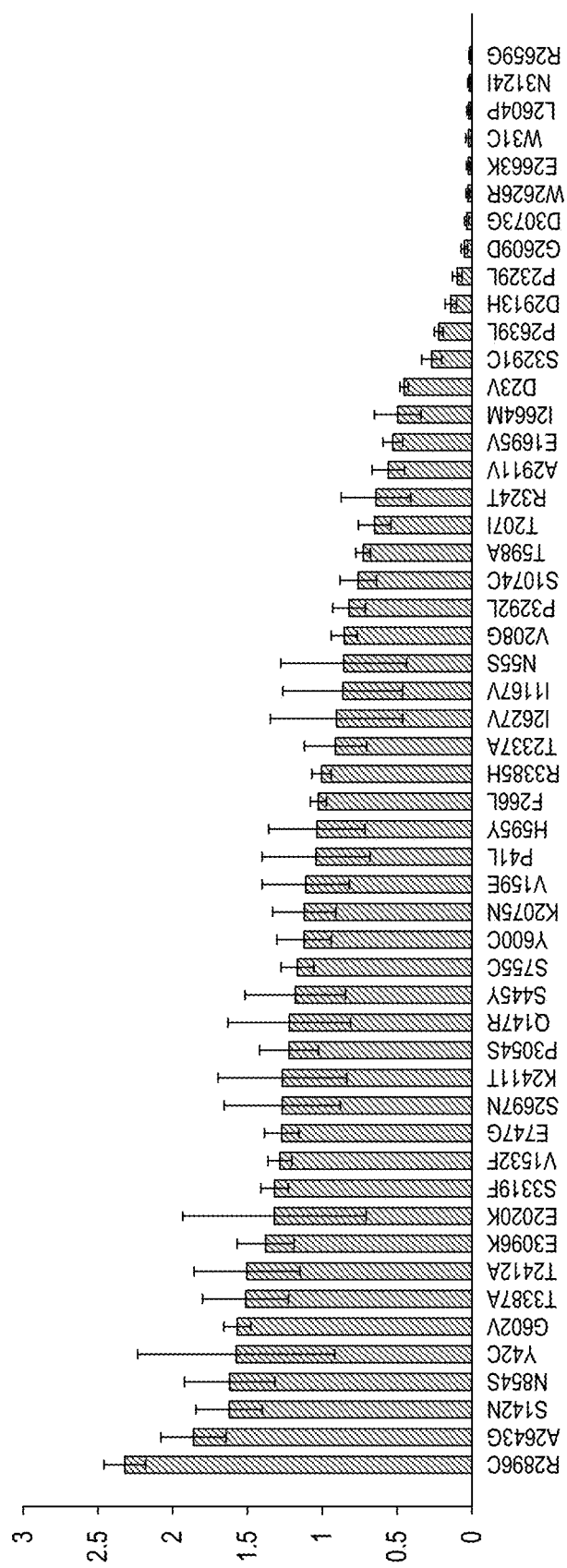
FIG. 9 shows the results of evaluating VUS and mutations with conflicting interpretations registered in the Clinvar by the MANO-B method.

Mutations registered at the Clinvar (https://www.ncbi.nlm.nih.gov/clinvar/) (18 kinds of benign mutation, 52 mutations of VUS or with conflicting interpretations, and 8 kinds of malignant mutation) were evaluated by the MANO-B method using the same procedure as of Example 7 (except that olaparib was used at 1 μM). As a result, most of the benign mutations or malignant mutations registered at the Clinvar were determined to be likewise benign or malignant, respectively, by the MANO-B method (data not shown). FIG. 9 shows the results of evaluating mutations of the VUS or with conflicting interpretations by the MANO-B method.

Among mutations having the consistent results between the MANO-B method and the ClinVar, the lowest score of the benign mutations was 0.73860142 (N2436I); and the highest score of the malignant mutations was 0.038385294 (G2724W). Accordingly, the thresholds were set to 0.1 and 0.5 and the mutations were grouped into 3 groups of benign, malignant, and impossible-to-determine mutations (possibly malignant mutations). This result allowed the mutations of the VUS or with conflicting interpretations to be grouped into 9 malignant mutants (R2659G, N3124I, L2604P, W31C, E2663K, W2626R, D3073G, G2609D, and P2329L), 5 impossible-to-determine mutants (D2913H, P2639L, S3291C, D23V, and I2664M), and 38 benign mutants (R2896C, A2643G, S142N, N854S, Y42C, G602V, T3387A, T2412A, E3096K, E2020K, S3319F, V1532F, E747G, S2697N, K2411T, P3054S, Q147R, S445Y, S755C, Y600C, K2075N, V159E, P41L, H595Y, F266L, R3385H, T2337A, I2627V, I1167V, N55S, V208G, P3292L, S1074C, T598A, T2071, R324T, A2911V, E1695V).

INDUSTRIAL APPLICABILITY

The present invention allows for a method for evaluating a function, such as transforming potential, of multiple different genes of interest and quick and accurate evaluation of whether a subject having each gene of interest is sensitive to a drug. The present invention can be used to evaluate whether each of many mutations of, for example, the VUS confers transforming potential and/or drug sensitivity. Hence, its industrial values are very high.

All the publications, patents, and patent applications cited herein are incorporated herein by reference in its entirety.

The invention claimed is:

1. A method for evaluating multiple different genes of interest, comprising the steps of:
   integrating, into host cell genomic DNA, polynucleotides each comprising a tag sequence and a gene of interest or a fragment thereof linked to the tag sequence;
   mixing a plurality of host cells having the different polynucleotides integrated therein;
   culturing the mixed host cells;
   extracting the genomic DNA from the cultured host cells;
   quantifying each of the polynucleotides in the extracted genomic DNA based on the tag sequence; and
   determining a relative cell count of each of the host cells having the respective polynucleotides after the culturing, based on the quantified values for the polynucleotides.

2. The method according to claim 1, wherein the gene of interest includes a reference gene, wherein the method comprises the step of comparing the relative cell count of the host cells after the culturing with a reference value, and wherein the reference value is defined as a relative cell count of a host cell comprising a polynucleotide comprising the reference gene after the culturing.

3. The method according to claim 2, further comprising the step of evaluating the gene of interest as having transforming potential, when the relative cell count after the culturing is higher than the reference value.

4. The method according to claim 2, wherein
   the culturing is performed under a differentiation-inducing condition, and
   the method further comprises the step of evaluating the gene of interest as a gene that suppresses the differentiation, when the relative cell count after the culturing is higher than the reference value.

5. The method according to claim 1, wherein the culturing is performed under a test environment.

6. The method according to claim 5, wherein the test environment is in the presence of a test substance.

7. The method according to claim 6, wherein the genes of interest is oncogene, wherein the culturing is performed in a presence of an anti-cancer drug, and wherein the method comprises the step of evaluating sensitivity of the oncogene to the anti-cancer drug based on the relative cell count after the culturing.

8. The method according to claim 7, wherein the anti-cancer drug is a low-molecular-weight compound and/or an antibody drug.

9. A method for determining an anti-cancer drug, comprising the step of performing the method according to claim 7 for a plurality of anti-cancer drugs once or multiple times independently to determine an anti-cancer drug effective for the oncogene based on the obtained results of sensitivities to the anti-cancer drugs.

10. The method according to claim 6, wherein the gene of interest is an tumor suppressor gene, wherein the host cells are cells deficient in the tumor suppressor gene, and the culturing is performed under treatment which causes the damage to the host cells that can be repaired by the tumor suppressor gene.

11. The method according to claim 10, wherein the test substance is a PARP inhibitor.

12. The method according to claim 1, wherein the plurality of host cells having the different polynucleotides integrated therein are derived from the same cell line.

13. The method according to claim 1, wherein the gene of interest includes a plurality of mutants of one oncogene.

14. The method according to claim 1, wherein the gene of interest includes a compound mutation-bearing gene containing a plurality of mutations to a wild-type gene.

15. The method according to claim 1, wherein the quantifying step is performed based on read counts obtained by next-generation sequencing.

16. The method according to claim 1, wherein the culturing is performed in vivo using a non-human animal.

* * * * *